(12) United States Patent
López Cortajarena et al.

(10) Patent No.: US 11,377,475 B2
(45) Date of Patent: Jul. 5, 2022

(54) METAL NANOCLUSTER SCAFFOLDS

(71) Applicant: ASOCIACIÓN CENTRO DE INVESTIGACIÓN COOPERATIVA EN BIOMATERIALES—CIC BIOMAGUNE, San Sebastián (ES)

(72) Inventors: Aitziber López Cortajarena, San Sebastian (ES); Antonio Aires Trapote, San Sebastian (ES)

(73) Assignee: ASOCIACIÓN CENTRO DE INVESTIGACIÓN COOPERATIVA EN BIOMATERIALES—CIC BIOMAGUNE, San Sebastián (ES)

( * ) Notice: Subject to any disclaimer, the term of this patent is extended or adjusted under 35 U.S.C. 154(b) by 134 days.

(21) Appl. No.: 16/630,396

(22) PCT Filed: Jul. 10, 2018

(86) PCT No.: PCT/EP2018/068710
§ 371 (c)(1),
(2) Date: Jan. 10, 2020

(87) PCT Pub. No.: WO2019/011938
PCT Pub. Date: Jan. 17, 2019

(65) Prior Publication Data
US 2021/0002330 A1 Jan. 7, 2021

(30) Foreign Application Priority Data
Jul. 11, 2017 (EP) ..................... 17382451

(51) Int. Cl.
*C07K 7/08* (2006.01)
*A61K 49/00* (2006.01)
*C07K 19/00* (2006.01)
*G01N 21/64* (2006.01)

(52) U.S. Cl.
CPC ............ *C07K 7/08* (2013.01); *A61K 49/0056* (2013.01); *C07K 19/00* (2013.01); *G01N 21/6428* (2013.01)

(58) Field of Classification Search
None
See application file for complete search history.

(56) References Cited

PUBLICATIONS

International Search Report and Written Opinion dated Oct. 15, 2018 for PCT Application No. PCT/EP2018/068710, 19 pages.
Cortajarena, et al: "Modulating repeat protein stability: The effect of individual helix stability on the collective behavior of the ensemble", Protein Science 2011, vol. 20, No. 6, pp. 1042-1047, XP-055510322, Jun. 1, 2011.
Cortajarena, et al: "Non-random-coil behavior as a consequence of extensive PPII structure in the denatured state", Journal Molecular Biology, Academic Press, vol. 382, No. 1, pp. 203-212, XP-023906568, Jul. 11, 2008.
Cortajarena, et al: "Protein design to understand peptide ligand recognition by tetratricopeptide repeat proteins", Protein Engineering, Design & Selection: PEDS Apr. 2004, vol. 17, No. 4, pp. 399-409, XP-002773683, online May 27, 2004.
Couleaud, et al: "Designed modular proteins as scaffolds to stabilize fluorescent nanoclusters", Journal American Chemical Society, Biomacromolecules 2015, vol. 16, No. 12, pp. 3836-3844, XP-002773682, Nov. 4, 2015.
D'Andrea, et al: "TPR proteins: the versatile helix", Trends in Biochemical Sciences, vol. 28, No. 12, pp. 655-662, XP-004476604, Dec. 1, 2003.
Geng, et al: "Repeat protein mediated synthesis of gold nanoparticles: effect of protein shape on the morphological and optical properties", RSC Advances, vol. 5, No. 3, pp. 2062-2069, XP-055510470, Dec. 5, 2014.
Kajander, et al: "Structure and stability of designed TPR protein superhelices: unusual crystal packing and implications for natural TPR proteins", ACTA Crystallographica Section D: Biological Cyrstallography, vol. 63, No. 7, pp. 800-811, XP-055406133, Jun. 15, 2007.
Makarov, et al: "Green nanotechnologies: synthesis of metal nanoparticles using plants", ACTA Naturae, vol. 6, No. 1, pp. 35-44, XP-055510924, Jan. 1, 2014.
Mejias, et al: "Assembly of designed protein scaffolds into monolayers for nanoparticle patterning", Colloids and Surfaces B: Biointerfaces, Elsevier, vol. 141, 93-101, XP-029465859, Jan. 22, 2016.
Shang, et al: "Ultra-small fluorescent metal nanoclusters: synthesis and biological applications", Nano Today, Elsevier, vol. 6, No. 4, pp. 401-418, XP-028264594, Jun. 19, 2011.
Xie, et al: "Protein-directed synthesis of highly fluorescent gold nanoclusters", Journal American Chemical Society, vol. 131, No. 3, pp. 888-889, XP-055080345, Jan. 28, 2009.
Huang, et al: "Green synthesis of peptide-templated fluorescent copper nanoclusters for temperature sensing and cellular imaging", The Royal Society of Chemistry, Analyst Accepted Manuscript, 2014, DOI: 10.1039/c4an01757a; pp. 1-25.
Li, et al: "Fluorescent metal nanoclusters: from synthesis to applications", Trends in Analytical Chemistry 2014, vol. 58, pp. 90-98.
Qu, et al: "Fluorescent gold nanoclusters: synthesis and recent biological application", Journal of Nanomaterials 2015, vol. 2015, Article ID 784097, 23 pages.

*Primary Examiner* — Anand U Desai
(74) *Attorney, Agent, or Firm* — Squire Patton Boggs (US) LLP

(57) ABSTRACT

The present invention refers to a protein-stabilized metal nanocluster comprising a variant of the helix A of the CTPR. It is also related to its uses for delivering of a drug, for interfering a metabolic reaction, for catalyzing a chemical reaction, as biocatalyst, for detecting an analyte, for phasing crystallographic data set, for cell labeling, for specific protein labeling, as biosensor, as a temperature sensor, as photosensitizer, or for the manufacture of an optoelectronic device.

19 Claims, 13 Drawing Sheets
Specification includes a Sequence Listing.

SEQUENCE LISTING

```
<160> NUMBER OF SEQ ID NOS: 170

<210> SEQ ID NO 1
<211> LENGTH: 13
<212> TYPE: PRT
<213> ORGANISM: Artificial Sequence
<220> FEATURE:
<223> OTHER INFORMATION: amino acid sequence
<220> FEATURE:
<221> NAME/KEY: misc_feature
<222> LOCATION: (2)..(2)
<223> OTHER INFORMATION: E, H, C or D
<220> FEATURE:
<221> NAME/KEY: misc_feature
<222> LOCATION: (5)..(5)
<223> OTHER INFORMATION: Y, H, C, D or E
<220> FEATURE:
<221> NAME/KEY: misc_feature
<222> LOCATION: (6)..(6)
<223> OTHER INFORMATION: N, H, C, D or E
<220> FEATURE:
<221> NAME/KEY: misc_feature
<222> LOCATION: (9)..(9)
<223> OTHER INFORMATION: N, H, C, D or E
<220> FEATURE:
<221> NAME/KEY: misc_feature
<222> LOCATION: (12)..(12)
<223> OTHER INFORMATION: Y, H, L, A, V, C, D or E
<220> FEATURE:
<221> NAME/KEY: misc_feature
<222> LOCATION: (13)..(13)
<223> OTHER INFORMATION: K, H, C, D or E

<400> SEQUENCE: 1

Ala Xaa Ala Trp Xaa Xaa Leu Gly Xaa Ala Tyr Xaa Xaa
1               5                   10

<210> SEQ ID NO 2
<211> LENGTH: 13
<212> TYPE: PRT
<213> ORGANISM: Artificial Sequence
<220> FEATURE:
<223> OTHER INFORMATION: amino acid sequence
<220> FEATURE:
<221> NAME/KEY: MISC_FEATURE
<222> LOCATION: (2)..(2)
<223> OTHER INFORMATION: E, H, C or D
<220> FEATURE:
<221> NAME/KEY: MISC_FEATURE
<222> LOCATION: (5)..(5)
<223> OTHER INFORMATION: Y, H, C, D or E

<400> SEQUENCE: 2

Ala Xaa Ala Trp Xaa Asn Leu Gly Asn Ala Tyr Tyr Lys
1               5                   10

<210> SEQ ID NO 3
<211> LENGTH: 13
<212> TYPE: PRT
<213> ORGANISM: Artificial Sequence
<220> FEATURE:
<223> OTHER INFORMATION: amino acid sequence
```

```
<220> FEATURE:
<221> NAME/KEY: MISC_FEATURE
<222> LOCATION: (2)..(2)
<223> OTHER INFORMATION: E, H, C or D
<220> FEATURE:
<221> NAME/KEY: MISC_FEATURE
<222> LOCATION: (6)..(6)
<223> OTHER INFORMATION: N, H, C, D or E

<400> SEQUENCE: 3

Ala Xaa Ala Trp Tyr Xaa Leu Gly Asn Ala Tyr Tyr Lys
1               5                   10

<210> SEQ ID NO 4
<211> LENGTH: 13
<212> TYPE: PRT
<213> ORGANISM: Artificial Sequence
<220> FEATURE:
<223> OTHER INFORMATION: amino acid sequence
<220> FEATURE:
<221> NAME/KEY: MISC_FEATURE
<222> LOCATION: (5)..(5)
<223> OTHER INFORMATION: Y, H, C, D or E
<220> FEATURE:
<221> NAME/KEY: MISC_FEATURE
<222> LOCATION: (9)..(9)
<223> OTHER INFORMATION: N, H, C, D or E

<400> SEQUENCE: 4

Ala Glu Ala Trp Xaa Asn Leu Gly Xaa Ala Tyr Tyr Lys
1               5                   10

<210> SEQ ID NO 5
<211> LENGTH: 13
<212> TYPE: PRT
<213> ORGANISM: Artificial Sequence
<220> FEATURE:
<223> OTHER INFORMATION: amino acid sequence
<220> FEATURE:
<221> NAME/KEY: MISC_FEATURE
<222> LOCATION: (6)..(6)
<223> OTHER INFORMATION: N, H, C, D or E
<220> FEATURE:
<221> NAME/KEY: MISC_FEATURE
<222> LOCATION: (9)..(9)
<223> OTHER INFORMATION: N, H, C, D or E

<400> SEQUENCE: 5

Ala Glu Ala Trp Tyr Xaa Leu Gly Xaa Ala Tyr Tyr Lys
1               5                   10

<210> SEQ ID NO 6
<211> LENGTH: 13
<212> TYPE: PRT
<213> ORGANISM: Artificial Sequence
<220> FEATURE:
<223> OTHER INFORMATION: amino acid sequence
<220> FEATURE:
<221> NAME/KEY: MISC_FEATURE
<222> LOCATION: (9)..(9)
<223> OTHER INFORMATION: N, H, C, D or E
<220> FEATURE:
<221> NAME/KEY: MISC_FEATURE
<222> LOCATION: (12)..(12)
<223> OTHER INFORMATION: Y, H, L, A, V, C, D or E

<400> SEQUENCE: 6

Ala Glu Ala Trp Tyr Asn Leu Gly Xaa Ala Tyr Xaa Lys
1               5                   10
```

-continued

```
<210> SEQ ID NO 7
<211> LENGTH: 13
<212> TYPE: PRT
<213> ORGANISM: Artificial Sequence
<220> FEATURE:
<223> OTHER INFORMATION: amino acid sequence
<220> FEATURE:
<221> NAME/KEY: MISC_FEATURE
<222> LOCATION: (2)..(2)
<223> OTHER INFORMATION: E, H, C or D
<220> FEATURE:
<221> NAME/KEY: MISC_FEATURE
<222> LOCATION: (5)..(5)
<223> OTHER INFORMATION: Y, H, C, D or E
<220> FEATURE:
<221> NAME/KEY: MISC_FEATURE
<222> LOCATION: (9)..(9)
<223> OTHER INFORMATION: N, H, C, D or E

<400> SEQUENCE: 7

Ala Xaa Ala Trp Xaa Asn Leu Gly Xaa Ala Tyr Tyr Lys
1               5                   10

<210> SEQ ID NO 8
<211> LENGTH: 13
<212> TYPE: PRT
<213> ORGANISM: Artificial Sequence
<220> FEATURE:
<223> OTHER INFORMATION: amino acid sequence
<220> FEATURE:
<221> NAME/KEY: MISC_FEATURE
<222> LOCATION: (2)..(2)
<223> OTHER INFORMATION: E, H, C or D
<220> FEATURE:
<221> NAME/KEY: MISC_FEATURE
<222> LOCATION: (6)..(6)
<223> OTHER INFORMATION: N, H, C, D or E
<220> FEATURE:
<221> NAME/KEY: MISC_FEATURE
<222> LOCATION: (9)..(9)
<223> OTHER INFORMATION: N, H, C, D or E

<400> SEQUENCE: 8

Ala Xaa Ala Trp Tyr Xaa Leu Gly Xaa Ala Tyr Tyr Lys
1               5                   10

<210> SEQ ID NO 9
<211> LENGTH: 13
<212> TYPE: PRT
<213> ORGANISM: Artificial Sequence
<220> FEATURE:
<223> OTHER INFORMATION: amino acid sequence
<220> FEATURE:
<221> NAME/KEY: MISC_FEATURE
<222> LOCATION: (5)..(5)
<223> OTHER INFORMATION: Y, H, C, D or E
<220> FEATURE:
<221> NAME/KEY: MISC_FEATURE
<222> LOCATION: (9)..(9)
<223> OTHER INFORMATION: N, H, C, D or E
<220> FEATURE:
<221> NAME/KEY: MISC_FEATURE
<222> LOCATION: (12)..(12)
<223> OTHER INFORMATION: Y, H, L, A, V, C, D or E

<400> SEQUENCE: 9

Ala Glu Ala Trp Xaa Asn Leu Gly Xaa Ala Tyr Xaa Lys
1               5                   10

<210> SEQ ID NO 10
<211> LENGTH: 13
<212> TYPE: PRT
<213> ORGANISM: Artificial Sequence
```

```
<220> FEATURE:
<223> OTHER INFORMATION: amino acid sequence
<220> FEATURE:
<221> NAME/KEY: MISC_FEATURE
<222> LOCATION: (6)..(6)
<223> OTHER INFORMATION: N, H, C, D or E
<220> FEATURE:
<221> NAME/KEY: MISC_FEATURE
<222> LOCATION: (9)..(9)
<223> OTHER INFORMATION: N, H, C, D or E
<220> FEATURE:
<221> NAME/KEY: MISC_FEATURE
<222> LOCATION: (12)..(12)
<223> OTHER INFORMATION: Y, H, L, A, V, C, D or E

<400> SEQUENCE: 10

Ala Glu Ala Trp Tyr Xaa Leu Gly Xaa Ala Tyr Xaa Lys
1               5                   10

<210> SEQ ID NO 11
<211> LENGTH: 13
<212> TYPE: PRT
<213> ORGANISM: Artificial Sequence
<220> FEATURE:
<223> OTHER INFORMATION: amino acid sequence
<220> FEATURE:
<221> NAME/KEY: MISC_FEATURE
<222> LOCATION: (2)..(2)
<223> OTHER INFORMATION: E, H, C or D
<220> FEATURE:
<221> NAME/KEY: MISC_FEATURE
<222> LOCATION: (5)..(5)
<223> OTHER INFORMATION: Y, H, C, D or E
<220> FEATURE:
<221> NAME/KEY: MISC_FEATURE
<222> LOCATION: (9)..(9)
<223> OTHER INFORMATION: N, H, C, D or E
<220> FEATURE:
<221> NAME/KEY: MISC_FEATURE
<222> LOCATION: (12)..(12)
<223> OTHER INFORMATION: Y, H, L, A, V, C, D or E

<400> SEQUENCE: 11

Ala Xaa Ala Trp Xaa Asn Leu Gly Xaa Ala Tyr Xaa Lys
1               5                   10

<210> SEQ ID NO 12
<211> LENGTH: 13
<212> TYPE: PRT
<213> ORGANISM: Artificial Sequence
<220> FEATURE:
<223> OTHER INFORMATION: amino acid sequence
<220> FEATURE:
<221> NAME/KEY: MISC_FEATURE
<222> LOCATION: (2)..(2)
<223> OTHER INFORMATION: E, H, C or D
<220> FEATURE:
<221> NAME/KEY: MISC_FEATURE
<222> LOCATION: (6)..(6)
<223> OTHER INFORMATION: N, H, C, D or E
<220> FEATURE:
<221> NAME/KEY: MISC_FEATURE
<222> LOCATION: (9)..(9)
<223> OTHER INFORMATION: N, H, C, D or E
<220> FEATURE:
<221> NAME/KEY: MISC_FEATURE
<222> LOCATION: (12)..(12)
<223> OTHER INFORMATION: Y, H, L, A, V, C, D or E

<400> SEQUENCE: 12

Ala Xaa Ala Trp Tyr Xaa Leu Gly Xaa Ala Tyr Xaa Lys
1               5                   10
```

```
<210> SEQ ID NO 13
<211> LENGTH: 13
<212> TYPE: PRT
<213> ORGANISM: Artificial Sequence
<220> FEATURE:
<223> OTHER INFORMATION: amino acid sequence
<220> FEATURE:
<221> NAME/KEY: MISC_FEATURE
<222> LOCATION: (2)..(2)
<223> OTHER INFORMATION: E, H, C or D
<220> FEATURE:
<221> NAME/KEY: MISC_FEATURE
<222> LOCATION: (6)..(6)
<223> OTHER INFORMATION: N, H, C, D or E
<220> FEATURE:
<221> NAME/KEY: MISC_FEATURE
<222> LOCATION: (9)..(9)
<223> OTHER INFORMATION: N, H, C, D or E
<220> FEATURE:
<221> NAME/KEY: MISC_FEATURE
<222> LOCATION: (12)..(12)
<223> OTHER INFORMATION: Y, H, L, A, V, C, D or E
<220> FEATURE:
<221> NAME/KEY: MISC_FEATURE
<222> LOCATION: (13)..(13)
<223> OTHER INFORMATION: K, H, C, D or E

<400> SEQUENCE: 13

Ala Xaa Ala Trp Tyr Xaa Leu Gly Xaa Ala Tyr Xaa Xaa
1               5                   10

<210> SEQ ID NO 14
<211> LENGTH: 13
<212> TYPE: PRT
<213> ORGANISM: Artificial Sequence
<220> FEATURE:
<223> OTHER INFORMATION: amino acid sequence

<400> SEQUENCE: 14

Ala Cys Ala Trp Tyr Cys Leu Gly Asn Ala Tyr Tyr Lys
1               5                   10

<210> SEQ ID NO 15
<211> LENGTH: 13
<212> TYPE: PRT
<213> ORGANISM: Artificial Sequence
<220> FEATURE:
<223> OTHER INFORMATION: amino acid sequence

<400> SEQUENCE: 15

Ala Glu Ala Trp His Asn Leu Gly His Ala Tyr Tyr Lys
1               5                   10

<210> SEQ ID NO 16
<211> LENGTH: 13
<212> TYPE: PRT
<213> ORGANISM: Artificial Sequence
<220> FEATURE:
<223> OTHER INFORMATION: amino acid sequence

<400> SEQUENCE: 16

Ala Glu Ala Trp Cys Asn Leu Gly Cys Ala Tyr Tyr Lys
1               5                   10

<210> SEQ ID NO 17
<211> LENGTH: 13
<212> TYPE: PRT
<213> ORGANISM: Artificial Sequence
<220> FEATURE:
<223> OTHER INFORMATION: amino acid sequence
```

```
<400> SEQUENCE: 17

Ala Cys Ala Trp Tyr Cys Leu Gly Cys Ala Tyr Tyr Lys
1               5                   10

<210> SEQ ID NO 18
<211> LENGTH: 13
<212> TYPE: PRT
<213> ORGANISM: Artificial Sequence
<220> FEATURE:
<223> OTHER INFORMATION: amino acid sequence

<400> SEQUENCE: 18

Ala Cys Ala Trp Tyr Cys Leu Gly Cys Ala Tyr Leu Cys
1               5                   10

<210> SEQ ID NO 19
<211> LENGTH: 13
<212> TYPE: PRT
<213> ORGANISM: Artificial Sequence
<220> FEATURE:
<223> OTHER INFORMATION: amino acid sequence

<400> SEQUENCE: 19

Ala Glu Ala Trp Tyr Asn Leu Gly Asn Ala Tyr Tyr Lys
1               5                   10

<210> SEQ ID NO 20
<211> LENGTH: 14
<212> TYPE: PRT
<213> ORGANISM: Artificial Sequence
<220> FEATURE:
<223> OTHER INFORMATION: helix in C-terminal of general sequence

<400> SEQUENCE: 20

Tyr Asp Glu Ala Ile Glu Tyr Tyr Gln Lys Ala Leu Glu Leu
1               5                   10

<210> SEQ ID NO 21
<211> LENGTH: 14
<212> TYPE: PRT
<213> ORGANISM: Artificial Sequence
<220> FEATURE:
<223> OTHER INFORMATION: alpha helix sequence

<400> SEQUENCE: 21

Tyr Asp Lys Ala Ile Glu Tyr Tyr Gln Lys Ala Leu Glu Leu
1               5                   10

<210> SEQ ID NO 22
<211> LENGTH: 14
<212> TYPE: PRT
<213> ORGANISM: Artificial Sequence
<220> FEATURE:
<223> OTHER INFORMATION: alpha helix sequence

<400> SEQUENCE: 22

Tyr Gln Lys Ala Ile Glu Tyr Tyr Gln Lys Ala Leu Glu Leu
1               5                   10

<210> SEQ ID NO 23
<211> LENGTH: 4
<212> TYPE: PRT
<213> ORGANISM: Artificial Sequence
<220> FEATURE:
<223> OTHER INFORMATION: C-terminal end of helix alfa
```

<400> SEQUENCE: 23

Asp Pro Arg Ser
1

<210> SEQ ID NO 24
<211> LENGTH: 4
<212> TYPE: PRT
<213> ORGANISM: Artificial Sequence
<220> FEATURE:
<223> OTHER INFORMATION: C-terminal end of helix alpha

<400> SEQUENCE: 24

Asp Pro Asn Ala
1

<210> SEQ ID NO 25
<211> LENGTH: 4
<212> TYPE: PRT
<213> ORGANISM: Artificial Sequence
<220> FEATURE:
<223> OTHER INFORMATION: C-terminal end of helix alpha

<400> SEQUENCE: 25

Asp Pro Asn Asn
1

<210> SEQ ID NO 26
<211> LENGTH: 21
<212> TYPE: PRT
<213> ORGANISM: Artificial Sequence
<220> FEATURE:
<223> OTHER INFORMATION: C-terminal end sequence

<400> SEQUENCE: 26

Gln Gly Asp Tyr Asp Glu Ala Ile Glu Tyr Tyr Gln Lys Ala Leu Glu
1               5                   10                  15

Leu Asp Pro Arg Ser
            20

<210> SEQ ID NO 27
<211> LENGTH: 34
<212> TYPE: PRT
<213> ORGANISM: Artificial Sequence
<220> FEATURE:
<223> OTHER INFORMATION: CTPR1 Y5H N9H

<400> SEQUENCE: 27

Ala Glu Ala Trp His Asn Leu Gly His Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser

<210> SEQ ID NO 28
<211> LENGTH: 102
<212> TYPE: DNA
<213> ORGANISM: Artificial Sequence
<220> FEATURE:
<223> OTHER INFORMATION: CTPR1 Y5H N9H

<400> SEQUENCE: 28
gctgaggcat ggcacaacct gggtcacgct tactacaaac agggtgacta cgacgaagct    60
atcgaatact accagaaggc tctcgagctg gacccgagat cc                      102

<210> SEQ ID NO 29
<211> LENGTH: 34
<212> TYPE: PRT
<213> ORGANISM: Artificial Sequence
<220> FEATURE:
<223> OTHER INFORMATION: CTPR1 Y5C N9C

<400> SEQUENCE: 29

Ala Glu Ala Trp Cys Asn Leu Gly Cys Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser

<210> SEQ ID NO 30
<211> LENGTH: 102
<212> TYPE: DNA
<213> ORGANISM: Artificial Sequence
<220> FEATURE:
<223> OTHER INFORMATION: CTPR1 Y5C N9C

<400> SEQUENCE: 30
gctgaggcat ggtgcaacct gggttgcgct tactacaaac agggtgacta cgacgaagct    60
atcgaatact accagaaggc tctcgagctg acccgagat cc                        102

<210> SEQ ID NO 31
<211> LENGTH: 34
<212> TYPE: PRT
<213> ORGANISM: Artificial Sequence
<220> FEATURE:
<223> OTHER INFORMATION: CTPR1 C1

<400> SEQUENCE: 31

Ala Cys Ala Trp Tyr Cys Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser

<210> SEQ ID NO 32
<211> LENGTH: 102
<212> TYPE: DNA
<213> ORGANISM: Artificial Sequence
<220> FEATURE:
<223> OTHER INFORMATION: CTPR1 C1

<400> SEQUENCE: 32
gcttgtgcat ggtactgcct gggtaacgct tactacaaac agggtgacta cgacgaagct    60
atcgaatact accagaaggc tctcgagctg acccgagat cc                        102

<210> SEQ ID NO 33
<211> LENGTH: 34
<212> TYPE: PRT
<213> ORGANISM: Artificial Sequence
<220> FEATURE:
<223> OTHER INFORMATION: CTPR C2

<400> SEQUENCE: 33

Ala Cys Ala Trp Tyr Cys Leu Gly Cys Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser

<210> SEQ ID NO 34
<211> LENGTH: 102
<212> TYPE: DNA
<213> ORGANISM: Artificial Sequence
<220> FEATURE:
<223> OTHER INFORMATION: CTPR C2

<400> SEQUENCE: 34
gcttgtgcat ggtactgcct gggttgcgct tactacaaac agggtgacta cgacgaagct    60
atcgaatact accagaaggc tctcgagctg acccgagat cc                       102

<210> SEQ ID NO 35
<211> LENGTH: 34
<212> TYPE: PRT
<213> ORGANISM: Artificial Sequence
<220> FEATURE:
<223> OTHER INFORMATION: CTPR1 C3

<400> SEQUENCE: 35

Ala Cys Ala Trp Tyr Cys Leu Gly Cys Ala Tyr Leu Cys Gln Gly Asp
1               5                   10                  15

Tyr Asp Glu Ala Ile Glu Tyr Tyr Gln Lys Ala Leu Glu Leu Asp Pro
            20                  25                  30

Arg Ser

<210> SEQ ID NO 36
<211> LENGTH: 102
<212> TYPE: DNA
<213> ORGANISM: Artificial Sequence
<220> FEATURE:
<223> OTHER INFORMATION: CTPR1 C3

<400> SEQUENCE: 36
gcttgtgcat ggtactgcct gggttgcgct tacctctgcc agggtgacta cgacgaagct    60
atcgaatact accagaaggc tctcgagctg acccgagat ct                       102

<210> SEQ ID NO 37
<211> LENGTH: 34
<212> TYPE: PRT
<213> ORGANISM: Artificial Sequence
<220> FEATURE:
<223> OTHER INFORMATION: CTPR1 W

<400> SEQUENCE: 37

Ala Glu Ala Trp Tyr Asn Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser

<210> SEQ ID NO 38
<211> LENGTH: 102
<212> TYPE: DNA
<213> ORGANISM: Artificial Sequence

```
<220> FEATURE:
<223> OTHER INFORMATION: CTPR1 W

<400> SEQUENCE: 38
gctgaggcat ggtacaacct gggttacgct tactacaaac agggtgacta cgacgaagct    60
atcgaatact accagaaggc tctcgagctg gacccgagat cc                      102

<210> SEQ ID NO 39
<211> LENGTH: 102
<212> TYPE: PRT
<213> ORGANISM: Artificial Sequence
<220> FEATURE:
<223> OTHER INFORMATION: CTPR3 WWW

<400> SEQUENCE: 39

Ala Glu Ala Trp Tyr Asn Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser Ala Glu Ala Trp Tyr Asn Leu Gly Asn Ala Tyr Tyr Lys Gln
        35                  40                  45

Gly Asp Tyr Asp Glu Ala Ile Glu Tyr Tyr Gln Lys Ala Leu Glu Leu
    50                  55                  60

Asp Pro Arg Ser Ala Glu Ala Trp Tyr Asn Leu Gly Asn Ala Tyr Tyr
65                  70                  75                  80

Lys Gln Gly Asp Tyr Asp Glu Ala Ile Glu Tyr Tyr Gln Lys Ala Leu
                85                  90                  95

Glu Leu Asp Pro Arg Ser
            100

<210> SEQ ID NO 40
<211> LENGTH: 306
<212> TYPE: DNA
<213> ORGANISM: Artificial Sequence
<220> FEATURE:
<223> OTHER INFORMATION: CTPR3 WWW

<400> SEQUENCE: 40
gctgaggcat ggtacaacct gggtaacgct tactacaaac agggtgacta cgacgaagct    60
atcgaatact accagaaggc tctcgagctg gacccgagat ccgctgaggc atggtacaac   120
ctgggtaacg cttactacaa acagggtgac tacgacgaag ctatcgaata ctaccagaag   180
gctctcgagc tggacccgag atccgctgag gcatggtaca acctgggtaa cgcttactac   240
aaacagggtg actacgacga agctatcgaa tactaccaga aggctctcga gctggacccg   300
agatcc                                                             306

<210> SEQ ID NO 41
<211> LENGTH: 102
<212> TYPE: PRT
<213> ORGANISM: Artificial Sequence
<220> FEATURE:
<223> OTHER INFORMATION: CTPR3 HWW

<400> SEQUENCE: 41

Ala Glu Ala Trp His Asn Leu Gly His Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30
```

```
Arg Ser Ala Glu Ala Trp Tyr Asn Leu Gly Asn Ala Tyr Tyr Lys Gln
        35                  40                  45

Gly Asp Tyr Asp Glu Ala Ile Glu Tyr Tyr Gln Lys Ala Leu Glu Leu
 50                  55                  60

Asp Pro Arg Ser Ala Glu Ala Trp Tyr Asn Leu Gly Asn Ala Tyr Tyr
 65              70                  75                  80

Lys Gln Gly Asp Tyr Asp Glu Ala Ile Glu Tyr Tyr Gln Lys Ala Leu
                 85                  90                  95

Glu Leu Asp Pro Arg Ser
            100
```

<210> SEQ ID NO 42
<211> LENGTH: 306
<212> TYPE: DNA
<213> ORGANISM: Artificial Sequence
<220> FEATURE:
<223> OTHER INFORMATION: CTPR3 HWW

<400> SEQUENCE: 42

```
gctgaggcat ggcacaacct gggtcacgct tactacaaac agggtgacta cgacgaagct    60
atcgaatact accagaaggc tctcgagctg acccgagat ccgctgaggc atggtacaac    120
ctgggtaacg cttactacaa acagggtgac tacgacgaag ctatcgaata ctaccagaag    180
gctctcgagc tggacccgag atccgctgag gcatggtaca acctgggtaa cgcttactac    240
aaacagggtg actacgacga agctatcgaa tactaccaga aggctctcga gctggacccg    300
agatcc                                                              306
```

<210> SEQ ID NO 43
<211> LENGTH: 102
<212> TYPE: PRT
<213> ORGANISM: Artificial Sequence
<220> FEATURE:
<223> OTHER INFORMATION: CTPR3 WHW

<400> SEQUENCE: 43

```
Ala Glu Ala Trp Tyr Asn Leu Gly Asn Ala Tyr Tyr Lys Gln Gly Asp
 1               5                  10                  15

Tyr Asp Glu Ala Ile Glu Tyr Tyr Gln Lys Ala Leu Glu Leu Asp Pro
                 20                  25                  30

Arg Ser Ala Glu Ala Trp His Asn Leu Gly His Ala Tyr Tyr Lys Gln
        35                  40                  45

Gly Asp Tyr Asp Glu Ala Ile Glu Tyr Tyr Gln Lys Ala Leu Glu Leu
 50                  55                  60

Asp Pro Arg Ser Ala Glu Ala Trp Tyr Asn Leu Gly Asn Ala Tyr Tyr
 65              70                  75                  80

Lys Gln Gly Asp Tyr Asp Glu Ala Ile Glu Tyr Tyr Gln Lys Ala Leu
                 85                  90                  95

Glu Leu Asp Pro Arg Ser
            100
```

<210> SEQ ID NO 44
<211> LENGTH: 306
<212> TYPE: DNA
<213> ORGANISM: Artificial Sequence
<220> FEATURE:
<223> OTHER INFORMATION: CTPR3 WHW

<400> SEQUENCE: 44

```
gctgaggcat ggtacaacct gggtaacgct tactacaaac agggtgacta cgacgaagct    60
atcgaatact accagaaggc tctcgagctg gacccgagat ccgctgaggc atggcacaac   120
ctgggtcacg cttactacaa acagggtgac tacgacgaag ctatcgaata ctaccagaag   180
gctctcgagc tggacccgag atccgctgag gcatggtaca acctgggtaa cgcttactac   240
aaacagggtg actacgacga agctatcgaa tactaccaga aggctctcga gctggacccg   300
agatct                                                              306
```

<210> SEQ ID NO 45
<211> LENGTH: 136
<212> TYPE: PRT
<213> ORGANISM: Artificial Sequence
<220> FEATURE:
<223> OTHER INFORMATION: CTPR4 WHHW

<400> SEQUENCE: 45

```
Ala Glu Ala Trp Tyr Asn Leu Gly Asn Ala Tyr Tyr Lys Gln Gly Asp
1               5                   10                  15
Tyr Asp Glu Ala Ile Glu Tyr Tyr Gln Lys Ala Leu Glu Leu Asp Pro
            20                  25                  30
Arg Ser Ala Glu Ala Trp His Asn Leu Gly His Ala Tyr Tyr Lys Gln
        35                  40                  45
Gly Asp Tyr Asp Glu Ala Ile Glu Tyr Tyr Gln Lys Ala Leu Glu Leu
    50                  55                  60
Asp Pro Arg Ser Ala Glu Ala Trp His Asn Leu Gly His Ala Tyr Tyr
65                  70                  75                  80
Lys Gln Gly Asp Tyr Asp Glu Ala Ile Glu Tyr Tyr Gln Lys Ala Leu
                85                  90                  95
Glu Leu Asp Pro Arg Ser Ala Glu Ala Trp Tyr Asn Leu Gly Asn Ala
            100                 105                 110
Tyr Tyr Lys Gln Gly Asp Tyr Asp Glu Ala Ile Glu Tyr Tyr Gln Lys
        115                 120                 125
Ala Leu Glu Leu Asp Pro Arg Ser
    130                 135
```

<210> SEQ ID NO 46
<211> LENGTH: 408
<212> TYPE: DNA
<213> ORGANISM: Artificial Sequence
<220> FEATURE:
<223> OTHER INFORMATION: CTPR4 WHHW

<400> SEQUENCE: 46

```
gctgaggcat ggtacaacct gggtaacgct tactacaaac agggtgacta cgacgaagct    60
atcgaatact accagaaggc tctcgagctg gacccgagat ccgctgaggc atggcacaac   120
ctgggtcacg cttactacaa acagggtgac tacgacgaag ctatcgaata ctaccagaag   180
gctctcgagc tggacccgag atccgctgag gcatggcaca acctgggtca cgcttactac   240
aaacagggtg actacgacga agctatcgaa tactaccaga aggctctcga gctggacccg   300
agatccgctg aggcatggta caacctgggt aacgcttact acaaacaggg tgactacgac   360
gaagctatcg aatactacca gaaggctctc gagctggacc cgagatct               408
```

-continued

```
<210> SEQ ID NO 47
<211> LENGTH: 170
<212> TYPE: PRT
<213> ORGANISM: Artificial Sequence
<220> FEATURE:
<223> OTHER INFORMATION: CTPR5 WHHHW

<400> SEQUENCE: 47

Ala Glu Ala Trp Tyr Asn Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser Ala Glu Ala Trp His Asn Leu Gly His Ala Tyr Tyr Lys Gln
        35                  40                  45

Gly Asp Tyr Asp Glu Ala Ile Glu Tyr Tyr Gln Lys Ala Leu Glu Leu
    50                  55                  60

Asp Pro Arg Ser Ala Glu Ala Trp His Asn Leu Gly His Ala Tyr Tyr
65                  70                  75                  80

Lys Gln Gly Asp Tyr Asp Glu Ala Ile Glu Tyr Tyr Gln Lys Ala Leu
                85                  90                  95

Glu Leu Asp Pro Arg Ser Ala Glu Ala Trp His Asn Leu Gly His Ala
            100                 105                 110

Tyr Tyr Lys Gln Gly Asp Tyr Asp Glu Ala Ile Glu Tyr Tyr Gln Lys
        115                 120                 125

Ala Leu Glu Leu Asp Pro Arg Ser Ala Glu Ala Trp Tyr Asn Leu Gly
    130                 135                 140

Asn Ala Tyr Tyr Lys Gln Gly Asp Tyr Asp Glu Ala Ile Glu Tyr Tyr
145                 150                 155                 160

Gln Lys Ala Leu Glu Leu Asp Pro Arg Ser
                165                 170

<210> SEQ ID NO 48
<211> LENGTH: 510
<212> TYPE: DNA
<213> ORGANISM: Artificial Sequence
<220> FEATURE:
<223> OTHER INFORMATION: CTPR5 WHHHW

<400> SEQUENCE: 48
gctgaggcat ggtacaacct gggtaacgct tactacaaac agggtgacta cgacgaagct      60
atcgaatact accagaaggc tctcgagctg acccgagat ccgctgaggc atggcacaac      120
ctgggtcacg cttactacaa acagggtgac tacgacgaag ctatcgaata ctaccagaag      180
gctctcgagc tggacccgag atccgctgag gcatggcaca acctgggtca cgcttactac      240
aaacagggtg actacgacga agctatcgaa tactaccaga aggctctcga gctggacccg      300
agatccgctg aggcatggca caacctgggt cacgcttact acaaacaggg tgactacgac      360
gaagctatcg aatactacca gaaggctctc gagctggacc cgagatccgc tgaggcatgg      420
tacaacctgg gtaacgctta ctacaaacag ggtgactacg acgaagctat cgaatactac      480
cagaaggctc tcgagctgga cccgagatct      510

<210> SEQ ID NO 49
<211> LENGTH: 136
<212> TYPE: PRT
<213> ORGANISM: Artificial Sequence
<220> FEATURE:
<223> OTHER INFORMATION: CTPR4 WCC1W
```

```
<400> SEQUENCE: 49

Ala Glu Ala Trp Tyr Asn Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser Ala Glu Ala Trp Cys Asn Leu Gly Cys Ala Tyr Tyr Lys Gln
        35                  40                  45

Gly Asp Tyr Asp Glu Ala Ile Glu Tyr Tyr Gln Lys Ala Leu Glu Leu
    50                  55                  60

Asp Pro Arg Ser Ala Cys Ala Trp Tyr Cys Leu Gly Asn Ala Tyr Tyr
65                  70                  75                  80

Lys Gln Gly Asp Tyr Asp Glu Ala Ile Glu Tyr Tyr Gln Lys Ala Leu
                85                  90                  95

Glu Leu Asp Pro Arg Ser Ala Glu Ala Trp Tyr Asn Leu Gly Asn Ala
            100                 105                 110

Tyr Tyr Lys Gln Gly Asp Tyr Asp Glu Ala Ile Glu Tyr Tyr Gln Lys
        115                 120                 125

Ala Leu Glu Leu Asp Pro Arg Ser
    130                 135

<210> SEQ ID NO 50
<211> LENGTH: 408
<212> TYPE: DNA
<213> ORGANISM: Artificial Sequence
<220> FEATURE:
<223> OTHER INFORMATION: CTPR4 WCC1W

<400> SEQUENCE: 50
gctgaggcat ggtacaacct gggttacgct tactacaaac agggtgacta cgacgaagct      60
atcgaatact accagaaggc tctcgagctg gacccgagat ccgctgaggc atggtgcaac     120
ctgggttgcg cttactacaa acagggtgac tacgacgaag ctatcgaata ctaccagaag     180
gctctcgagc tggacccgag atccgcttgt catggtact gcctgggtaa cgcttactac     240
aaacagggtg actacgacga agctatcgaa tactaccaga aggctctcga gctggacccg     300
agatccgctg aggcatggta caacctgggt tacgcttact acaaacaggg tgactacgac     360
gaagctatcg aatactacca gaaggctctc gagctggacc cgagatcc                  408

<210> SEQ ID NO 51
<211> LENGTH: 136
<212> TYPE: PRT
<213> ORGANISM: Artificial Sequence
<220> FEATURE:
<223> OTHER INFORMATION: CTPR4 WC1C1W

<400> SEQUENCE: 51

Ala Glu Ala Trp Tyr Asn Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser Ala Cys Ala Trp Tyr Cys Leu Gly Asn Ala Tyr Tyr Lys Gln
        35                  40                  45

Gly Asp Tyr Asp Glu Ala Ile Glu Tyr Tyr Gln Lys Ala Leu Glu Leu
    50                  55                  60

Asp Pro Arg Ser Ala Cys Ala Trp Tyr Cys Leu Gly Asn Ala Tyr Tyr
65                  70                  75                  80
```

```
Lys Gln Gly Asp Tyr Asp Glu Ala Ile Glu Tyr Tyr Gln Lys Ala Leu
                85                  90                  95

Glu Leu Asp Pro Arg Ser Ala Glu Ala Trp Tyr Asn Leu Gly Asn Ala
                100                 105                 110

Tyr Tyr Lys Gln Gly Asp Tyr Asp Glu Ala Ile Glu Tyr Tyr Gln Lys
            115                 120                 125

Ala Leu Glu Leu Asp Pro Arg Ser
        130                 135

<210> SEQ ID NO 52
<211> LENGTH: 408
<212> TYPE: DNA
<213> ORGANISM: Artificial Sequence
<220> FEATURE:
<223> OTHER INFORMATION: CTPR4 WC1C1W

<400> SEQUENCE: 52
gctgaggcat ggtacaacct gggttacgct tactacaaac agggtgacta cgacgaagct    60
atcgaatact accagaaggc tctcgagctg gacccgagat ccgcttgtgc atggtactgc   120
ctgggtaacg cttactacaa acagggtgac tacgacgaag ctatcgaata ctaccagaag   180
gctctcgagc tggacccgag atccgcttgt gcatggtact gcctgggtaa cgcttactac   240
aaacagggtg actacgacga agctatcgaa tactaccaga aggctctcga gctggacccg   300
agatccgctg aggcatggta caacctgggt tacgcttact acaaacaggg tgactacgac   360
gaagctatcg aatactacca gaaggctctc gagctggacc cgagatcc              408

<210> SEQ ID NO 53
<211> LENGTH: 136
<212> TYPE: PRT
<213> ORGANISM: Artificial Sequence
<220> FEATURE:
<223> OTHER INFORMATION: CTPR4 WC2C2W

<400> SEQUENCE: 53

Ala Glu Ala Trp Tyr Asn Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser Ala Cys Ala Trp Tyr Cys Leu Gly Cys Ala Tyr Tyr Lys Gln
        35                  40                  45

Gly Asp Tyr Asp Glu Ala Ile Glu Tyr Tyr Gln Lys Ala Leu Glu Leu
    50                  55                  60

Asp Pro Arg Ser Ala Cys Ala Trp Tyr Cys Leu Gly Cys Ala Tyr Tyr
65                  70                  75                  80

Lys Gln Gly Asp Tyr Asp Glu Ala Ile Glu Tyr Tyr Gln Lys Ala Leu
                85                  90                  95

Glu Leu Asp Pro Arg Ser Ala Glu Ala Trp Tyr Asn Leu Gly Asn Ala
                100                 105                 110

Tyr Tyr Lys Gln Gly Asp Tyr Asp Glu Ala Ile Glu Tyr Tyr Gln Lys
            115                 120                 125

Ala Leu Glu Leu Asp Pro Arg Ser
        130                 135

<210> SEQ ID NO 54
<211> LENGTH: 408
<212> TYPE: DNA
<213> ORGANISM: Artificial Sequence
```

<220> FEATURE:
<223> OTHER INFORMATION: CTPR4 WC2C2W

<400> SEQUENCE: 54

```
gctgaggcat ggtacaacct gggttacgct tactacaaac agggtgacta cgacgaagct    60
atcgaatact accagaaggc tctcgagctg acccgagat  ccgcttgtgc atggtactgc   120
ctgggttgcg cttactacaa acagggtgac tacgacgaag ctatcgaata ctaccagaag   180
gctctcgagc tggacccgag atccgcttgt gcatggtact gcctgggttg cgcttactac   240
aaacagggtg actacgacga agctatcgaa tactaccaga aggctctcga gctggacccg   300
agatccgctg aggcatggta caacctgggt tacgcttact acaaacaggg tgactacgac   360
gaagctatcg aatactacca gaaggctctc gagctggacc cgagatcc              408
```

<210> SEQ ID NO 55
<211> LENGTH: 136
<212> TYPE: PRT
<213> ORGANISM: Artificial Sequence
<220> FEATURE:
<223> OTHER INFORMATION: CTPR4 WC3C3W

<400> SEQUENCE: 55

```
Ala Glu Ala Trp Tyr Asn Leu Gly Asn Ala Tyr Tyr Lys Gln Gly Asp
1               5                  10                  15

Tyr Asp Glu Ala Ile Glu Tyr Tyr Gln Lys Ala Leu Glu Leu Asp Pro
            20                  25                  30

Arg Ser Ala Cys Ala Trp Tyr Cys Leu Gly Cys Ala Tyr Leu Cys Gln
        35                  40                  45

Gly Asp Tyr Asp Glu Ala Ile Glu Tyr Tyr Gln Lys Ala Leu Glu Leu
    50                  55                  60

Asp Pro Arg Ser Ala Cys Ala Trp Tyr Cys Leu Gly Cys Ala Tyr Leu
65                  70                  75                  80

Cys Gln Gly Asp Tyr Asp Glu Ala Ile Glu Tyr Tyr Gln Lys Ala Leu
                85                  90                  95

Glu Leu Asp Pro Arg Ser Ala Glu Ala Trp Tyr Asn Leu Gly Asn Ala
            100                 105                 110

Tyr Tyr Lys Gln Gly Asp Tyr Asp Glu Ala Ile Glu Tyr Tyr Gln Lys
        115                 120                 125

Ala Leu Glu Leu Asp Pro Arg Ser
    130                 135
```

<210> SEQ ID NO 56
<211> LENGTH: 408
<212> TYPE: DNA
<213> ORGANISM: Artificial Sequence
<220> FEATURE:
<223> OTHER INFORMATION: CTPR4 WC3C3W

<400> SEQUENCE: 56

```
gctgaggcat ggtacaacct gggttacgct tactacaaac agggtgacta cgacgaagct    60
atcgaatact accagaaggc tctcgagctg acccgagat  ccgcttgtgc atggtactgc   120
ctgggttgcg cttacctctg ccagggtgac tacgacgaag ctatcgaata ctaccagaag   180
gctctcgagc tggacccgag atctgcttgt gcatggtact gcctgggttg cgcttacctc   240
tgccagggtg actacgacga agctatcgaa tactaccaga aggctctcga gctggacccg   300
agatctgctg aggcatggta caacctgggt tacgcttact acaaacaggg tgactacgac   360
gaagctatcg aatactacca gaaggctctc gagctggacc cgagatcc              408
```

<210> SEQ ID NO 57
<211> LENGTH: 170
<212> TYPE: PRT
<213> ORGANISM: Artificial Sequence
<220> FEATURE:
<223> OTHER INFORMATION: CTPR5 WC1C1C1W

<400> SEQUENCE: 57

```
Ala Glu Ala Trp Tyr Asn Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser Ala Cys Ala Trp Tyr Cys Leu Gly Asn Ala Tyr Tyr Lys Gln
        35                  40                  45

Gly Asp Tyr Asp Glu Ala Ile Glu Tyr Tyr Gln Lys Ala Leu Glu Leu
    50                  55                  60

Asp Pro Arg Ser Ala Cys Ala Trp Tyr Cys Leu Gly Asn Ala Tyr Tyr
65                  70                  75                  80

Lys Gln Gly Asp Tyr Asp Glu Ala Ile Glu Tyr Tyr Gln Lys Ala Leu
                85                  90                  95

Glu Leu Asp Pro Arg Ser Ala Cys Ala Trp Tyr Cys Leu Gly Asn Ala
            100                 105                 110

Tyr Tyr Lys Gln Gly Asp Tyr Asp Glu Ala Ile Glu Tyr Tyr Gln Lys
        115                 120                 125

Ala Leu Glu Leu Asp Pro Arg Ser Ala Glu Ala Trp Tyr Asn Leu Gly
    130                 135                 140

Asn Ala Tyr Tyr Lys Gln Gly Asp Tyr Asp Glu Ala Ile Glu Tyr Tyr
145                 150                 155                 160

Gln Lys Ala Leu Glu Leu Asp Pro Arg Ser
                165                 170
```

<210> SEQ ID NO 58
<211> LENGTH: 510
<212> TYPE: DNA
<213> ORGANISM: Artificial Sequence
<220> FEATURE:
<223> OTHER INFORMATION: CTPR5 WC1C1C1W

<400> SEQUENCE: 58

```
gctgaggcat ggtacaacct gggttacgct tactacaaac agggtgacta cgacgaagct        60
atcgaatact accagaaggc tctcgagctg acccgagat ccgcttgtgc atggtactgc       120
ctgggtaacg cttactacaa acagggtgac tacgacgaag ctatcgaata ctaccagaag       180
gctctcgagc tggacccgag atccgcttgt gcatggtact gcctgggtaa cgcttactac       240
aaacagggtg actacgacga agctatcgaa tactaccaga aggctctcga gctggacccg       300
agatccgctt gtgcatggta ctgcctgggt aacgcttact acaaacaggg tgactacgac       360
gaagctatcg aatactacca gaaggctctc gagctggacc cgagatccgc tgaggcatgg       420
tacaacctgg gttacgctta ctacaaacag ggtgactacg acgaagctat cgaatactac       480
cagaaggctc tcgagctgga cccgagatcc                                         510
```

<210> SEQ ID NO 59
<211> LENGTH: 170
<212> TYPE: PRT
<213> ORGANISM: Artificial Sequence
<220> FEATURE:
<223> OTHER INFORMATION: CTPR5 WC2C2C2W

<400> SEQUENCE: 59

Ala Glu Ala Trp Tyr Asn Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser Ala Cys Ala Trp Tyr Cys Leu Gly Cys Ala Tyr Tyr Lys Gln
        35                  40                  45

Gly Asp Tyr Asp Glu Ala Ile Glu Tyr Tyr Gln Lys Ala Leu Glu Leu
    50                  55                  60

Asp Pro Arg Ser Ala Cys Ala Trp Tyr Cys Leu Gly Cys Ala Tyr Tyr
65                  70                  75                  80

Lys Gln Gly Asp Tyr Asp Glu Ala Ile Glu Tyr Tyr Gln Lys Ala Leu
                85                  90                  95

Glu Leu Asp Pro Arg Ser Ala Cys Ala Trp Tyr Cys Leu Gly Cys Ala
            100                 105                 110

Tyr Tyr Lys Gln Gly Asp Tyr Asp Glu Ala Ile Glu Tyr Tyr Gln Lys
        115                 120                 125

Ala Leu Glu Leu Asp Pro Arg Ser Ala Glu Ala Trp Tyr Asn Leu Gly
    130                 135                 140

Asn Ala Tyr Tyr Lys Gln Gly Asp Tyr Asp Glu Ala Ile Glu Tyr Tyr
145                 150                 155                 160

Gln Lys Ala Leu Glu Leu Asp Pro Arg Ser
                165                 170

<210> SEQ ID NO 60
<211> LENGTH: 510
<212> TYPE: DNA
<213> ORGANISM: Artificial Sequence
<220> FEATURE:
<223> OTHER INFORMATION: CTPR5 WC2C2C2W

<400> SEQUENCE: 60
gctgaggcat ggtacaacct gggttacgct tactacaaac agggtgacta cgacgaagct        60
atcgaatact accagaaggc tctcgagctg gacccgagat ccgcttgtgc atggtactgc       120
ctgggttgcg cttactacaa acagggtgac tacgacgaag ctatcgaata ctaccagaag       180
gctctcgagc tggacccgag atccgcttgt gcatggtact gcctgggttg cgcttactac       240
aaacagggtg actacgacga agctatcgaa tactaccaga aggctctcga gctggacccg       300
agatccgctt gtgcatggta ctgcctgggt tgcgcttact acaaacaggg tgactacgac       360
gaagctatcg aatactacca gaaggctctc gagctggacc cgagatccgc tgaggcatgg       420
tacaacctgg gttacgctta ctacaaacag ggtgactacg acgaagctat cgaatactac       480
cagaaggctc tcgagctgga cccgagatcc                                       510

<210> SEQ ID NO 61
<211> LENGTH: 170
<212> TYPE: PRT
<213> ORGANISM: Artificial Sequence
<220> FEATURE:
<223> OTHER INFORMATION: CTPR5 WC3C3C3W

<400> SEQUENCE: 61

Ala Glu Ala Trp Tyr Asn Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser Ala Cys Ala Trp Tyr Cys Leu Gly Cys Ala Tyr Leu Cys Gln
            35                  40                  45

Gly Asp Tyr Asp Glu Ala Ile Glu Tyr Tyr Lys Ala Leu Glu Leu
 50                  55                  60

Asp Pro Arg Ser Ala Cys Ala Trp Tyr Cys Leu Gly Cys Ala Tyr Leu
65                   70                  75                  80

Cys Gln Gly Asp Tyr Asp Glu Ala Ile Glu Tyr Tyr Gln Lys Ala Leu
                85                  90                  95

Glu Leu Asp Pro Arg Ser Ala Cys Ala Trp Tyr Cys Leu Gly Cys Ala
            100                 105                 110

Tyr Leu Cys Gln Gly Asp Tyr Asp Glu Ala Ile Glu Tyr Tyr Gln Lys
            115                 120                 125

Ala Leu Glu Leu Asp Pro Arg Ser Ala Glu Ala Trp Tyr Asn Leu Gly
            130                 135                 140

Asn Ala Tyr Tyr Lys Gln Gly Asp Tyr Asp Glu Ala Ile Glu Tyr Tyr
145                 150                 155                 160

Gln Lys Ala Leu Glu Leu Asp Pro Arg Ser
                165                 170

<210> SEQ ID NO 62
<211> LENGTH: 510
<212> TYPE: DNA
<213> ORGANISM: Artificial Sequence
<220> FEATURE:
<223> OTHER INFORMATION: CTPR5 WC3C3C3W

<400> SEQUENCE: 62
gctgaggcat ggtacaacct gggttacgct tactacaaac agggtgacta cgacgaagct    60
atcgaatact accagaaggc tctcgagctg gacccgagat ccgcttgtgc atggtactgc   120
ctgggttgcg cttacctctg ccagggtgac tacgacgaag ctatcgaata ctaccagaag   180
gctctcgagc tggacccgag atctgcttgt gcatggtact gcctgggttg cgcttacctc   240
tgccagggtg actacgacga agctatcgaa tactaccaga aggctctcga gctggacccg   300
agatctgctt gtgcatggta ctgcctgggt tgcgcttacc tctgccaggg tgactacgac   360
gaagctatcg aatactacca gaaggctctc gagctggacc cgagatctgc tgaggcatgg   420
tacaacctgg gttacgctta ctacaaacag ggtgactacg acgaagctat cgaatactac   480
cagaaggctc tcgagctgga cccgagatcc                                    510

<210> SEQ ID NO 63
<211> LENGTH: 204
<212> TYPE: PRT
<213> ORGANISM: Artificial Sequence
<220> FEATURE:
<223> OTHER INFORMATION: CTPR6 WC3C3C3C3W

<400> SEQUENCE: 63

Ala Glu Ala Trp Tyr Asn Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser Ala Cys Ala Trp Tyr Cys Leu Gly Cys Ala Tyr Leu Cys Gln
            35                  40                  45

Gly Asp Tyr Asp Glu Ala Ile Glu Tyr Tyr Gln Lys Ala Leu Glu Leu
 50                  55                  60

Asp Pro Arg Ser Ala Cys Ala Trp Tyr Cys Leu Gly Cys Ala Tyr Leu
65                  70                  75                  80

Cys Gln Gly Asp Tyr Asp Glu Ala Ile Glu Tyr Tyr Gln Lys Ala Leu
                85                  90                  95

Glu Leu Asp Pro Arg Ser Ala Cys Ala Trp Tyr Cys Leu Gly Cys Ala
            100                 105                 110

Tyr Leu Cys Gln Gly Asp Tyr Asp Glu Ala Ile Glu Tyr Tyr Gln Lys
        115                 120                 125

Ala Leu Glu Leu Asp Pro Arg Ser Ala Cys Ala Trp Tyr Cys Leu Gly
    130                 135                 140

Cys Ala Tyr Leu Cys Gln Gly Asp Tyr Asp Glu Ala Ile Glu Tyr Tyr
145                 150                 155                 160

Gln Lys Ala Leu Glu Leu Asp Pro Arg Ser Ala Glu Ala Trp Tyr Asn
                165                 170                 175

Leu Gly Asn Ala Tyr Tyr Lys Gln Gly Asp Tyr Asp Glu Ala Ile Glu
                180                 185                 190

Tyr Tyr Gln Lys Ala Leu Glu Leu Asp Pro Arg Ser
                195                 200

<210> SEQ ID NO 64
<211> LENGTH: 612
<212> TYPE: DNA
<213> ORGANISM: Artificial Sequence
<220> FEATURE:
<223> OTHER INFORMATION: CTPR6 WC3C3C3C3W

<400> SEQUENCE: 64
gctgaggcat ggtacaacct gggttacgct tactacaaac agggtgacta cgacgaagct      60
atcgaatact accagaaggc tctcgagctg acccgagat ccgcttgtgc atggtactgc      120
ctgggttgcg cttacctctg ccagggtgac tacgacgaag ctatcgaata ctaccagaag     180
gctctcgagc tggacccgag atctgcttgt gcatggtact gcctgggttg cgcttacctc     240
tgccagggtg actacgacga agctatcgaa tactaccaga aggctctcga gctggacccg     300
agatctgctt gtgcatggta ctgcctgggt tgcgcttacc tctgccaggg tgactacgac     360
gaagctatcg aatactacca gaaggctctc gagctggacc cgagatctgc ttgtgcatgg     420
tactgcctgg gttgcgctta cctctgccag ggtgactacg acgaagctat cgaatactac     480
cagaaggctc tcgagctgga cccgagatct gctgaggcat ggtacaacct gggttacgct     540
tactacaaac agggtgacta cgacgaagct atcgaatact accagaaggc tctcgagctg     600
gacccgagat cc                                                         612

<210> SEQ ID NO 65
<211> LENGTH: 238
<212> TYPE: PRT
<213> ORGANISM: Artificial Sequence
<220> FEATURE:
<223> OTHER INFORMATION: CTPR7 WC3C3C3C3W

<400> SEQUENCE: 65

Ala Glu Ala Trp Tyr Asn Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser Ala Cys Ala Trp Tyr Cys Leu Gly Cys Ala Tyr Leu Cys Gln
        35                  40                  45

Gly Asp Tyr Asp Glu Ala Ile Glu Tyr Tyr Gln Lys Ala Leu Glu Leu
    50                  55                  60

Asp Pro Arg Ser Ala Cys Ala Trp Tyr Cys Leu Gly Cys Ala Tyr Leu
65                  70                  75                  80

Cys Gln Gly Asp Tyr Asp Glu Ala Ile Glu Tyr Tyr Gln Lys Ala Leu
                85                  90                  95

Glu Leu Asp Pro Arg Ser Ala Cys Ala Trp Tyr Cys Leu Gly Cys Ala
            100                 105                 110

Tyr Leu Cys Gln Gly Asp Tyr Asp Glu Ala Ile Glu Tyr Tyr Gln Lys
        115                 120                 125

Ala Leu Glu Leu Asp Pro Arg Ser Ala Cys Ala Trp Tyr Cys Leu Gly
    130                 135                 140

Cys Ala Tyr Leu Cys Gln Gly Asp Tyr Asp Glu Ala Ile Glu Tyr Tyr
145                 150                 155                 160

Gln Lys Ala Leu Glu Leu Asp Pro Arg Ser Ala Cys Ala Trp Tyr Cys
                165                 170                 175

Leu Gly Cys Ala Tyr Leu Cys Gln Gly Asp Tyr Asp Glu Ala Ile Glu
            180                 185                 190

Tyr Tyr Gln Lys Ala Leu Glu Leu Asp Pro Arg Ser Ala Glu Ala Trp
        195                 200                 205

Tyr Asn Leu Gly Asn Ala Tyr Tyr Lys Gln Gly Asp Tyr Asp Glu Ala
    210                 215                 220

Ile Glu Tyr Tyr Gln Lys Ala Leu Glu Leu Asp Pro Arg Ser
225                 230                 235

<210> SEQ ID NO 66
<211> LENGTH: 714
<212> TYPE: DNA
<213> ORGANISM: Artificial Sequence
<220> FEATURE:
<223> OTHER INFORMATION: CTPR7 WC3C3C3C3W

<400> SEQUENCE: 66
gctgaggcat ggtacaacct gggttacgct tactacaaac agggtgacta cgacgaagct      60
atcgaatact accagaaggc tctcgagctg gacccgagat ccgcttgtgc atggtactgc     120
ctgggttgcg cttacctctg ccagggtgac tacgacgaag ctatcgaata ctaccagaag     180
gctctcgagc tggacccgag atctgcttgt gcatggtact gcctgggttg cgcttacctc     240
tgccagggtg actacgacga agctatcgaa tactaccaga aggctctcga gctggacccg     300
agatctgctt gtgcatggta ctgcctgggt tgcgcttacc tctgccaggg tgactacgac     360
gaagctatcg aatactacca gaaggctctc gagctggacc cgagatctgc ttgtgcatgg     420
tactgcctgg gttgcgctta cctctgccag ggtgactacg acgaagctat cgaatactac     480
cagaaggctc tcgagctgga cccgagatct gcttgtgcat ggtactgcct gggttgcgct     540
tacctctgcc agggtgacta cgacgaagct atcgaatact accagaaggc tctcgagctg     600
gacccgagat ctgctgaggc atggtacaac ctgggttacg cttactacaa acagggtgac     660
tacgacgaag ctatcgaata ctaccagaag gctctcgagc tggacccgag atcc          714

<210> SEQ ID NO 67
<211> LENGTH: 272
<212> TYPE: PRT
<213> ORGANISM: Artificial Sequence
<220> FEATURE:
<223> OTHER INFORMATION: CTPR8 WC3C3C3C3C3W

<400> SEQUENCE: 67

Ala Glu Ala Trp Tyr Asn Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser Ala Cys Ala Trp Tyr Cys Leu Gly Cys Ala Tyr Leu Cys Gln
        35                  40                  45

Gly Asp Tyr Asp Glu Ala Ile Glu Tyr Tyr Gln Lys Ala Leu Glu Leu
    50                  55                  60

Asp Pro Arg Ser Ala Cys Ala Trp Tyr Cys Leu Gly Cys Ala Tyr Leu
65                  70                  75                  80

Cys Gln Gly Asp Tyr Asp Glu Ala Ile Glu Tyr Tyr Gln Lys Ala Leu
                85                  90                  95

Glu Leu Asp Pro Arg Ser Ala Cys Ala Trp Tyr Cys Leu Gly Cys Ala
            100                 105                 110

Tyr Leu Cys Gln Gly Asp Tyr Asp Glu Ala Ile Glu Tyr Tyr Gln Lys
        115                 120                 125

Ala Leu Glu Leu Asp Pro Arg Ser Ala Cys Ala Trp Tyr Cys Leu Gly
    130                 135                 140

Cys Ala Tyr Leu Cys Gln Gly Asp Tyr Asp Glu Ala Ile Glu Tyr Tyr
145                 150                 155                 160

Gln Lys Ala Leu Glu Leu Asp Pro Arg Ser Ala Cys Ala Trp Tyr Cys
                165                 170                 175

Leu Gly Cys Ala Tyr Leu Cys Gln Gly Asp Tyr Asp Glu Ala Ile Glu
            180                 185                 190

Tyr Tyr Gln Lys Ala Leu Glu Leu Asp Pro Arg Ser Ala Cys Ala Trp
        195                 200                 205

Tyr Cys Leu Gly Cys Ala Tyr Leu Cys Gln Gly Asp Tyr Asp Glu Ala
    210                 215                 220

Ile Glu Tyr Tyr Gln Lys Ala Leu Glu Leu Asp Pro Arg Ser Ala Glu
225                 230                 235                 240

Ala Trp Tyr Asn Leu Gly Asn Ala Tyr Tyr Lys Gln Gly Asp Tyr Asp
                245                 250                 255

Glu Ala Ile Glu Tyr Tyr Gln Lys Ala Leu Glu Leu Asp Pro Arg Ser
            260                 265                 270

<210> SEQ ID NO 68
<211> LENGTH: 816
<212> TYPE: DNA
<213> ORGANISM: Artificial Sequence
<220> FEATURE:
<223> OTHER INFORMATION: CTPR8 WC3C3C3C3C3W

<400> SEQUENCE: 68
gctgaggcat ggtacaacct gggttacgct tactacaaac agggtgacta cgacgaagct    60
atcgaatact accagaaggc tctcgagctg acccgagat ccgcttgtgc atggtactgc    120
ctgggttgcg cttacctctg ccagggtgac tacgacgaag ctatcgaata ctaccagaag    180
gctctcgagc tggacccgag atctgcttgt gcatggtact gcctgggttg cgcttacctc    240
tgccagggtg actacgacga agctatcgaa tactaccaga aggctctcga gctggacccg    300
agatctgctt gtgcatggta ctgcctgggt tgcgcttacc tctgccaggg tgactacgac    360
gaagctatcg aatactacca gaaggctctc gagctggacc cgagatctgc ttgtgcatgg    420
tactgcctgg gttgcgctta cctctgccag ggtgactacg acgaagctat cgaatactac    480

-continued

```
cagaaggctc tcgagctgga cccgagatct gcttgtgcat ggtactgcct gggttgcgct    540
tacctctgcc aggtgactac gacgaagct atcgaatact accagaaggc tctcgagctg    600
gacccgagat ctgcttgtgc atggtactgc ctgggttgcg cttacctctg ccagggtgac    660
tacgacgaag ctatcgaata ctaccagaag gctctcgagc tggacccgag atctgctgag    720
gcatggtaca acctgggtta cgcttactac aaacagggtg actacgacga agctatcgaa    780
tactaccaga aggctctcga gctggacccg agatcc                              816
```

<210> SEQ ID NO 69
<211> LENGTH: 5
<212> TYPE: PRT
<213> ORGANISM: Artificial Sequence
<220> FEATURE:
<223> OTHER INFORMATION: N terminal end for CTPR protein

<400> SEQUENCE: 69

Gly Ala Met Gly Ser
1               5

<210> SEQ ID NO 70
<211> LENGTH: 15
<212> TYPE: PRT
<213> ORGANISM: Artificial Sequence
<220> FEATURE:
<223> OTHER INFORMATION: C terminal end for CTPR protein

<400> SEQUENCE: 70

Ala Glu Ala Lys Gln Asn Leu Gly Asn Ala Lys Gln Lys Gln Gly
1               5                   10                  15

<210> SEQ ID NO 71
<211> LENGTH: 7
<212> TYPE: PRT
<213> ORGANISM: Artificial Sequence
<220> FEATURE:
<223> OTHER INFORMATION: NLS SV40 large T antigen

<400> SEQUENCE: 71

Pro Lys Lys Lys Arg Lys Val
1               5

<210> SEQ ID NO 72
<211> LENGTH: 16
<212> TYPE: PRT
<213> ORGANISM: Artificial Sequence
<220> FEATURE:
<223> OTHER INFORMATION: NLS nucleoplasmin sequence

<400> SEQUENCE: 72

Lys Arg Pro Ala Ala Thr Lys Lys Ala Gly Gln Ala Lys Lys Lys Lys
1               5                   10                  15

<210> SEQ ID NO 73
<211> LENGTH: 20
<212> TYPE: PRT
<213> ORGANISM: Artificial Sequence
<220> FEATURE:
<223> OTHER INFORMATION: NLS nucleoplasmin sequence

<400> SEQUENCE: 73

Ala Val Lys Arg Pro Ala Ala Thr Lys Lys Ala Gly Gln Ala Lys Lys
1               5                   10                  15

Lys Lys Leu Asp
            20

```
<210> SEQ ID NO 74
<211> LENGTH: 25
<212> TYPE: PRT
<213> ORGANISM: Artificial Sequence
<220> FEATURE:
<223> OTHER INFORMATION: NLS EGL-13

<400> SEQUENCE: 74

Met Ser Arg Arg Arg Lys Ala Asn Pro Thr Lys Leu Ser Glu Asn Ala
1               5                   10                  15

Lys Lys Leu Ala Lys Glu Val Glu Asn
            20                  25

<210> SEQ ID NO 75
<211> LENGTH: 9
<212> TYPE: PRT
<213> ORGANISM: Artificial Sequence
<220> FEATURE:
<223> OTHER INFORMATION: NLS c-Myc

<400> SEQUENCE: 75

Pro Ala Ala Lys Arg Val Lys Leu Asp
1               5

<210> SEQ ID NO 76
<211> LENGTH: 9
<212> TYPE: PRT
<213> ORGANISM: Artificial Sequence
<220> FEATURE:
<223> OTHER INFORMATION: NLS TUS

<400> SEQUENCE: 76

Lys Leu Lys Ile Lys Arg Pro Val Lys
1               5

<210> SEQ ID NO 77
<211> LENGTH: 4
<212> TYPE: PRT
<213> ORGANISM: Artificial Sequence
<220> FEATURE:
<223> OTHER INFORMATION: endoplasmic reticulum localization signal

<400> SEQUENCE: 77

Lys Glu Asp Leu
1

<210> SEQ ID NO 78
<211> LENGTH: 25
<212> TYPE: PRT
<213> ORGANISM: Artificial Sequence
<220> FEATURE:
<223> OTHER INFORMATION: mitochondrial localization signal

<400> SEQUENCE: 78

Met Leu Ser Leu Arg Gln Ser Ile Arg Phe Phe Lys Pro Arg Thr Arg
1               5                   10                  15

Thr Leu Cys Ser Ser Arg Tyr Leu Leu
            20                  25

<210> SEQ ID NO 79
<211> LENGTH: 124
<212> TYPE: PRT
<213> ORGANISM: Artificial Sequence
<220> FEATURE:
<223> OTHER INFORMATION: CTPR3 NLS-WHW
```

<400> SEQUENCE: 79

Pro Lys Lys Lys Arg Lys Val Ala Glu Ala Trp Tyr Asn Leu Gly Asn
1               5                   10                  15

Ala Tyr Tyr Lys Gln Gly Asp Tyr Asp Glu Ala Ile Glu Tyr Tyr Gln
            20                  25                  30

Lys Ala Leu Glu Leu Asp Pro Arg Ser Ala Glu Ala Trp His Asn Leu
        35                  40                  45

Gly His Ala Tyr Tyr Lys Gln Gly Asp Tyr Asp Glu Ala Ile Glu Tyr
    50                  55                  60

Tyr Gln Lys Ala Leu Glu Leu Asp Pro Arg Ser Ala Glu Ala Trp Tyr
65                  70                  75                  80

Asn Leu Gly Asn Ala Tyr Tyr Lys Gln Gly Asp Tyr Asp Glu Ala Ile
                85                  90                  95

Glu Tyr Tyr Gln Lys Ala Leu Glu Leu Asp Pro Arg Ser Ala Glu Ala
            100                 105                 110

Lys Gln Asn Leu Gly Asn Ala Lys Gln Lys Gln Gly
        115                 120

<210> SEQ ID NO 80
<211> LENGTH: 327
<212> TYPE: DNA
<213> ORGANISM: Artificial Sequence
<220> FEATURE:
<223> OTHER INFORMATION: CTPR3 NLS-WHW

<400> SEQUENCE: 80

```
ccgaagaaaa agcggaaggt ggctgaggca tggtacaacc tgggtaacgc ttactacaaa      60
cagggtgact acgacgaagc tatcgaatac taccagaagg ctctcgagct ggacccgaga     120
tccgctgagg catggcacaa cctgggtcac gcttactaca aacagggtga ctacgacgaa     180
gctatcgaat actaccagaa ggctctcgag ctggaccgga tccgctgagg catggtac      240
aacctgggta cgcttactca caacagggt gactacgacg aagctatcga atactaccag     300
aaggctctcg agctggaccc gagatct                                         327
```

<210> SEQ ID NO 81
<211> LENGTH: 5
<212> TYPE: PRT
<213> ORGANISM: Artificial Sequence
<220> FEATURE:
<223> OTHER INFORMATION: tag sequence

<400> SEQUENCE: 81

Met Glu Glu Val Phe
1               5

<210> SEQ ID NO 82
<211> LENGTH: 117
<212> TYPE: PRT
<213> ORGANISM: Artificial Sequence
<220> FEATURE:
<223> OTHER INFORMATION: CTPR3 consensus protein

<400> SEQUENCE: 82

Ala Glu Ala Trp Tyr Asn Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser Ala Glu Ala Trp Tyr Asn Leu Gly Asn Ala Tyr Tyr Lys Gln
        35                  40                  45

Gly Asp Tyr Asp Glu Ala Ile Glu Tyr Tyr Gln Lys Ala Leu Glu Leu
            50                  55                  60

Asp Pro Arg Ser Ala Glu Ala Trp Tyr Asn Leu Gly Asn Ala Tyr Tyr
65                  70                  75                  80

Lys Gln Gly Asp Tyr Asp Glu Ala Ile Glu Tyr Tyr Gln Lys Ala Leu
                85                  90                  95

Glu Leu Asp Pro Arg Ser Ala Glu Ala Lys Gln Asn Leu Gly Asn Ala
            100                 105                 110

Lys Gln Lys Gln Gly
        115

<210> SEQ ID NO 83
<211> LENGTH: 117
<212> TYPE: PRT
<213> ORGANISM: Artificial Sequence
<220> FEATURE:
<223> OTHER INFORMATION: CTPR390 recognition domain

<400> SEQUENCE: 83

Ala Glu Ala Trp Lys Asn Leu Gly Asn Ala Tyr Tyr Lys Gln Gly Asp
1               5                   10                  15

Tyr Gln Lys Ala Ile Glu Tyr Tyr Gln Lys Ala Leu Glu Leu Asp Pro
                20                  25                  30

Asn Asn Ala Ser Ala Trp Tyr Asn Leu Gly Asn Ala Tyr Tyr Lys Gln
            35                  40                  45

Gly Asp Tyr Gln Lys Ala Ile Glu Tyr Tyr Gln Lys Ala Leu Glu Leu
        50                  55                  60

Asp Pro Asn Asn Ala Lys Ala Trp Tyr Arg Arg Gly Asn Ala Tyr Tyr
65                  70                  75                  80

Lys Gln Gly Asp Tyr Gln Lys Ala Ile Glu Asp Tyr Gln Lys Ala Leu
                85                  90                  95

Glu Leu Asp Pro Asn Asn Ala Lys Ala Lys Gln Asn Leu Gly Asn Ala
            100                 105                 110

Lys Gln Lys Gln Gly
        115

<210> SEQ ID NO 84
<211> LENGTH: 115
<212> TYPE: PRT
<213> ORGANISM: Artificial Sequence
<220> FEATURE:
<223> OTHER INFORMATION: TPR1 recognition domain

<400> SEQUENCE: 84

Met Glu Gln Val Asn Glu Leu Lys Glu Lys Gly Asn Lys Ala Leu Ser
1               5                   10                  15

Val Gly Asn Ile Asp Asp Ala Leu Gln Cys Tyr Ser Glu Ala Ile Lys
                20                  25                  30

Leu Asp Pro His Asn His Val Leu Tyr Ser Asn Arg Ser Ala Ala Tyr
            35                  40                  45

Ala Lys Lys Gly Asp Tyr Gln Lys Ala Tyr Glu Asp Gly Cys Lys Thr
        50                  55                  60

Val Asp Leu Lys Pro Asp Trp Gly Lys Gly Tyr Ser Arg Lys Ala Ala
65                  70                  75                  80

Ala Leu Glu Phe Leu Asn Arg Phe Glu Glu Ala Lys Arg Thr Tyr Glu
                85                  90                  95

Glu Gly Leu Lys His Glu Ala Asn Asn Pro Gln Leu Lys Glu Gly Leu
                100                 105                 110

Gln Asn Met
        115

<210> SEQ ID NO 85
<211> LENGTH: 127
<212> TYPE: PRT
<213> ORGANISM: Artificial Sequence
<220> FEATURE:
<223> OTHER INFORMATION: TPR2A recognition domain

<400> SEQUENCE: 85

Lys Gln Ala Leu Lys Glu Lys Glu Leu Gly Asn Asp Ala Tyr Lys Lys
1               5                   10                  15

Lys Asp Phe Asp Thr Ala Leu Lys His Tyr Asp Lys Ala Lys Glu Leu
            20                  25                  30

Asp Pro Thr Asn Met Thr Tyr Ile Thr Asn Gln Ala Ala Val Tyr Phe
        35                  40                  45

Glu Lys Gly Asp Tyr Asn Lys Cys Arg Glu Leu Cys Glu Lys Ala Ile
    50                  55                  60

Glu Val Gly Arg Glu Asn Arg Glu Asp Tyr Arg Gln Ile Ala Lys Ala
65                  70                  75                  80

Tyr Ala Arg Ile Gly Asn Ser Tyr Phe Lys Glu Glu Lys Tyr Lys Asp
                85                  90                  95

Ala Ile His Phe Tyr Asn Lys Ser Leu Ala Glu His Arg Thr Pro Asp
            100                 105                 110

Val Leu Lys Lys Cys Gln Gln Ala Glu Lys Ile Leu Lys Glu Gln
        115                 120                 125

<210> SEQ ID NO 86
<211> LENGTH: 120
<212> TYPE: PRT
<213> ORGANISM: Artificial Sequence
<220> FEATURE:
<223> OTHER INFORMATION: UBP recognition domain

<400> SEQUENCE: 86

Ala Glu Ala Glu Arg Leu Lys Thr Glu Gly Asn Glu Gln Met Lys Val
1               5                   10                  15

Glu Asn Phe Glu Ala Ala Val His Phe Tyr Gly Lys Ala Ile Glu Leu
            20                  25                  30

Asn Pro Ala Asn Ala Val Tyr Phe Cys Asn Arg Ala Ala Ala Tyr Ser
        35                  40                  45

Lys Leu Gly Asn Tyr Ala Gly Ala Val Gln Asp Cys Glu Arg Ala Ile
    50                  55                  60

Cys Ile Asp Pro Ala Tyr Ser Lys Ala Tyr Gly Arg Met Gly Leu Ala
65                  70                  75                  80

Leu Ser Ser Leu Asn Lys His Val Glu Ala Val Ala Tyr Tyr Lys Lys
                85                  90                  95

Ala Leu Glu Leu Asp Pro Asp Asn Glu Thr Tyr Lys Ser Asn Leu Lys
            100                 105                 110

Ile Ala Glu Leu Lys Leu Arg Glu
        115                 120

<210> SEQ ID NO 87
<211> LENGTH: 127
<212> TYPE: PRT
<213> ORGANISM: Artificial Sequence -continued

```
<220> FEATURE:
<223> OTHER INFORMATION: DSS1-binding TPR recognition domain

<400> SEQUENCE: 87

Lys Gln Ala Leu Lys Glu Lys Glu Leu Gly Met Asp Ala Ile Lys Lys
1               5                   10                  15

Lys Asp Phe Asp Thr Ala Leu Lys His Tyr Asp Lys Ala Lys Glu Leu
            20                  25                  30

Asp Pro Thr Asn Met Thr Tyr Ile Thr Ser Gln Ala Ala Val Tyr Phe
        35                  40                  45

Glu Lys Gly Asp Tyr Asn Lys Cys Arg Glu Leu Cys Glu Lys Ala Ile
    50                  55                  60

Glu Val Gly Arg Glu Asn Arg Glu Asp Tyr Arg Gln Ile Ala Asp Ala
65                  70                  75                  80

Tyr Ala Leu Ile Gly Leu Ser Tyr Phe Lys Glu Val Lys Tyr Lys Asp
                85                  90                  95

Ala Ile His Phe Tyr Asn Lys Ser Leu Ala Glu His Arg Thr Pro Asp
            100                 105                 110

Val Leu Lys Lys Cys Gln Gln Ala Glu Lys Ile Leu Lys Glu Gln
        115                 120                 125

<210> SEQ ID NO 88
<211> LENGTH: 50
<212> TYPE: DNA
<213> ORGANISM: Artificial Sequence
<220> FEATURE:
<223> OTHER INFORMATION: Primer forward for NLS-WHW cloning

<400> SEQUENCE: 88
aataaggatc cccgaagaaa aagcggaagg tggctgaggc atggtacaac          50

<210> SEQ ID NO 89
<211> LENGTH: 50
<212> TYPE: DNA
<213> ORGANISM: Artificial Sequence
<220> FEATURE:
<223> OTHER INFORMATION: Primer reverse for NLS-WHW cloning

<400> SEQUENCE: 89
gttgtaccat gcctcagcca ccttccgctt tttcttcggg gatccttatt          50

<210> SEQ ID NO 90
<211> LENGTH: 24
<212> TYPE: PRT
<213> ORGANISM: Artificial Sequence
<220> FEATURE:
<223> OTHER INFORMATION: Hsp90 peptide

<400> SEQUENCE: 90

Ser Ala Ala Val Thr Glu Glu Met Pro Pro Leu Glu Gly Asp Asp Asp
1               5                   10                  15

Thr Ser Arg Met Glu Glu Val Asp
            20

<210> SEQ ID NO 91
<211> LENGTH: 185
<212> TYPE: PRT
<213> ORGANISM: Artificial Sequence
<220> FEATURE:
<223> OTHER INFORMATION: CTPR5 CC1-CTPR390
```

```
<400> SEQUENCE: 91

Ala Glu Ala Trp Cys Asn Leu Gly Cys Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser Ala Cys Ala Trp Tyr Cys Leu Gly Asn Ala Tyr Tyr Lys Gln
        35                  40                  45

Gly Asp Tyr Asp Glu Ala Ile Glu Tyr Tyr Gln Lys Ala Leu Glu Leu
    50                  55                  60

Asp Pro Arg Ser Ala Glu Ala Trp Lys Asn Leu Gly Asn Ala Tyr Tyr
65                  70                  75                  80

Lys Gln Gly Asp Tyr Gln Lys Ala Ile Glu Tyr Tyr Gln Lys Ala Leu
                85                  90                  95

Glu Leu Asp Pro Asn Asn Ala Ser Ala Trp Tyr Asn Leu Gly Asn Ala
            100                 105                 110

Tyr Tyr Lys Gln Gly Asp Tyr Gln Lys Ala Ile Glu Tyr Tyr Gln Lys
        115                 120                 125

Ala Leu Glu Leu Asp Pro Asn Asn Ala Lys Ala Trp Tyr Arg Arg Gly
    130                 135                 140

Asn Ala Tyr Tyr Lys Gln Gly Asp Tyr Gln Lys Ala Ile Glu Asp Tyr
145                 150                 155                 160

Gln Lys Ala Leu Glu Leu Asp Pro Asn Asn Lys Ala Lys Gln Asn
                165                 170                 175

Leu Gly Asn Ala Lys Gln Lys Gln Gly
            180                 185

<210> SEQ ID NO 92
<211> LENGTH: 555
<212> TYPE: DNA
<213> ORGANISM: Artificial Sequence
<220> FEATURE:
<223> OTHER INFORMATION: CTPR5_CC1-CTPR390

<400> SEQUENCE: 92
gctgaggcat ggtgcaacct gggttgcgct tactacaaac agggtgacta cgacgaagct    60
atcgaatact accagaaggc tctcgagctg gacccgagat ccgcttgtgc atggtactgc   120
ctgggtaacg cttactacaa acagggtgac tacgacgaag ctatcgaata ctaccagaag   180
gctctcgagc tggacccgag atccgctgag gcatggaaga acctgggtaa cgcttactac   240
aaacagggtg actaccagaa agctatcgaa tactaccaga aggctctcga gttagacccg   300
aacaacgcta gcgcgtggta taatctcggc aatgcatatt ataagcaagg cgattatcaa   360
aaagcaattg agtattatca aaaggcgtta gagctcgatc caaataatgc aaaggcatgg   420
taccgccggg ggaacgcgta ttacaaacag ggagactacc agaaggcgat cgaagactac   480
cagaaagcgc tgggactgga cccgaataac gctaaagcta acagaacct gggtaacgct   540 aaacagaaac aggggt                                                    555

<210> SEQ ID NO 93
<211> LENGTH: 193
<212> TYPE: PRT
<213> ORGANISM: Artificial Sequence
<220> FEATURE:
<223> OTHER INFORMATION: CTPR5 CC1-CTPR2A
```

<400> SEQUENCE: 93

Ala Glu Ala Trp Cys Asn Leu Gly Cys Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser Ala Cys Ala Trp Tyr Cys Leu Gly Asn Ala Tyr Tyr Lys Gln
        35                  40                  45

Gly Asp Tyr Asp Glu Ala Ile Glu Tyr Tyr Gln Lys Ala Leu Glu Leu
    50                  55                  60

Asp Pro Arg Ser Ala Leu Ala Glu Lys Asn Leu Gly Asn Ala Tyr Tyr
65                  70                  75                  80

Lys Gln Lys Asp Phe Asp Thr Ala Leu Lys His Tyr Asp Lys Ala Lys
                85                  90                  95

Glu Leu Asp Pro Thr Asn Met Thr Tyr Ile Thr Asn Gln Ala Ala Val
            100                 105                 110

Tyr Phe Glu Lys Gly Asp Tyr Asn Lys Cys Arg Glu Leu Cys Glu Lys
        115                 120                 125

Ala Ile Glu Val Gly Arg Glu Asn Arg Glu Asp Tyr Arg Gln Ile Ala
    130                 135                 140

Lys Ala Tyr Ala Arg Ile Gly Asn Ser Tyr Phe Lys Glu Glu Lys Tyr
145                 150                 155                 160

Lys Asp Ala Ile His Phe Tyr Asn Lys Ser Leu Ala Glu His Arg Thr
                165                 170                 175

Pro Asp Val Leu Lys Lys Cys Gln Gln Ala Glu Lys Ile Leu Lys Glu
            180                 185                 190

Gln

<210> SEQ ID NO 94
<211> LENGTH: 579
<212> TYPE: DNA
<213> ORGANISM: Artificial Sequence
<220> FEATURE:
<223> OTHER INFORMATION: CTPR5 CC1-CTPR2A

<400> SEQUENCE: 94
gctgaggcat ggtgcaacct gggttgcgct tactacaaac agggtgacta cgacgaagct        60
atcgaatact accagaaggc tctcgagctg gacccgagat ccgcttgtgc atggtactgc       120
ctgggtaacg cttactacaa acagggtgac tacgacgaag ctatcgaata ctaccagaag       180
gctctcgagc tggacccgag atccgcactg gcagaaaaga acctggggaa cgcttactac       240
aagcagaaag actttgacac agccttgaag cattacgaca agccaagga gctggacccc       300 actaacatga cttacattac caatcaagca gcggtatact tgaaaaggg cgactacaat       360 aagtgccggg agctttgtga aaggccatt gaagtgggga gagaaaaccg agaagactat       420
cgacagattg ccaaagcata tgctcgaatt ggcaactcct acttcaaaga agaaaagtac       480
aaggatgcca tccatttcta taacaagtct ctggcagagc accgaacccc agatgtgctc       540
aagaaatgcc agcaggcaga gaaaatcctg aaggagcaa                             579

<210> SEQ ID NO 95
<211> LENGTH: 193
<212> TYPE: PRT
<213> ORGANISM: Artificial Sequence
<220> FEATURE:
<223> OTHER INFORMATION: CTPR5 CC1-CTPR2A_T332R_D334K

<400> SEQUENCE: 95

```
Ala Glu Ala Trp Cys Asn Leu Gly Cys Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser Ala Cys Ala Trp Tyr Cys Leu Gly Asn Ala Tyr Tyr Lys Gln
        35                  40                  45

Gly Asp Tyr Asp Glu Ala Ile Glu Tyr Tyr Gln Lys Ala Leu Glu Leu
    50                  55                  60

Asp Pro Arg Ser Ala Leu Ala Glu Lys Asn Leu Gly Asn Ala Tyr Tyr
65              70                  75                  80

Lys Gln Lys Asp Phe Asp Thr Ala Leu Lys His Tyr Asp Lys Ala Lys
                85                  90                  95

Glu Leu Asp Pro Thr Asn Met Thr Tyr Ile Thr Asn Gln Ala Ala Val
            100                 105                 110

Tyr Phe Glu Lys Gly Asp Tyr Asn Lys Cys Arg Glu Leu Cys Glu Lys
        115                 120                 125

Ala Ile Glu Val Gly Arg Glu Asn Arg Glu Asp Tyr Arg Gln Ile Ala
    130                 135                 140

Lys Ala Tyr Ala Arg Ile Gly Asn Ser Tyr Phe Lys Glu Glu Lys Tyr
145                 150                 155                 160

Lys Asp Ala Ile His Phe Tyr Asn Lys Ser Leu Ala Glu His Arg Arg
                165                 170                 175

Pro Lys Val Leu Lys Lys Cys Gln Gln Ala Glu Lys Ile Leu Lys Glu
            180                 185                 190

Gln
```

<210> SEQ ID NO 96
<211> LENGTH: 580
<212> TYPE: DNA
<213> ORGANISM: Artificial Sequence
<220> FEATURE:
<223> OTHER INFORMATION: CTPR5_CC1-CTPR2A_T332R_D334K

<400> SEQUENCE: 96

```
gctgaggcat ggtgcaacct gggttgcgct tactacaaac agggtgacta cgacgaagct      60
atcgaatact accagaaggc tctcgagctg gacccgagat ccgcttgtgc atggtactgc     120
ctgggtaacg cttactacaa acagggtgac tacgacgaag ctatcgaata ctaccagaag     180
gctctcgagc tggacccgag atccgcactg gcagaaaaga acctggggaa cgcttactac     240
aagcagaaag actttgacac agccttgaag cattacgaca agccaagga gctggacccc      300
actaacatga cttacattac caatcaagca gcggtatact ttgaaaaggg cgactacaat     360
aagtgccggg agctttgtga aaggccatt gaagtgggga gagaaaaccg agaagactat      420
cgacagattg ccaaagcata tgctcgaatt ggcaactcct acttcaaaga agaaagtac      480
aaggatgcca tccatttcta taacaagtct ctggcagagc accgacgccc aaaagtgctc     540
aagaaatgcc agcaggcaga gaaaatcctg aaggagcaat                            580
```

<210> SEQ ID NO 97
<211> LENGTH: 34
<212> TYPE: PRT
<213> ORGANISM: Artificial Sequence
<220> FEATURE:
<223> OTHER INFORMATION: CTPR1 X

<400> SEQUENCE: 97

Ala Cys Ala Trp Tyr His Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser

<210> SEQ ID NO 98
<211> LENGTH: 102
<212> TYPE: DNA
<213> ORGANISM: Artificial Sequence
<220> FEATURE:
<223> OTHER INFORMATION: CTPR1 X DNA

<400> SEQUENCE: 98
gcttgtgcat ggtaccacct gggtaacgct tactacaaac agggtgacta cgacgaagct    60
atcgaatact accagaaggc tctcgagctg acccgagat cc    102

<210> SEQ ID NO 99
<211> LENGTH: 34
<212> TYPE: PRT
<213> ORGANISM: Artificial Sequence
<220> FEATURE:
<223> OTHER INFORMATION: CTPR1 X1

<400> SEQUENCE: 99

Ala Cys Ala Trp Tyr Asn Leu Gly His Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser

<210> SEQ ID NO 100
<211> LENGTH: 102
<212> TYPE: DNA
<213> ORGANISM: Artificial Sequence
<220> FEATURE:
<223> OTHER INFORMATION: CTPR1 X1 DNA

<400> SEQUENCE: 100
gcttgtgcat ggtacaacct gggtcacgct tactacaaac agggtgacta cgacgaagct    60
atcgaatact accagaaggc tctcgagctg acccgagat cc    102

<210> SEQ ID NO 101
<211> LENGTH: 102
<212> TYPE: PRT
<213> ORGANISM: Artificial Sequence
<220> FEATURE:
<223> OTHER INFORMATION: CTPR3 WXW

<400> SEQUENCE: 101

Ala Glu Ala Trp Tyr Asn Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser Ala Cys Ala Trp Tyr His Leu Gly Asn Ala Tyr Tyr Lys Gln
            35                  40                  45

Gly Asp Tyr Asp Glu Ala Ile Glu Tyr Tyr Gln Lys Ala Leu Glu Leu
        50                  55                  60

```
Asp Pro Arg Ser Ala Glu Ala Trp Tyr Asn Leu Gly Asn Ala Tyr Tyr
 65                  70                  75                  80

Lys Gln Gly Asp Tyr Asp Glu Ala Ile Glu Tyr Tyr Gln Lys Ala Leu
                 85                  90                  95

Glu Leu Asp Pro Arg Ser
            100

<210> SEQ ID NO 102
<211> LENGTH: 306
<212> TYPE: DNA
<213> ORGANISM: Artificial Sequence
<220> FEATURE:
<223> OTHER INFORMATION: CTPR3 WXW

<400> SEQUENCE: 102
gctgaggcat ggtacaacct gggtaacgct tactacaaac agggtgacta cgacgaagct     60
atcgaatact accagaaggc tctcgagctg gacccgagat ccgcttgtgc atggtaccac    120
ctgggtaacg cttactacaa acagggtgac tacgacgaag ctatcgaata ctaccagaag    180
gctctcgagc tggacccgag atccgctgag gcatggtaca acctgggtaa cgcttactac    240
aaacagggtg actacgacga agctatcgaa tactaccaga aggctctcga gctggacccg    300
agatcc                                                               306

<210> SEQ ID NO 103
<211> LENGTH: 102
<212> TYPE: PRT
<213> ORGANISM: Artificial Sequence
<220> FEATURE:
<223> OTHER INFORMATION: CTPR3 WX1W

<400> SEQUENCE: 103

Ala Glu Ala Trp Tyr Asn Leu Gly Asn Ala Tyr Tyr Lys Gln Gly Asp
 1               5                  10                  15

Tyr Asp Glu Ala Ile Glu Tyr Tyr Gln Lys Ala Leu Glu Leu Asp Pro
             20                  25                  30

Arg Ser Ala Cys Ala Trp Tyr Asn Leu Gly His Ala Tyr Tyr Lys Gln
         35                  40                  45

Gly Asp Tyr Asp Glu Ala Ile Glu Tyr Tyr Gln Lys Ala Leu Glu Leu
     50                  55                  60

Asp Pro Arg Ser Ala Glu Ala Trp Tyr Asn Leu Gly Asn Ala Tyr Tyr
 65                  70                  75                  80

Lys Gln Gly Asp Tyr Asp Glu Ala Ile Glu Tyr Tyr Gln Lys Ala Leu
                 85                  90                  95

Glu Leu Asp Pro Arg Ser
            100

<210> SEQ ID NO 104
<211> LENGTH: 306
<212> TYPE: DNA
<213> ORGANISM: Artificial Sequence
<220> FEATURE:
<223> OTHER INFORMATION: CTPR3 WX1W

<400> SEQUENCE: 104
gctgaggcat ggtacaacct gggtaacgct tactacaaac agggtgacta cgacgaagct     60
atcgaatact accagaaggc tctcgagctg gacccgagat ccgcttgtgc atggtacaac    120
ctgggtcacg cttactacaa acagggtgac tacgacgaag ctatcgaata ctaccagaag    180
gctctcgagc tggacccgag atctgctgag gcatggtaca acctgggtaa cgcttactac    240
```
aaacagggtg actacgacga agctatcgaa tactaccaga aggctctcga gctggacccg    300
agatcc    306

<210> SEQ ID NO 105
<211> LENGTH: 102
<212> TYPE: PRT
<213> ORGANISM: Artificial Sequence
<220> FEATURE:
<223> OTHER INFORMATION: CTPR3 WC1W

<400> SEQUENCE: 105

Ala Glu Ala Trp Tyr Asn Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser Ala Cys Ala Trp Tyr Cys Leu Gly Asn Ala Tyr Tyr Lys Gln
        35                  40                  45

Gly Asp Tyr Asp Glu Ala Ile Glu Tyr Tyr Gln Lys Ala Leu Glu Leu
    50                  55                  60

Asp Pro Arg Ser Ala Glu Ala Trp Tyr Asn Leu Gly Asn Ala Tyr Tyr
65                  70                  75                  80

Lys Gln Gly Asp Tyr Asp Glu Ala Ile Glu Tyr Tyr Gln Lys Ala Leu
                85                  90                  95

Glu Leu Asp Pro Arg Ser
            100

<210> SEQ ID NO 106
<211> LENGTH: 306
<212> TYPE: DNA
<213> ORGANISM: Artificial Sequence
<220> FEATURE:
<223> OTHER INFORMATION: CTPR3 WC1W

<400> SEQUENCE: 106
gctgaggcat ggtacaacct gggtaacgct tactacaaac agggtgacta cgacgaagct    60
atcgaatact accagaaggc tctcgagctg gacccgagat ccgcttgtgc atggtactgc   120
ctgggtaacg cttactacaa acagggtgac tacgacgaag ctatcgaata ctaccagaag   180
gctctcgagc tggacccgag atccgctgag gcatggtaca acctgggtaa cgcttactac   240
aaacagggtg actacgacga agctatcgaa tactaccaga aggctctcga gctggacccg   300
agatcc    306

<210> SEQ ID NO 107
<211> LENGTH: 118
<212> TYPE: PRT
<213> ORGANISM: Artificial Sequence
<220> FEATURE:
<223> OTHER INFORMATION: CTPR3 WWW-Cys

<400> SEQUENCE: 107

Ala Glu Ala Trp Tyr Asn Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser Ala Glu Ala Trp Tyr Asn Leu Gly Asn Ala Tyr Tyr Lys Gln
        35                  40                  45

Gly Asp Tyr Asp Glu Ala Ile Glu Tyr Tyr Gln Lys Ala Leu Glu Leu
    50                  55                  60

```
Asp Pro Arg Ser Ala Glu Ala Trp Tyr Asn Leu Gly Asn Ala Tyr Tyr
 65                  70                  75                  80

Lys Gln Gly Asp Tyr Asp Glu Ala Ile Glu Tyr Tyr Gln Lys Ala Leu
                 85                  90                  95

Glu Leu Asp Pro Arg Ser Ala Glu Ala Lys Gln Asn Leu Gly Asn Ala
            100                 105                 110

Lys Gln Lys Gln Gly Cys
        115

<210> SEQ ID NO 108
<211> LENGTH: 354
<212> TYPE: DNA
<213> ORGANISM: Artificial Sequence
<220> FEATURE:
<223> OTHER INFORMATION: CTPR3 WWW-Cys

<400> SEQUENCE: 108
gctgaggcat ggtacaacct gggtaacgct tactacaaac agggtgacta cgacgaagct      60
atcgaatact accagaaggc tctcgagctg gacccgagat ccgctgaggc atggtacaac     120
ctgggtaacg cttactacaa acagggtgac tacgacgaag ctatcgaata ctaccagaag     180
gctctcgagc tggacccgag atccgctgag gcatggtaca acctgggtaa cgcttactac     240
aaacagggtg actacgacga agctatcgaa tactaccaga aggctctcga gctggacccg     300
agatccgctg aagctaaaca gaacctgggt aacgctaaac agaaacaggg ttgt            354

<210> SEQ ID NO 109
<211> LENGTH: 5
<212> TYPE: PRT
<213> ORGANISM: Artificial Sequence
<220> FEATURE:
<223> OTHER INFORMATION: tag peptide

<400> SEQUENCE: 109

Met Glu Glu Val Phe
1               5

<210> SEQ ID NO 110
<211> LENGTH: 13
<212> TYPE: PRT
<213> ORGANISM: Artificial Sequence
<220> FEATURE:
<223> OTHER INFORMATION: amino acid sequence
<220> FEATURE:
<221> NAME/KEY: VARIANT
<222> LOCATION: (2)..(2)
<223> OTHER INFORMATION: E, H, C or D
<220> FEATURE:
<221> NAME/KEY: VARIANT
<222> LOCATION: (5)..(5)
<223> OTHER INFORMATION: Y, H, C, D or E
<220> FEATURE:
<221> NAME/KEY: VARIANT
<222> LOCATION: (9)..(9)
<223> OTHER INFORMATION: N, H, C, D or E
<220> FEATURE:
<221> NAME/KEY: VARIANT
<222> LOCATION: (13)..(13)
<223> OTHER INFORMATION: K, H, C, D or E

<400> SEQUENCE: 110

Ala Xaa Ala Trp Xaa Asn Leu Gly Xaa Ala Tyr Tyr Xaa
1               5                   10
```

```
<210> SEQ ID NO 111
<211> LENGTH: 13
<212> TYPE: PRT
<213> ORGANISM: Artificial Sequence
<220> FEATURE:
<223> OTHER INFORMATION: amino acid sequence
<220> FEATURE:
<221> NAME/KEY: VARIANT
<222> LOCATION: (5)..(5)
<223> OTHER INFORMATION: Y, H, C, D or E
<220> FEATURE:
<221> NAME/KEY: VARIANT
<222> LOCATION: (9)..(9)
<223> OTHER INFORMATION: N, H, C, D or E
<220> FEATURE:
<221> NAME/KEY: VARIANT
<222> LOCATION: (13)..(13)
<223> OTHER INFORMATION: K, H, C, D or E

<400> SEQUENCE: 111

Ala Glu Ala Trp Xaa Asn Leu Gly Xaa Ala Tyr Tyr Xaa
 1               5                  10

<210> SEQ ID NO 112
<211> LENGTH: 13
<212> TYPE: PRT
<213> ORGANISM: Artificial Sequence
<220> FEATURE:
<223> OTHER INFORMATION: amino acid sequence
<220> FEATURE:
<221> NAME/KEY: VARIANT
<222> LOCATION: (6)..(6)
<223> OTHER INFORMATION: N, H, C, D or E
<220> FEATURE:
<221> NAME/KEY: VARIANT
<222> LOCATION: (9)..(9)
<223> OTHER INFORMATION: N, H, C, D or E
<220> FEATURE:
<221> NAME/KEY: VARIANT
<222> LOCATION: (13)..(13)
<223> OTHER INFORMATION: K, H, C, D or E

<400> SEQUENCE: 112

Ala Glu Ala Trp Tyr Xaa Leu Gly Xaa Ala Tyr Tyr Xaa
 1               5                  10

<210> SEQ ID NO 113
<211> LENGTH: 13
<212> TYPE: PRT
<213> ORGANISM: Artificial Sequence
<220> FEATURE:
<223> OTHER INFORMATION: amino acid sequence
<220> FEATURE:
<221> NAME/KEY: VARIANT
<222> LOCATION: (9)..(9)
<223> OTHER INFORMATION: N, H, C, D or E
<220> FEATURE:
<221> NAME/KEY: VARIANT
<222> LOCATION: (13)..(13)
<223> OTHER INFORMATION: K, H, C, D or E

<400> SEQUENCE: 113

Ala Glu Ala Trp Tyr Asn Leu Gly Xaa Ala Tyr Tyr Xaa
 1               5                  10

<210> SEQ ID NO 114
<211> LENGTH: 13
<212> TYPE: PRT
<213> ORGANISM: Artificial Sequence
<220> FEATURE:
<223> OTHER INFORMATION: amino acid sequence
```

```
<220> FEATURE:
<221> NAME/KEY: VARIANT
<222> LOCATION: (2)..(2)
<223> OTHER INFORMATION: E, H, C or D
<220> FEATURE:
<221> NAME/KEY: VARIANT
<222> LOCATION: (5)..(5)
<223> OTHER INFORMATION: Y, H, C, D or E
<220> FEATURE:
<221> NAME/KEY: VARIANT
<222> LOCATION: (6)..(6)
<223> OTHER INFORMATION: N, H, C, D or E
<220> FEATURE:
<221> NAME/KEY: VARIANT
<222> LOCATION: (9)..(9)
<223> OTHER INFORMATION: N, H, C, D or E

<400> SEQUENCE: 114

Ala Xaa Ala Trp Xaa Xaa Leu Gly Xaa Ala Tyr Tyr Lys
1               5                   10

<210> SEQ ID NO 115
<211> LENGTH: 13
<212> TYPE: PRT
<213> ORGANISM: Artificial Sequence
<220> FEATURE:
<223> OTHER INFORMATION: H1

<400> SEQUENCE: 115

Ala His Ala Trp His His Leu Gly His Ala Tyr Tyr Lys
1               5                   10

<210> SEQ ID NO 116
<211> LENGTH: 39
<212> TYPE: DNA
<213> ORGANISM: Artificial Sequence
<220> FEATURE:
<223> OTHER INFORMATION: H1

<400> SEQUENCE: 116
gctcacgcat ggcaccacct gggtcacgct tactacaaa                              39

<210> SEQ ID NO 117
<211> LENGTH: 13
<212> TYPE: PRT
<213> ORGANISM: Artificial Sequence
<220> FEATURE:
<223> OTHER INFORMATION: H2

<400> SEQUENCE: 117

Ala His Ala Trp His Asn Leu Gly His Ala Tyr Leu His
1               5                   10

<210> SEQ ID NO 118
<211> LENGTH: 39
<212> TYPE: DNA
<213> ORGANISM: Artificial Sequence
<220> FEATURE:
<223> OTHER INFORMATION: H2

<400> SEQUENCE: 118
gctcacgcat ggcacaacct gggtcacgct tacctgcac                              39

<210> SEQ ID NO 119
<211> LENGTH: 34
<212> TYPE: PRT
<213> ORGANISM: Artificial Sequence
<220> FEATURE:
<223> OTHER INFORMATION: CTPR1 E2H Y5H N6H N9H
```

-continued

<400> SEQUENCE: 119

Ala His Ala Trp His His Leu Gly His Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser

<210> SEQ ID NO 120
<211> LENGTH: 102
<212> TYPE: DNA
<213> ORGANISM: Artificial Sequence
<220> FEATURE:
<223> OTHER INFORMATION: CTPR1 E2H Y5H N6H N9H

<400> SEQUENCE: 120
gctcacgcat ggcaccacct gggtcacgct tactacaaac agggtgacta cgacgaagct    60
atcgaatact accagaaggc tctcgagctg gacccgagat cc                      102

<210> SEQ ID NO 121
<211> LENGTH: 34
<212> TYPE: PRT
<213> ORGANISM: Artificial Sequence
<220> FEATURE:
<223> OTHER INFORMATION: CTPR1 E2H Y5H N9H Y12L K13H

<400> SEQUENCE: 121

Ala His Ala Trp His Asn Leu Gly His Ala Tyr Leu His Gln Gly Asp
1               5                   10                  15

Tyr Asp Glu Ala Ile Glu Tyr Tyr Gln Lys Ala Leu Glu Leu Asp Pro
            20                  25                  30

Arg Ser

<210> SEQ ID NO 122
<211> LENGTH: 102
<212> TYPE: DNA
<213> ORGANISM: Artificial Sequence
<220> FEATURE:
<223> OTHER INFORMATION: CTPR1 E2H Y5H N9H Y12L K13H

<400> SEQUENCE: 122
gctcacgcat ggcacaacct gggtcacgct tacctgcacc agggtgacta cgacgaagct    60
atcgaatact accagaaggc tctcgagctg gacccgagat cc                      102

<210> SEQ ID NO 123
<211> LENGTH: 102
<212> TYPE: PRT
<213> ORGANISM: Artificial Sequence
<220> FEATURE:
<223> OTHER INFORMATION: CTPR3 WH1W

<400> SEQUENCE: 123

Ala Glu Ala Trp Tyr Asn Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser Ala His Ala Trp His His Leu Gly His Ala Tyr Tyr Lys Gln
            35                  40                  45

Gly Asp Tyr Asp Glu Ala Ile Glu Tyr Tyr Gln Lys Ala Leu Glu Leu
        50                  55                  60

Asp Pro Arg Ser Ala Glu Ala Trp Tyr Asn Leu Gly Asn Ala Tyr Tyr
65                  70                  75                  80

Lys Gln Gly Asp Tyr Asp Glu Ala Ile Glu Tyr Tyr Gln Lys Ala Leu
                85                  90                  95

Glu Leu Asp Pro Arg Ser
            100

<210> SEQ ID NO 124
<211> LENGTH: 306
<212> TYPE: DNA
<213> ORGANISM: Artificial Sequence
<220> FEATURE:
<223> OTHER INFORMATION: CTPR3 WH1W

<400> SEQUENCE: 124
gctgaggcat ggtacaacct gggttacgct tactacaaac agggtgacta cgacgaagct     60
atcgaatact accagaaggc tctcgagctg gacccgagat ccgctcacgc atggcaccac    120
ctgggtcacg cttactacaa acagggtgac tacgacgaag ctatcgaata ctaccagaag    180
gctctcgagc tggacccgag atccgctgag gcatggtaca acctgggtta cgcttactac    240
aaacagggtg actacgacga agctatcgaa tactaccaga aggctctcga gctggacccg    300
agatcc                                                                306

<210> SEQ ID NO 125
<211> LENGTH: 136
<212> TYPE: PRT
<213> ORGANISM: Artificial Sequence
<220> FEATURE:
<223> OTHER INFORMATION: CTPR4 WH1H1W

<400> SEQUENCE: 125

Ala Glu Ala Trp Tyr Asn Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
                20                  25                  30

Arg Ser Ala His Ala Trp His His Leu Gly His Ala Tyr Tyr Lys Gln
            35                  40                  45

Gly Asp Tyr Asp Glu Ala Ile Glu Tyr Tyr Gln Lys Ala Leu Glu Leu
        50                  55                  60

Asp Pro Arg Ser Ala His Ala Trp His His Leu Gly His Ala Tyr Tyr
65                  70                  75                  80

Lys Gln Gly Asp Tyr Asp Glu Ala Ile Glu Tyr Tyr Gln Lys Ala Leu
                85                  90                  95

Glu Leu Asp Pro Arg Ser Ala Glu Ala Trp Tyr Asn Leu Gly Asn Ala
            100                 105                 110

Tyr Tyr Lys Gln Gly Asp Tyr Asp Glu Ala Ile Glu Tyr Tyr Gln Lys
        115                 120                 125

Ala Leu Glu Leu Asp Pro Arg Ser
    130                 135

<210> SEQ ID NO 126
<211> LENGTH: 408
<212> TYPE: DNA
<213> ORGANISM: Artificial Sequence
<220> FEATURE:
<223> OTHER INFORMATION: CTPR4 WH1H1W

<400> SEQUENCE: 126

```
gctgaggcat ggtacaacct gggttacgct tactacaaac agggtgacta cgacgaagct    60
atcgaatact accagaaggc tctcgagctg gacccgagat ccgctcacgc atggcaccac   120
ctgggtcacg cttactacaa acagggtgac tacgacgaag ctatcgaata ctaccagaag   180
gctctcgagc tggacccgag atccgctcac gcatggcacc acctgggtca cgcttactac   240
aaacagggtg actacgacga agctatcgaa tactaccaga aggctctcga gctggacccg   300
agatccgctg aggcatggta caacctgggt tacgcttact acaaacaggg tgactacgac   360
gaagctatcg aatactacca gaaggctctc gagctggacc cgagatcc               408
```

<210> SEQ ID NO 127
<211> LENGTH: 170
<212> TYPE: PRT
<213> ORGANISM: Artificial Sequence
<220> FEATURE:
<223> OTHER INFORMATION: CTPR5 WH1H1H1W

<400> SEQUENCE: 127

```
Ala Glu Ala Trp Tyr Asn Leu Gly Asn Ala Tyr Tyr Lys Gln Gly Asp
1               5                   10                  15
Tyr Asp Glu Ala Ile Glu Tyr Tyr Gln Lys Ala Leu Glu Leu Asp Pro
            20                  25                  30
Arg Ser Ala His Ala Trp His His Leu Gly His Ala Tyr Tyr Lys Gln
        35                  40                  45
Gly Asp Tyr Asp Glu Ala Ile Glu Tyr Tyr Gln Lys Ala Leu Glu Leu
    50                  55                  60
Asp Pro Arg Ser Ala His Ala Trp His His Leu Gly His Ala Tyr Tyr
65                  70                  75                  80
Lys Gln Gly Asp Tyr Asp Glu Ala Ile Glu Tyr Tyr Gln Lys Ala Leu
                85                  90                  95
Glu Leu Asp Pro Arg Ser Ala His Ala Trp His His Leu Gly His Ala
            100                 105                 110
Tyr Tyr Lys Gln Gly Asp Tyr Asp Glu Ala Ile Glu Tyr Tyr Gln Lys
        115                 120                 125
Ala Leu Glu Leu Asp Pro Arg Ser Ala Glu Ala Trp Tyr Asn Leu Gly
    130                 135                 140
Asn Ala Tyr Tyr Lys Gln Gly Asp Tyr Asp Glu Ala Ile Glu Tyr Tyr
145                 150                 155                 160
Gln Lys Ala Leu Glu Leu Asp Pro Arg Ser
                165                 170
```

<210> SEQ ID NO 128
<211> LENGTH: 510
<212> TYPE: DNA
<213> ORGANISM: Artificial Sequence
<220> FEATURE:
<223> OTHER INFORMATION: CTPR5 WH1H1H1W

<400> SEQUENCE: 128

```
gctgaggcat ggtacaacct gggttacgct tactacaaac agggtgacta cgacgaagct    60
atcgaatact accagaaggc tctcgagctg gacccgagat ccgctcacgc atggcaccac   120
ctgggtcacg cttactacaa acagggtgac tacgacgaag ctatcgaata ctaccagaag   180
gctctcgagc tggacccgag atccgctcac gcatggcacc acctgggtca cgcttactac   240
aaacagggtg actacgacga agctatcgaa tactaccaga aggctctcga gctggacccg   300
```

```
agatccgctc acgcatggca ccacctgggt cacgcttact acaaacaggg tgactacgac    360
gaagctatcg aatactacca gaaggctctc gagctggacc cgagatccgc tgaggcatgg    420
tacaacctgg gttacgctta ctacaaacag ggtgactacg acgaagctat cgaatactac    480
cagaaggctc tcgagctgga cccgagatcc                                    510
```

<210> SEQ ID NO 129
<211> LENGTH: 204
<212> TYPE: PRT
<213> ORGANISM: Artificial Sequence
<220> FEATURE:
<223> OTHER INFORMATION: CTPR6 WH1H1H1H1W

<400> SEQUENCE: 129

```
Ala Glu Ala Trp Tyr Asn Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser Ala His Ala Trp His His Leu Gly His Ala Tyr Tyr Lys Gln
        35                  40                  45

Gly Asp Tyr Asp Glu Ala Ile Glu Tyr Tyr Gln Lys Ala Leu Glu Leu
    50                  55                  60

Asp Pro Arg Ser Ala His Ala Trp His His Leu Gly His Ala Tyr Tyr
65                  70                  75                  80

Lys Gln Gly Asp Tyr Asp Glu Ala Ile Glu Tyr Tyr Gln Lys Ala Leu
                85                  90                  95

Glu Leu Asp Pro Arg Ser Ala His Ala Trp His His Leu Gly His Ala
            100                 105                 110

Tyr Tyr Lys Gln Gly Asp Tyr Asp Glu Ala Ile Glu Tyr Tyr Gln Lys
        115                 120                 125

Ala Leu Glu Leu Asp Pro Arg Ser Ala His Ala Trp His His Leu Gly
    130                 135                 140

His Ala Tyr Tyr Lys Gln Gly Asp Tyr Asp Glu Ala Ile Glu Tyr Tyr
145                 150                 155                 160

Gln Lys Ala Leu Glu Leu Asp Pro Arg Ser Ala Glu Ala Trp Tyr Asn
                165                 170                 175

Leu Gly Asn Ala Tyr Tyr Lys Gln Gly Asp Tyr Asp Glu Ala Ile Glu
            180                 185                 190

Tyr Tyr Gln Lys Ala Leu Glu Leu Asp Pro Arg Ser
        195                 200
```

<210> SEQ ID NO 130
<211> LENGTH: 612
<212> TYPE: DNA
<213> ORGANISM: Artificial Sequence
<220> FEATURE:
<223> OTHER INFORMATION: CTPR6 WH1H1H1H1W

<400> SEQUENCE: 130

```
gctgaggcat ggtacaacct gggttacgct tactacaaac agggtgacta cgacgaagct    60
atcgaatact accagaaggc tctcgagctg gacccgagat ccgctcacgc atggcaccac    120
ctgggtcacg cttactacaa acagggtgac tacgacgaag ctatcgaata ctaccagaag    180
gctctcgagc tggacccgag atccgctcac gcatggcacc acctgggtca cgcttactac    240
aaacagggtg actacgacga agctatcgaa tactaccaga aggctctcga gctggacccg    300
agatccgctc acgcatggca ccacctgggt cacgcttact acaaacaggg tgactacgac    360
```

```
gaagctatcg aatactacca gaaggctctc gagctggacc cgagatccgc tcacgcatgg    420
caccacctgg gtcacgctta ctacaaacag ggtgactacg acgaagctat cgaatactac    480
cagaaggctc tcgagctgga cccgagatcc gctgaggcat ggtacaacct gggttacgct    540
tactacaaac agggtgacta cgacgaagct atcgaatact accagaaggc tctcgagctg    600
gacccgagat cc                                                        612
```

```
<210> SEQ ID NO 131
<211> LENGTH: 238
<212> TYPE: PRT
<213> ORGANISM: Artificial Sequence
<220> FEATURE:
<223> OTHER INFORMATION: CTPR7 WH1H1H1H1H1W

<400> SEQUENCE: 131

Ala Glu Ala Trp Tyr Asn Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser Ala His Ala Trp His His Leu Gly His Ala Tyr Tyr Lys Gln
        35                  40                  45

Gly Asp Tyr Asp Glu Ala Ile Glu Tyr Tyr Gln Lys Ala Leu Glu Leu
    50                  55                  60

Asp Pro Arg Ser Ala His Ala Trp His His Leu Gly His Ala Tyr Tyr
65                  70                  75                  80

Lys Gln Gly Asp Tyr Asp Glu Ala Ile Glu Tyr Tyr Gln Lys Ala Leu
                85                  90                  95

Glu Leu Asp Pro Arg Ser Ala His Ala Trp His His Leu Gly His Ala
            100                 105                 110

Tyr Tyr Lys Gln Gly Asp Tyr Asp Glu Ala Ile Glu Tyr Tyr Gln Lys
        115                 120                 125

Ala Leu Glu Leu Asp Pro Arg Ser Ala His Ala Trp His His Leu Gly
    130                 135                 140

His Ala Tyr Tyr Lys Gln Gly Asp Tyr Asp Glu Ala Ile Glu Tyr Tyr
145                 150                 155                 160

Gln Lys Ala Leu Glu Leu Asp Pro Arg Ser Ala His Ala Trp His His
                165                 170                 175

Leu Gly His Ala Tyr Tyr Lys Gln Gly Asp Tyr Asp Glu Ala Ile Glu
            180                 185                 190

Tyr Tyr Gln Lys Ala Leu Glu Leu Asp Pro Arg Ser Ala Glu Ala Trp
        195                 200                 205

Tyr Asn Leu Gly Asn Ala Tyr Tyr Lys Gln Gly Asp Tyr Asp Glu Ala
    210                 215                 220

Ile Glu Tyr Tyr Gln Lys Ala Leu Glu Leu Asp Pro Arg Ser
225                 230                 235
```

```
<210> SEQ ID NO 132
<211> LENGTH: 714
<212> TYPE: DNA
<213> ORGANISM: Artificial Sequence
<220> FEATURE:
<223> OTHER INFORMATION: CTPR7 WH1H1H1H1H1W

<400> SEQUENCE: 132
gctgaggcat ggtacaacct gggttacgct tactacaaac agggtgacta cgacgaagct    60
atcgaatact accagaaggc tctcgagctg gacccgagat ccgctcacgc atggcaccac    120
```

```
ctgggtcacg cttactacaa acagggtgac tacgacgaag ctatcgaata ctaccagaag    180
gctctcgagc tggacccgag atccgctcac gcatggcacc acctgggtca cgcttactac    240
aaacagggtg actacgacga agctatcgaa tactaccaga aggctctcga gctggacccg    300
agatccgctc acgcatggca ccacctgggt cacgcttact acaaacaggg tgactacgac    360
gaagctatcg aatactacca gaaggctctc gagctggacc cgagatccgc tcacgcatgg    420
caccacctgg gtcacgctta ctacaaacag ggtgactacg acgaagctat cgaatactac    480
cagaaggctc tcgagctgga cccgagatcc gctcacgcat ggcaccacct gggtcacgct    540
tactacaaac agggtgacta cgacgaagct atcgaatact accagaaggc tctcgagctg    600
gacccgagat ccgctgaggc atggtacaac ctgggttacg cttactacaa acagggtgac    660
tacgacgaag ctatcgaata ctaccagaag gctctcgagc tggacccgag atcc           714

<210> SEQ ID NO 133
<211> LENGTH: 102
<212> TYPE: PRT
<213> ORGANISM: Artificial Sequence
<220> FEATURE:
<223> OTHER INFORMATION: CTPR3 WH2W

<400> SEQUENCE: 133

Ala Glu Ala Trp Tyr Asn Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser Ala His Ala Trp His Asn Leu Gly His Ala Tyr Leu His Gln
        35                  40                  45

Gly Asp Tyr Asp Glu Ala Ile Glu Tyr Tyr Gln Lys Ala Leu Glu Leu
    50                  55                  60

Asp Pro Arg Ser Ala Glu Ala Trp Tyr Asn Leu Gly Asn Ala Tyr Tyr
65                  70                  75                  80

Lys Gln Gly Asp Tyr Asp Glu Ala Ile Glu Tyr Tyr Gln Lys Ala Leu
                85                  90                  95

Glu Leu Asp Pro Arg Ser
            100

<210> SEQ ID NO 134
<211> LENGTH: 306
<212> TYPE: DNA
<213> ORGANISM: Artificial Sequence
<220> FEATURE:
<223> OTHER INFORMATION: CTPR3 WH2W

<400> SEQUENCE: 134
gctgaggcat ggtacaacct gggttacgct tactacaaac agggtgacta cgacgaagct    60
atcgaatact accagaaggc tctcgagctg gacccgagat ccgctcacgc atggcacaac    120
ctgggtcacg cttacctgca ccagggtgac tacgacgaag ctatcgaata ctaccagaag    180
gctctcgagc tggacccgag atccgctgag gcatggtaca acctgggtta cgcttactac    240
aaacagggtg actacgacga agctatcgaa tactaccaga aggctctcga gctggacccg    300
agatcc                                                                306

<210> SEQ ID NO 135
<211> LENGTH: 136
<212> TYPE: PRT
<213> ORGANISM: Artificial Sequence
```

<220> FEATURE:
<223> OTHER INFORMATION: CTPR4 WH2H2W

<400> SEQUENCE: 135

Ala Glu Ala Trp Tyr Asn Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser Ala His Ala Trp His Asn Leu Gly His Ala Tyr Leu His Gln
        35                  40                  45

Gly Asp Tyr Asp Glu Ala Ile Glu Tyr Tyr Gln Lys Ala Leu Glu Leu
    50                  55                  60

Asp Pro Arg Ser Ala His Ala Trp His Asn Leu Gly His Ala Tyr Leu
65                  70                  75                  80

His Gln Gly Asp Tyr Asp Glu Ala Ile Glu Tyr Tyr Gln Lys Ala Leu
                85                  90                  95

Glu Leu Asp Pro Arg Ser Ala Glu Ala Trp Tyr Asn Leu Gly Asn Ala
            100                 105                 110

Tyr Tyr Lys Gln Gly Asp Tyr Asp Glu Ala Ile Glu Tyr Tyr Gln Lys
        115                 120                 125

Ala Leu Glu Leu Asp Pro Arg Ser
    130                 135

<210> SEQ ID NO 136
<211> LENGTH: 408
<212> TYPE: DNA
<213> ORGANISM: Artificial Sequence
<220> FEATURE:
<223> OTHER INFORMATION: CTPR4 WH2H2W

<400> SEQUENCE: 136
gctgaggcat ggtacaacct gggttacgct tactacaaac agggtgacta cgacgaagct    60
atcgaatact accagaaggc tctcgagctg gacccgagat ccgctcacgc atggcacaac   120
ctgggtcacg cttacctgca ccagggtgac tacgacgaag ctatcgaata ctaccagaag   180
gctctcgagc tggacccgag atccgctcac gcatggcaca acctgggtca cgcttacctg   240
caccagggtg actacgacga agctatcgaa tactaccaga aggctctcga gctggacccg   300
agatccgctg aggcatggta caacctgggt tacgcttact acaaacaggg tgactacgac   360
gaagctatcg aatactacca gaaggctctc gagctggacc cgagatcc               408

<210> SEQ ID NO 137
<211> LENGTH: 170
<212> TYPE: PRT
<213> ORGANISM: Artificial Sequence
<220> FEATURE:
<223> OTHER INFORMATION: CTPR5 WH2H2H2W

<400> SEQUENCE: 137

Ala Glu Ala Trp Tyr Asn Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser Ala His Ala Trp His Asn Leu Gly His Ala Tyr Leu His Gln
        35                  40                  45

Gly Asp Tyr Asp Glu Ala Ile Glu Tyr Tyr Gln Lys Ala Leu Glu Leu
    50                  55                  60

```
Asp Pro Arg Ser Ala His Ala Trp His Asn Leu Gly His Ala Tyr Leu
 65                  70                  75                  80

His Gln Gly Asp Tyr Asp Glu Ala Ile Glu Tyr Tyr Gln Lys Ala Leu
                 85                  90                  95

Glu Leu Asp Pro Arg Ser Ala His Ala Trp His Asn Leu Gly His Ala
            100                 105                 110

Tyr Leu His Gln Gly Asp Tyr Asp Glu Ala Ile Glu Tyr Tyr Gln Lys
        115                 120                 125

Ala Leu Glu Leu Asp Pro Arg Ser Ala Glu Ala Trp Tyr Asn Leu Gly
    130                 135                 140

Asn Ala Tyr Tyr Lys Gln Gly Asp Tyr Asp Glu Ala Ile Glu Tyr Tyr
145                 150                 155                 160

Gln Lys Ala Leu Glu Leu Asp Pro Arg Ser
                165                 170
```

<210> SEQ ID NO 138
<211> LENGTH: 510
<212> TYPE: DNA
<213> ORGANISM: Artificial Sequence
<220> FEATURE:
<223> OTHER INFORMATION: CTPR5 WH2H2H2W

<400> SEQUENCE: 138

```
gctgaggcat ggtacaacct gggttacgct tactacaaac agggtgacta cgacgaagct    60
atcgaatact accagaaggc tctcgagctg acccgagat ccgctcacgc atggcacaac   120
ctgggtcacg cttacctgca ccagggtgac tacgacgaag ctatcgaata ctaccagaag   180
gctctcgagc tggacccgag atccgctcac gcatggcaca acctgggtca cgcttacctg   240
caccagggtg actacgacga agctatcgaa tactaccaga aggctctcga gctggacccg   300
agatccgctc acgcatggca acctgggt cacgcttacc tgcaccaggg tgactacgac   360
gaagctatcg aatactacca gaaggctctc gagctggacc cgagatccgc tgaggcatgg   420
tacaacctgg gttacgctta ctacaaacag ggtgactacg acgaagctat cgaatactac   480
cagaaggctc tcgagctgga cccgagatcc                                    510
```

<210> SEQ ID NO 139
<211> LENGTH: 204
<212> TYPE: PRT
<213> ORGANISM: Artificial Sequence
<220> FEATURE:
<223> OTHER INFORMATION: CTPR6 WH2H2H2H2W

<400> SEQUENCE: 139

```
Ala Glu Ala Trp Tyr Asn Leu Gly Asn Ala Tyr Tyr Lys Gln Gly Asp
  1               5                  10                  15

Tyr Asp Glu Ala Ile Glu Tyr Tyr Gln Lys Ala Leu Glu Leu Asp Pro
             20                  25                  30

Arg Ser Ala His Ala Trp His Asn Leu Gly His Ala Tyr Leu His Gln
         35                  40                  45

Gly Asp Tyr Asp Glu Ala Ile Glu Tyr Tyr Gln Lys Ala Leu Glu Leu
     50                  55                  60

Asp Pro Arg Ser Ala His Ala Trp His Asn Leu Gly His Ala Tyr Leu
 65                  70                  75                  80

His Gln Gly Asp Tyr Asp Glu Ala Ile Glu Tyr Tyr Gln Lys Ala Leu
                 85                  90                  95

Glu Leu Asp Pro Arg Ser Ala His Ala Trp His Asn Leu Gly His Ala
            100                 105                 110
```

Tyr Leu His Gln Gly Asp Tyr Asp Glu Ala Ile Glu Tyr Gln Lys
            115                 120                 125

Ala Leu Glu Leu Asp Pro Arg Ser Ala His Ala Trp His Asn Leu Gly
130                 135                 140

His Ala Tyr Leu His Gln Gly Asp Tyr Asp Glu Ala Ile Glu Tyr Tyr
145                 150                 155                 160

Gln Lys Ala Leu Glu Leu Asp Pro Arg Ser Ala Glu Ala Trp Tyr Asn
                165                 170                 175

Leu Gly Asn Ala Tyr Tyr Lys Gln Gly Asp Tyr Asp Glu Ala Ile Glu
            180                 185                 190

Tyr Tyr Gln Lys Ala Leu Glu Leu Asp Pro Arg Ser
        195                 200

<210> SEQ ID NO 140
<211> LENGTH: 612
<212> TYPE: DNA
<213> ORGANISM: Artificial Sequence
<220> FEATURE:
<223> OTHER INFORMATION: CTPR6 WH2H2H2H2W

<400> SEQUENCE: 140
gctgaggcat ggtacaacct gggttacgct tactacaaac agggtgacta cgacgaagct      60
atcgaatact accagaaggc tctcgagctg acccgagat ccgctcacgc atggcacaac      120
ctgggtcacg cttacctgca ccagggtgac tacgacgaag ctatcgaata ctaccagaag      180
gctctcgagc tggacccgag atccgctcac gcatggcaca acctgggtca cgcttacctg      240
caccagggtg actacgacga agctatcgaa tactaccaga aggctctcga gctggacccg      300
agatccgctc acgcatggca acctgggt cacgcttacc tgcaccaggg tgactacgac      360
gaagctatcg aatactacca gaaggctctc gagctggacc cgagatccgc tcacgcatgg      420
cacaacctgg gtcacgctta cctgcaccag ggtgactacg acgaagctat cgaatactac      480
cagaaggctc tcgagctgga cccgagatcc gctgaggcat ggtacaacct gggttacgct      540
tactacaaac agggtgacta cgacgaagct atcgaatact accagaaggc tctcgagctg      600
gacccgagat cc                                                          612

<210> SEQ ID NO 141
<211> LENGTH: 238
<212> TYPE: PRT
<213> ORGANISM: Artificial Sequence
<220> FEATURE:
<223> OTHER INFORMATION: CTPR7 WH2H2H2H2W

<400> SEQUENCE: 141

Ala Glu Ala Trp Tyr Asn Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser Ala His Ala Trp His Asn Leu Gly His Ala Tyr Leu His Gln
        35                  40                  45

Gly Asp Tyr Asp Glu Ala Ile Glu Tyr Tyr Gln Lys Ala Leu Glu Leu
    50                  55                  60

Asp Pro Arg Ser Ala His Ala Trp His Asn Leu Gly His Ala Tyr Leu
65                  70                  75                  80

His Gln Gly Asp Tyr Asp Glu Ala Ile Glu Tyr Tyr Gln Lys Ala Leu
                85                  90                  95

Glu Leu Asp Pro Arg Ser Ala His Ala Trp His Asn Leu Gly His Ala
                100                 105                 110

Tyr Leu His Gln Gly Asp Tyr Asp Glu Ala Ile Glu Tyr Tyr Gln Lys
            115                 120                 125

Ala Leu Glu Leu Asp Pro Arg Ser Ala His Ala Trp His Asn Leu Gly
        130                 135                 140

His Ala Tyr Leu His Gln Gly Asp Tyr Asp Glu Ala Ile Glu Tyr Tyr
145                 150                 155                 160

Gln Lys Ala Leu Glu Leu Asp Pro Arg Ser Ala His Ala Trp His Asn
                165                 170                 175

Leu Gly His Ala Tyr Leu His Gln Gly Asp Tyr Asp Glu Ala Ile Glu
            180                 185                 190

Tyr Tyr Gln Lys Ala Leu Glu Leu Asp Pro Arg Ser Ala Glu Ala Trp
        195                 200                 205

Tyr Asn Leu Gly Asn Ala Tyr Tyr Lys Gln Gly Asp Tyr Asp Glu Ala
210                 215                 220

Ile Glu Tyr Tyr Gln Lys Ala Leu Glu Leu Asp Pro Arg Ser
225                 230                 235

<210> SEQ ID NO 142
<211> LENGTH: 714
<212> TYPE: DNA
<213> ORGANISM: Artificial Sequence
<220> FEATURE:
<223> OTHER INFORMATION: CTPR7 WH2H2H2H2H2W

<400> SEQUENCE: 142
gctgaggcat ggtacaacct gggttacgct tactacaaac agggtgacta cgacgaagct    60
atcgaatact accagaaggc tctcgagctg gacccgagat ccgctcacgc atggcacaac   120
ctgggtcacg cttacctgca ccagggtgac tacgacgaag ctatcgaata ctaccagaag   180
gctctcgagc tggacccgag atccgctcac gcatggcaca acctgggtca cgcttacctg   240
caccagggtg actacgacga agctatcgaa tactaccaga aggctctcga gctggacccg   300
agatccgctc acgcatggca caacctgggt cacgcttacc tgcaccaggg tgactacgac   360
gaagctatcg aatactacca gaaggctctc gagctggacc cgagatccgc tcacgcatgg   420
cacaacctgg gtcacgctta cctgcaccag ggtgactacg acgaagctat cgaatactac   480
cagaaggctc tcgagctgga cccgagatcc gctcacgcat ggcacaacct gggtcacgct   540
tacctgcacc agggtgacta cgacgaagct atcgaatact accagaaggc tctcgagctg   600
gacccgagat ccgctgaggc atggtacaac ctgggttacg cttactacaa acagggtgac   660
tacgacgaag ctatcgaata ctaccagaag gctctcgagc tggacccgag atcc         714

<210> SEQ ID NO 143
<211> LENGTH: 204
<212> TYPE: PRT
<213> ORGANISM: Artificial Sequence
<220> FEATURE:
<223> OTHER INFORMATION: CTPR6 WWWWWW

<400> SEQUENCE: 143

Ala Glu Ala Trp Tyr Asn Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser Ala Glu Ala Trp Tyr Asn Leu Gly Asn Ala Tyr Tyr Lys Gln
        35                  40                  45

```
Gly Asp Tyr Asp Glu Ala Ile Glu Tyr Tyr Gln Lys Ala Leu Glu Leu
 50                  55                  60

Asp Pro Arg Ser Ala Glu Ala Trp Tyr Asn Leu Gly Asn Ala Tyr Tyr
 65                  70                  75                  80

Lys Gln Gly Asp Tyr Asp Glu Ala Ile Glu Tyr Tyr Gln Lys Ala Leu
                 85                  90                  95

Glu Leu Asp Pro Arg Ser Ala Glu Ala Trp Tyr Asn Leu Gly Asn Ala
            100                 105                 110

Tyr Tyr Lys Gln Gly Asp Tyr Asp Glu Ala Ile Glu Tyr Tyr Gln Lys
        115                 120                 125

Ala Leu Glu Leu Asp Pro Arg Ser Ala Glu Ala Trp Tyr Asn Leu Gly
130                 135                 140

Asn Ala Tyr Tyr Lys Gln Gly Asp Tyr Asp Glu Ala Ile Glu Tyr Tyr
145                 150                 155                 160

Gln Lys Ala Leu Glu Leu Asp Pro Arg Ser Ala Glu Ala Trp Tyr Asn
            165                 170                 175

Leu Gly Asn Ala Tyr Tyr Lys Gln Gly Asp Tyr Asp Glu Ala Ile Glu
        180                 185                 190

Tyr Tyr Gln Lys Ala Leu Glu Leu Asp Pro Arg Ser
    195                 200
```

```
<210> SEQ ID NO 144
<211> LENGTH: 612
<212> TYPE: DNA
<213> ORGANISM: Artificial Sequence
<220> FEATURE:
<223> OTHER INFORMATION: CTPR6 WWWWWW

<400> SEQUENCE: 144
gctgaggcat ggtacaacct gggttacgct tactacaaac agggtgacta cgacgaagct    60
atcgaatact accagaaggc tctcgagctg acccgagat ccgctgaggc atggtacaac    120
ctgggttacg cttactacaa acagggtgac tacgacgaag ctatcgaata ctaccagaag    180
gctctcgagc tggacccgag atccgctgag gcatggtaca acctgggtta cgcttactac    240
aaacagggtg actacgacga agctatcgaa tactaccaga aggctctcga gctggacccg    300
agatccgctg aggcatggta caacctgggt tacgcttact acaaacaggg tgactacgac    360
gaagctatcg aatactacca gaaggctctc gagctggacc cgagatccgc tgaggcatgg    420
tacaacctgg gttacgctta ctacaaacag ggtgactacg acgaagctat cgaatactac    480
cagaaggctc tcgagctgga cccgagatcc gctgaggcat ggtacaacct gggttacgct    540
tactacaaac agggtgacta cgacgaagct atcgaatact accagaaggc tctcgagctg    600
gacccgagat cc                                                        612
```

```
<210> SEQ ID NO 145
<211> LENGTH: 13
<212> TYPE: PRT
<213> ORGANISM: Artificial Sequence
<220> FEATURE:
<223> OTHER INFORMATION: H3

<400> SEQUENCE: 145

Ala His Ala Trp His Asn Leu Gly His Ala Tyr Tyr Lys
 1               5                  10
```

<210> SEQ ID NO 146
<211> LENGTH: 39
<212> TYPE: DNA
<213> ORGANISM: Artificial Sequence
<220> FEATURE:
<223> OTHER INFORMATION: H3

<400> SEQUENCE: 146
gctcacgcat ggcacaacct gggtcacgct tactacaaa      39

<210> SEQ ID NO 147
<211> LENGTH: 34
<212> TYPE: PRT
<213> ORGANISM: Artificial Sequence
<220> FEATURE:
<223> OTHER INFORMATION: CTPR1 E2H Y5H N9H

<400> SEQUENCE: 147

Ala His Ala Trp His Asn Leu Gly His Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser

<210> SEQ ID NO 148
<211> LENGTH: 102
<212> TYPE: DNA
<213> ORGANISM: Artificial Sequence
<220> FEATURE:
<223> OTHER INFORMATION: CTPR1 E2H Y5H N9H

<400> SEQUENCE: 148
gctcacgcat ggcacaacct gggtcacgct tactacaaac agggtgacta cgacgaagct      60
atcgaatact accagaaggc tctcgagctg gacccgagat cc      102

<210> SEQ ID NO 149
<211> LENGTH: 34
<212> TYPE: PRT
<213> ORGANISM: Artificial Sequence
<220> FEATURE:
<223> OTHER INFORMATION: CTPR1 R

<400> SEQUENCE: 149

Ala Glu Ala Trp Tyr Asn Leu Gly Asn Ala Tyr Tyr Lys Cys Gly Asp
1               5                   10                  15

Tyr Asp Glu Ala Ile Glu Tyr Tyr Gln Lys Ala Leu Glu Leu Cys Pro
            20                  25                  30

Arg Ser

<210> SEQ ID NO 150
<211> LENGTH: 102
<212> TYPE: DNA
<213> ORGANISM: Artificial Sequence
<220> FEATURE:
<223> OTHER INFORMATION: CTPR1 R

<400> SEQUENCE: 150
gctgaggcat ggtacaacct gggtaacgct tactacaaat gcggtgacta cgacgaagct      60
atcgaatact accagaaggc tctcgagctg tgcccaagat ct      102

```
<210> SEQ ID NO 151
<211> LENGTH: 34
<212> TYPE: PRT
<213> ORGANISM: Artificial Sequence
<220> FEATURE:
<223> OTHER INFORMATION: CTPR1 R1

<400> SEQUENCE: 151

Ala Glu Ala Trp Tyr Asn Leu Gly Asn Ala Tyr Tyr Lys Cys Gly Asp
1               5                   10                  15

Tyr Asp Glu Ala Ile Glu Tyr Tyr Gln Lys Ala Leu Cys Leu Cys Pro
            20                  25                  30

Arg Ser

<210> SEQ ID NO 152
<211> LENGTH: 102
<212> TYPE: DNA
<213> ORGANISM: Artificial Sequence
<220> FEATURE:
<223> OTHER INFORMATION: CTPR1 R1

<400> SEQUENCE: 152
gctgaggcat ggtacaacct gggtaacgct tactacaaat gcggtgacta cgacgaagct      60
atcgaatact accagaaggc tctctgcctg tgcccgagat ct                        102

<210> SEQ ID NO 153
<211> LENGTH: 34
<212> TYPE: PRT
<213> ORGANISM: Artificial Sequence
<220> FEATURE:
<223> OTHER INFORMATION: CTPR1 R2

<400> SEQUENCE: 153

Ala Glu Ala Trp Tyr Asn Leu Gly Asn Ala Tyr Tyr Lys Cys Gly Asp
1               5                   10                  15

Tyr Cys Glu Ala Ile Glu Tyr Tyr Gln Lys Ala Leu Cys Leu Cys Pro
            20                  25                  30

Arg Ser

<210> SEQ ID NO 154
<211> LENGTH: 102
<212> TYPE: DNA
<213> ORGANISM: Artificial Sequence
<220> FEATURE:
<223> OTHER INFORMATION: CTPR1 R2

<400> SEQUENCE: 154
gctgaggcat ggtacaacct gggtaacgct tactacaaat gcggtgacta ctgcgaagct      60
atcgaatact accagaaggc tctctgcctg tgcccgagat ct                        102

<210> SEQ ID NO 155
<211> LENGTH: 117
<212> TYPE: PRT
<213> ORGANISM: Artificial Sequence
<220> FEATURE:
<223> OTHER INFORMATION: CTPR3 WC2W

<400> SEQUENCE: 155

Ala Glu Ala Trp Tyr Asn Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30
```

```
Arg Ser Ala Cys Ala Trp Tyr Cys Leu Gly Cys Ala Tyr Lys Gln
            35                  40                  45

Gly Asp Tyr Asp Glu Ala Ile Glu Tyr Tyr Gln Lys Ala Leu Glu Leu
 50                  55                  60

Asp Pro Arg Ser Ala Glu Ala Trp Tyr Asn Leu Gly Asn Ala Tyr Tyr
 65                  70                  75                  80

Lys Gln Gly Asp Tyr Asp Glu Ala Ile Glu Tyr Tyr Gln Lys Ala Leu
                 85                  90                  95

Glu Leu Asp Pro Arg Ser Ala Glu Ala Lys Gln Asn Leu Gly Asn Ala
                100                 105                 110

Lys Gln Lys Gln Gly
            115
```

<210> SEQ ID NO 156
<211> LENGTH: 351
<212> TYPE: DNA
<213> ORGANISM: Artificial Sequence
<220> FEATURE:
<223> OTHER INFORMATION: CTPR3 WC2W

<400> SEQUENCE: 156

```
gctgaggcat ggtacaacct gggtaacgct tactacaaac agggtgacta cgacgaagct      60
atcgaatact accagaaggc tctcgagctg gacccgagat ccgcttgtgc atggtactgc     120
ctgggttgcg cttactacaa acagggtgac tacgacgaag ctatcgaata ctaccagaag     180
gctctcgagc tggacccgag atccgctgag catggtacaa cctgggtaa cgcttactac      240 aaacagggtg actacgacga agctatcgaa tactaccaga aggctctcga gctggacccg     300
agatctgctg aagctaaaca gaacctgggt aacgctaaac agaaacaggg t              351
```

<210> SEQ ID NO 157
<211> LENGTH: 117
<212> TYPE: PRT
<213> ORGANISM: Artificial Sequence
<220> FEATURE:
<223> OTHER INFORMATION: CTPR3 WC3W

<400> SEQUENCE: 157

```
Ala Glu Ala Trp Tyr Asn Leu Gly Asn Ala Tyr Tyr Lys Gln Gly Asp
 1               5                  10                  15

Tyr Asp Glu Ala Ile Glu Tyr Tyr Gln Lys Ala Leu Glu Leu Asp Pro
             20                  25                  30

Arg Ser Ala Cys Ala Trp Tyr Cys Leu Gly Cys Ala Tyr Leu Cys Gln
            35                  40                  45

Gly Asp Tyr Asp Glu Ala Ile Glu Tyr Tyr Gln Lys Ala Leu Glu Leu
 50                  55                  60

Asp Pro Arg Ser Ala Glu Ala Trp Tyr Asn Leu Gly Asn Ala Tyr Tyr
 65                  70                  75                  80

Lys Gln Gly Asp Tyr Asp Glu Ala Ile Glu Tyr Tyr Gln Lys Ala Leu
                 85                  90                  95

Glu Leu Asp Pro Arg Ser Ala Glu Ala Lys Gln Asn Leu Gly Asn Ala
                100                 105                 110

Lys Gln Lys Gln Gly
            115
```

<210> SEQ ID NO 158
<211> LENGTH: 351
<212> TYPE: DNA
<213> ORGANISM: Artificial Sequence

<220> FEATURE:
<223> OTHER INFORMATION: CTPR3 WC3W

<400> SEQUENCE: 158

```
gctgaggcat ggtacaacct gggtaacgct tactacaaac agggtgacta cgacgaagct    60
atcgaatact accagaaggc tctcgagctg gacccgagat ccgcttgtgc atggtactgc   120
ctgggttgcg cttacctctg ccagggtgac tacgacgaag ctatcgaata ctaccagaag   180
gctctcgagc tggacccgag atccgctgag gcatggtaca acctgggtaa cgcttactac   240
aaacagggtg actacgacga agctatcgaa tactaccaga aggctctcga gctggacccg   300
agatctgctg aagctaaaca gaacctgggt aacgctaaac agaaacaggg t            351
```

<210> SEQ ID NO 159
<211> LENGTH: 117
<212> TYPE: PRT
<213> ORGANISM: Artificial Sequence
<220> FEATURE:
<223> OTHER INFORMATION: CTPR3 WH3W

<400> SEQUENCE: 159

```
Ala Glu Ala Trp Tyr Asn Leu Gly Asn Ala Tyr Tyr Lys Gln Gly Asp
1               5                   10                  15
Tyr Asp Glu Ala Ile Glu Tyr Tyr Gln Lys Ala Leu Glu Leu Asp Pro
            20                  25                  30
Arg Ser Ala His Ala Trp His Asn Leu Gly His Ala Tyr Tyr Lys Gln
        35                  40                  45
Gly Asp Tyr Asp Glu Ala Ile Glu Tyr Tyr Gln Lys Ala Leu Glu Leu
    50                  55                  60
Asp Pro Arg Ser Ala Glu Ala Trp Tyr Asn Leu Gly Asn Ala Tyr Tyr
65                  70                  75                  80
Lys Gln Gly Asp Tyr Asp Glu Ala Ile Glu Tyr Tyr Gln Lys Ala Leu
                85                  90                  95
Glu Leu Asp Pro Arg Ser Ala Glu Ala Lys Gln Asn Leu Gly Asn Ala
            100                 105                 110
Lys Gln Lys Gln Gly
        115
```

<210> SEQ ID NO 160
<211> LENGTH: 351
<212> TYPE: DNA
<213> ORGANISM: Artificial Sequence
<220> FEATURE:
<223> OTHER INFORMATION: CTPR3 WH3W

<400> SEQUENCE: 160

```
gctgaggcat ggtacaacct gggtaacgct tactacaaac agggtgacta cgacgaagct    60
atcgaatact accagaaggc tctcgagctg gacccgagat ccgctcacgc atggcacaac   120
ctgggtcacg cttactacaa acagggtgac tacgacgaag ctatcgaata ctaccagaag   180
gctctcgagc tggacccgag atccgctgag gcatggtaca acctgggtaa cgcttactac   240
aaacagggtg actacgacga agctatcgaa tactaccaga aggctctcga gctggacccg   300
agatctgctg aagctaaaca gaacctgggt aacgctaaac agaaacaggg t            351
```

<210> SEQ ID NO 161
<211> LENGTH: 117
<212> TYPE: PRT
<213> ORGANISM: Artificial Sequence

<220> FEATURE:
<223> OTHER INFORMATION: CTPR3 WRW

<400> SEQUENCE: 161

Ala Glu Ala Trp Tyr Asn Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser Ala Glu Ala Trp Tyr Asn Leu Gly Asn Ala Tyr Tyr Lys Cys
        35                  40                  45

Gly Asp Tyr Asp Glu Ala Ile Glu Tyr Tyr Gln Lys Ala Leu Glu Leu
    50                  55                  60

Cys Pro Arg Ser Ala Glu Ala Trp Tyr Asn Leu Gly Asn Ala Tyr Tyr
65                  70                  75                  80

Lys Gln Gly Asp Tyr Asp Glu Ala Ile Glu Tyr Tyr Gln Lys Ala Leu
                85                  90                  95

Glu Leu Asp Pro Arg Ser Ala Glu Ala Lys Gln Asn Leu Gly Asn Ala
            100                 105                 110

Lys Gln Lys Gln Gly
        115

<210> SEQ ID NO 162
<211> LENGTH: 351
<212> TYPE: DNA
<213> ORGANISM: Artificial Sequence
<220> FEATURE:
<223> OTHER INFORMATION: CTPR3 WRW

<400> SEQUENCE: 162
gctgaggcat ggtacaacct gggtaacgct tactacaaac agggtgacta cgacgaagct      60
atcgaatact accagaaggc tctcgagctg gacccgagat ccgctgaggc atggtacaac     120
ctgggtaacg cttactacaa atgcggtgac tacgacgaag ctatcgaata ctaccagaag     180
gctctcgagc tgtgcccaag atccgctgag gcatggtaca acctgggtaa cgcttactac     240
aaacagggtg actacgacga agctatcgaa tactaccaga aggctctcga gctggacccg     300
agatctgctg aagctaaaca gaacctgggt aacgctaaac agaaacaggg t              351

<210> SEQ ID NO 163
<211> LENGTH: 117
<212> TYPE: PRT
<213> ORGANISM: Artificial Sequence
<220> FEATURE:
<223> OTHER INFORMATION: CTPR3 WR1W

<400> SEQUENCE: 163

Ala Glu Ala Trp Tyr Asn Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser Ala Glu Ala Trp Tyr Asn Leu Gly Asn Ala Tyr Tyr Lys Cys
        35                  40                  45

Gly Asp Tyr Asp Glu Ala Ile Glu Tyr Tyr Gln Lys Ala Leu Cys Leu
    50                  55                  60

Cys Pro Arg Ser Ala Glu Ala Trp Tyr Asn Leu Gly Asn Ala Tyr Tyr
65                  70                  75                  80

Lys Gln Gly Asp Tyr Asp Glu Ala Ile Glu Tyr Tyr Gln Lys Ala Leu
                85                  90                  95

```
Glu Leu Asp Pro Arg Ser Ala Glu Ala Lys Gln Asn Leu Gly Asn Ala
            100                 105                 110

Lys Gln Lys Gln Gly
        115

<210> SEQ ID NO 164
<211> LENGTH: 351
<212> TYPE: DNA
<213> ORGANISM: Artificial Sequence
<220> FEATURE:
<223> OTHER INFORMATION: CTPR3 WR1W

<400> SEQUENCE: 164
gctgaggcat ggtacaacct gggtaacgct tactacaaac agggtgacta cgacgaagct    60
atcgaatact accagaaggc tctcgagctg acccgagat  ccgctgaggc atggtacaac   120
ctgggtaacg cttactacaa atgcggtgac tacgacgaag ctatcgaata ctaccagaag   180
gctctctgcc tgtgcccgag atccgctgag gcatggtaca acctgggtaa cgcttactac   240
aaacagggtg actacgacga agctatcgaa tactaccaga aggctctcga gctggacccg   300
agatctgctg aagctaaaca gaacctgggt aacgctaaac agaaacaggg t            351

<210> SEQ ID NO 165
<211> LENGTH: 117
<212> TYPE: PRT
<213> ORGANISM: Artificial Sequence
<220> FEATURE:
<223> OTHER INFORMATION: CTPR3 WR2W

<400> SEQUENCE: 165

Ala Glu Ala Trp Tyr Asn Leu Gly Asn Ala Tyr Tyr Lys Gln Gly Asp
1               5                   10                  15

Tyr Asp Glu Ala Ile Glu Tyr Tyr Gln Lys Ala Leu Glu Leu Asp Pro
            20                  25                  30

Arg Ser Ala Glu Ala Trp Tyr Asn Leu Gly Asn Ala Tyr Tyr Lys Cys
        35                  40                  45

Gly Asp Tyr Cys Glu Ala Ile Glu Tyr Tyr Gln Lys Ala Leu Cys Leu
    50                  55                  60

Cys Pro Arg Ser Ala Glu Ala Trp Tyr Asn Leu Gly Asn Ala Tyr Tyr
65                  70                  75                  80

Lys Gln Gly Asp Tyr Asp Glu Ala Ile Glu Tyr Tyr Gln Lys Ala Leu
                85                  90                  95

Glu Leu Asp Pro Arg Ser Ala Glu Ala Lys Gln Asn Leu Gly Asn Ala
            100                 105                 110

Lys Gln Lys Gln Gly
        115

<210> SEQ ID NO 166
<211> LENGTH: 351
<212> TYPE: DNA
<213> ORGANISM: Artificial Sequence
<220> FEATURE:
<223> OTHER INFORMATION: CTPR3 WR2W

<400> SEQUENCE: 166
gctgaggcat ggtacaacct gggtaacgct tactacaaac agggtgacta cgacgaagct    60
atcgaatact accagaaggc tctcgagctg acccgagat  ccgctgaggc atggtacaac   120
ctgggtaacg cttactacaa atgcggtgac tactgcgaag ctatcgaata ctaccagaag   180
gctctctgcc tgtgcccgag atccgctgag gcatggtaca acctgggtaa cgcttactac   240
```

```
aaacagggtg actacgacga agctatcgaa tactaccaga aggctctcga gctggacccg    300
agatctgctg aagctaaaca gaacctgggt aacgctaaac agaaacaggg t             351
```

```
<210> SEQ ID NO 167
<211> LENGTH: 13
<212> TYPE: PRT
<213> ORGANISM: Artificial Sequence
<220> FEATURE:
<223> OTHER INFORMATION: amino acid sequence
<220> FEATURE:
<221> NAME/KEY: VARIANT
<222> LOCATION: (2)..(2)
<223> OTHER INFORMATION: E, H, C or D
<220> FEATURE:
<221> NAME/KEY: VARIANT
<222> LOCATION: (5)..(5)
<223> OTHER INFORMATION: Y, H, C, D or E
<220> FEATURE:
<221> NAME/KEY: VARIANT
<222> LOCATION: (9)..(9)
<223> OTHER INFORMATION: N, H, C, D or E
<220> FEATURE:
<221> NAME/KEY: VARIANT
<222> LOCATION: (12)..(12)
<223> OTHER INFORMATION: Y, H, L, A, V, C, D or E
<220> FEATURE:
<221> NAME/KEY: VARIANT
<222> LOCATION: (13)..(13)
<223> OTHER INFORMATION: K, H, C, D or E

<400> SEQUENCE: 167

Ala Xaa Ala Trp Xaa Asn Leu Gly Xaa Ala Tyr Xaa Xaa
1               5                   10

<210> SEQ ID NO 168
<211> LENGTH: 13
<212> TYPE: PRT
<213> ORGANISM: Artificial Sequence
<220> FEATURE:
<223> OTHER INFORMATION: amino acid sequence
<220> FEATURE:
<221> NAME/KEY: VARIANT
<222> LOCATION: (2)..(2)
<223> OTHER INFORMATION: E, H, C or D
<220> FEATURE:
<221> NAME/KEY: misc_feature
<222> LOCATION: (9)..(9)
<223> OTHER INFORMATION: Xaa can be any naturally occurring amino acid

<400> SEQUENCE: 168

Ala Xaa Ala Trp Tyr Asn Leu Gly Xaa Ala Tyr Tyr Lys
1               5                   10

<210> SEQ ID NO 169
<211> LENGTH: 13
<212> TYPE: PRT
<213> ORGANISM: Artificial Sequence
<220> FEATURE:
<223> OTHER INFORMATION: amino acid sequence

<400> SEQUENCE: 169

Ala Cys Ala Trp Tyr His Leu Gly Asn Ala Tyr Tyr Lys
1               5                   10

<210> SEQ ID NO 170
<211> LENGTH: 13
<212> TYPE: PRT
<213> ORGANISM: Artificial Sequence
<220> FEATURE:
<223> OTHER INFORMATION: amino acid sequence
```

```
<400> SEQUENCE: 170

Ala Cys Ala Trp Tyr Asn Leu Gly His Ala Tyr Tyr Lys
1               5                   10
```

METAL NANOCLUSTER SCAFFOLDS

CROSS REFERENCE TO RELATED APPLICATIONS

This is a National Stage application filed under 35 U.S.C. § 371 of International Application PCT/EP2018/068710 filed on Jul. 10, 2018, which designated the United States of America, the disclosure of which is incorporated herein by reference in the entirety and for all purposes. This application claims the benefit of priority to European Patent Application EP 17382451.7, filed on Jul. 11, 2017.

TECHNICAL FIELD

The project leading to this application has received funding from the European Research Council (ERC) under the European Union's Horizon 2020 research and innovation programme (grant agreement No 648071).

The present invention relates in general to the field of nanoclusters of metal atoms stabilized by short peptide sequences. In particular, the present invention provides, among others, these short peptide sequences, as well as nanoclusters that comprise them, a process for the preparation of these nanoclusters, and uses thereof.

BACKGROUND ART

Metal nanoclusters (NCs) have attracted special attention in recent years due to their unique properties, which are substantially different from those of bulk metal and classical metallic nanoparticles.

Metal NCs are small metal atom assemblies consisting of a few to hundreds of metal atoms and having a size less than 2 nm. Noble metal NCs show discrete, size-tunable electronic transitions and a strong fluorescence emission due to the strong quantum-confinement effect. Due to, among other factors, the fact that electrons of the metal atoms are confined in such small molecular dimensions and to the special discrete energy levels, metal NCs exhibit special optical, electronical and chemical properties, including strong photoluminescence, excellent photostability, good biocompatibility and sub-nanometer size. They show fluorescence over the ultraviolet to near infrared region. Metal NCs have been used as sensors (for example for temperature and pH), as bioimaging tools, in the detection of biomolecules, proteins, nucleic acids and metal ions and as drug delivery systems among others (cfr. Qu X et al. 2015, Li J et al. 2014 and Shang L et al. 2011).

To date, significant efforts have been made to develop gold (Au) and silver (Ag) NCs. On the contrary, reports on the synthesis of copper (Cu) NCs are still scarce because of the difficulty in preparing extremely tiny particles (for example in Huang H et al. 2014 the diameter of the cooper NC is 1.7 nm) and of their susceptibility to oxidation. The latter is of relevance because nanoclusters have to be stable in aqueous medium for biological applications.

It has been reported that metal NCs can be stabilized by including molecules such as particular dendrimers, small molecules, DNA, peptides and proteins. Proteins such as bovine serum albumin (BSA), papain, human transferrin, lysozyme, trypsin, pepsin, insulin, and peroxidase have been employed in the preparation of metal NCs (see for example Xie J et al. 2009, Huang H et al. 2014 and Li J et al. 2014). Nevertheless the methods used normally cause the denaturalization of the secondary or tertiary structure of the proteins which affect the function of said proteins. Alternatively, it has been proposed the use of proteins, with particular sequence motif repetitions as templates for the synthesis and stabilization of metal NCs, for example the consensus tetratricopeptide repeat (CTPR) module, a 34 amino acids helix-turn-helix motif (D'Andrea L et al. 2003) has also been disclosed in the state of the art as useful in gold NC formation as it seems to confer a certain stability (Couleaud P et al. 2015).

In spite of the efforts made, there is the need of protein templates useful as scaffolds for preparing small stable metal nanoclusters that can be used with a wide variety of metals for use in biological applications, while the protein template retains its biological functionality.

SUMMARY OF INVENTION

The present inventors have produced CTPR variant motifs which provide protein templates useful as efficient scaffolds, providing NCs with higher fluorescence intensity, stability (in particular photostability) and with the ability of being cell-internalized while retaining the biological properties of the protein template.

In particular, the present inventors have surprisingly found that when particular amino acid residues of the CTPR's region A sequence SEQ ID NO: 19 were replaced by histidine (His, H) or cysteine (Cys, C), the synthesis of remarkably stabilized Cu NCs, Au NCs and Ag NCs were achieved (examples below).

The inventors have found that the results obtained using His or Cys can be also obtained by replacing the particular positions of the CTPR's region A sequence SEQ ID NO: 19 by glutamic acid (Glu, E) or aspartic acid (Asp, D), as these four amino acids (that is, H, C, D and E) coordinate metal ions.

The present inventors also found that when these variant motifs were included in a protein, that inclusion did not negatively affect to the activity of the protein. The specific ligand binding or recognition activity of the protein was conserved when the protein was stabilizing the NC, as the same ligand affinity values were maintained (as indicated by the dissociation constant (Kd)). Consequently, both the resulting protein as well as the nanocluster showed their respective activities.

Thus, in a first aspect the present invention provides an amino acid sequence consisting of sequence SEQ ID NO: 1 or a salt thereof:

(SEQ ID NO: 1)
$AX_1AWX_2X_3LGX_4AYX_5X_6$ wherein
$X_1$ is an amino acid selected from E, H, C, and D;
$X_2$ is an amino acid selected from Y, H, C, D and E;
$X_3$ is an amino acid selected from N, H, C, D and E;
$X_4$ is an amino acid selected from N, H, C, D and E;
$X_5$ is an amino acid selected from Y, H, L, A, V, C, D and E;
$X_6$ is an amino acid selected from K, H, C, D and E;
provided that at least two of $X_1$, $X_2$, $X_3$, $X_4$, $X_5$ and $X_6$ are the same or different and represent H, C, D or E.

In a further aspect the present invention provides an amino acid sequence consisting of sequence SEQ ID NO: 1 or a salt thereof:

(SEQ ID NO: 1)
$AX_1AWX_2X_3LGX_4AYX_5X_6$ wherein
$X_1$ is an amino acid selected from E, H, C, and D;
$X_2$ is an amino acid selected from Y, H, C, D and E;

$X_3$ is an amino acid selected from N, H, C, D and E;
$X_4$ is an amino acid selected from N, H, C, D and E;
$X_5$ is an amino acid selected from Y, H, L, A, V, C, D and E;
$X_6$ is an amino acid selected from K, H, C, D and E;
provided that:
at least two of $X_1$ to $X_6$ are the same or different and represent H, C, D or E;
when $X_2$ is H, C, D or E, then $X_3$ is N; and,
when $X_3$ is H, C, D or E, then $X_2$ is Y.

Without being bound to the theory the inventors believe that the binding (coupling) of the metal with the peptide or the protein of the present invention occurs through residues $X_{1-6}$ as defined above and this is what confers a surprising stabilization effect to the resulting metallic nanocluster.

In a second aspect, the present invention provides a peptide of formula (I) or a salt thereof

$$Z—(B)n\text{-}F\text{-}(G)m \qquad (I)$$

wherein n and m is 0 or 1,
Z represents the amino acid sequence according to the first aspect of the invention, provided that when $X_1$ is C, then $X_4$ is C, D, E or N,
B represents a linker,
F is an amino acid sequence having an alpha helix secondary motif, and
G is a sequence selected from the group consisting of: SEQ ID NO: 23, SEQ ID NO: 24 and SEQ ID NO: 25.

In a third aspect, the present invention provides a protein of general formula (II) or a salt thereof:

$$W_n Z_p W_q \qquad (II)$$

wherein
n and q represent integers with a value from 0 to 10, and p represents an integer with a value from 1 to 10, provided that n+p+q is equal or higher than 2,
W is a peptide comprising the sequence SEQ ID NO: 37, AEAWYNLGNAYYKQGDYDEAIEYYQKA-LELDPRS, and
Z is an amino acid sequence according to the first aspect of the invention or an amino acid sequence that comprises the peptide according to the second aspect of the invention.

In a fourth aspect, the present invention provides a nucleic acid sequence coding for the amino acid sequence according to the first aspect of the invention or for the peptide according to the second aspect of the invention or for the protein according to the third aspect of the invention.

In a fifth aspect, the present invention provides an expression cassette comprising the nucleic acid sequence according to the fourth aspect of the invention.

In a sixth aspect, the present invention provides a nucleic acid vector comprising the nucleic acid sequence according to the fourth aspect of the invention or the expression cassette according to the fifth aspect of the invention.

In a seventh aspect, the present invention provides a host cell comprising the amino acid sequence according to the first aspect of the invention, the peptide according to the second aspect of the invention, the protein according to the third aspect of the invention, the nucleic acid sequence according to the fourth aspect of the invention, the expression cassette according to the fifth aspect of the invention or the nucleic acid vector according to the sixth aspect of the invention.

In an eighth aspect, the present invention provides the use of the amino acid sequence according to the first aspect of the invention, the peptide according to the second aspect of the invention or the protein according to the third aspect of the invention as metal nanocluster scaffold.

In a ninth aspect, the present invention provides a metal nanocluster comprising the amino acid sequence according to the first aspect of the invention, the peptide according to the second aspect of the invention or the protein according to the third aspect of the invention.

In a tenth aspect, the present invention provides a combination of at least two metal nanoclusters according to the ninth aspect of the invention.

In an eleventh aspect, the present invention provides a process for the production of a metal nanocluster according to the ninth aspect of the invention comprising the step of (a) mixing the protein as defined in the third aspect of the invention with a metal containing compound; and (b) subjecting the mixture to a reduction reaction. Advantageously, due to the particular nature of the peptide motifs of the invention, the process of the invention does not require the denaturalization of the protein acting as scaffold, on which the NC is formed, which simplifies the preparation of NCs.

A twelfth aspect of the present invention refers to the metal nanocluster obtainable by the process of the eleventh aspect of the invention.

As it has been mentioned above, the amino acid sequences and peptides of the invention allow designing proteins which, when used as scaffolds, enhance the intrinsic properties of the metal NC due to their stabilization effect.

In a thirteenth aspect, the present invention provides the use of the metal nanocluster according to the ninth aspect of the invention or the combination of metal nanoclusters according to the tenth aspect of the invention or the metal nanoclusters according to the twelfth aspect of the invention as imaging agent, as drug-delivery carrier, as metabolic interfering agent, as catalyst, as an analyte, for phasing crystallographic data set, as cell labeling agent, as specific protein labeling agent, as biosensor, as a temperature sensor, as photosensitizer, or for the manufacture of an optoelectronic device.

In a fourteenth aspect, the present invention provides a kit comprising the amino acid sequence according to the first aspect of the invention or the peptide according to the second aspect of the invention or the protein according to the third aspect of the invention or the nucleic acid sequence according to fourth aspect of the invention or the expression cassette according to the fifth aspect of the invention or the nucleic acid vector of the sixth aspect of the invention or the host cell according to the seventh aspect of the invention or the metal nanocluster of the ninth aspect of the invention or the combination of metal nanoclusters according to the tenth aspect of the invention or the metal nanoclusters according to the twelfth aspect of the invention.

In a fifteenth aspect, the present invention provides the use of a kit comprising the amino acid sequence according to the first aspect of the invention or the peptide according to the second aspect of the invention or the protein according to the third aspect of the invention or the nucleic acid sequence according to the fourth aspect of the invention or the expression cassette according to the fifth aspect of the invention or the nucleic acid vector according to the sixth aspect of the invention or the host cell according to the seventh aspect of the invention for the preparation of a metal nanocluster according to the ninth aspect of the invention or the metal nanoclusters according to the twelfth aspect of the invention.

In a sixteenth aspect the present invention provides a device comprising the metal nanocluster according to the ninth aspect or the combination of metal nanoclusters according to the tenth aspect or the metal nanoclusters according to the twelfth aspect of the invention.

Finally, in a last aspect the present invention provides the metal NC of the ninth or twelfth aspect of the invention or the combination of the tenth aspect of the invention for use in diagnosis or prognosis.

DETAILED DESCRIPTION OF THE INVENTION

Figure 1:
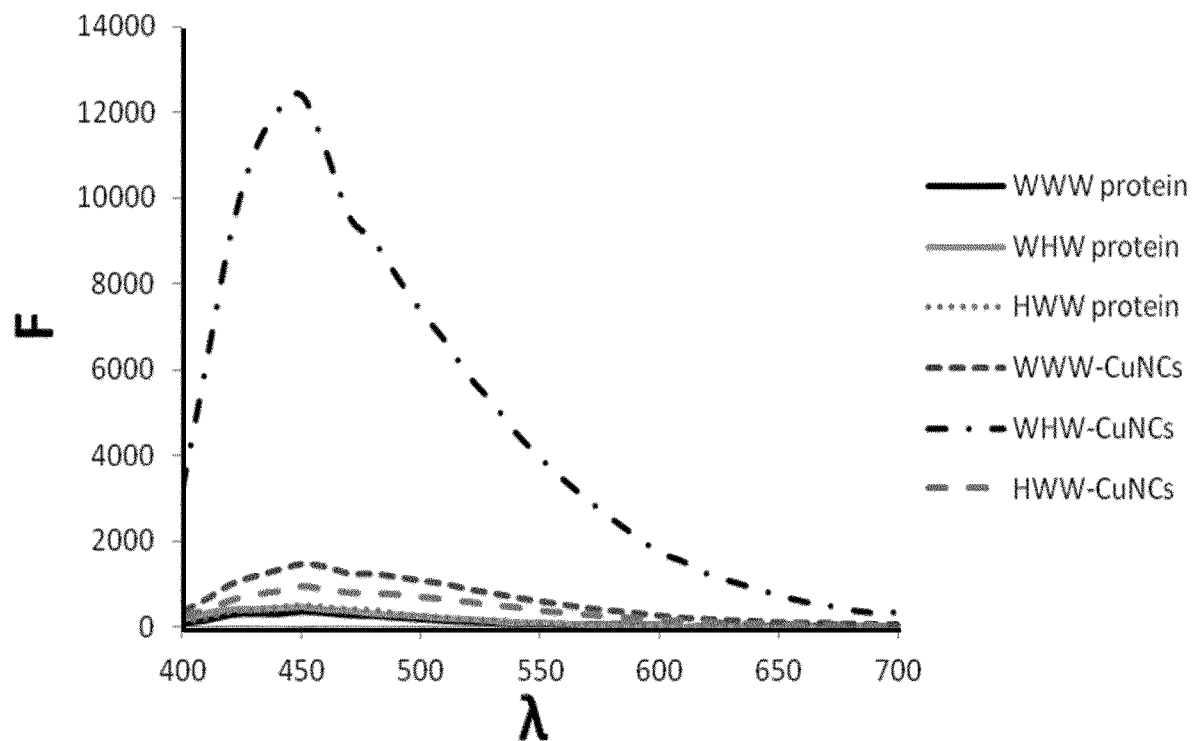
FIG. 1 fluorescence spectra showing the effect of the presence and the position of the His clamp in CuNCs (F: Fluorescence intensity (arbitrary units); λ: wavelength (nm)).

In a first aspect the present invention provides a peptide of sequence SEQ ID NO: 1 or a salt thereof.

The amino acids forming any of the amino acid sequences, peptides or proteins of the invention, unless otherwise stated, can have D- or L-configuration.

There is no limitation regarding the salts, except that if used for therapeutic purposes, they must be pharmaceutically acceptable. In one embodiment, the salt is a pharmaceutically acceptable salt. As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, trifluoroacetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, and ammonium. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counter ions such as halide, hydroxide, carboxylate, sulfate, phosphate, nitrate, lower alkyl sulfonate and aryl sulfonate.

For the purposes of the invention, any ranges given include both the lower and the upper end-points of the range. Ranges given, such as temperatures, times, and the like, should be considered approximate, unless specifically stated.

In one embodiment of the first aspect of the invention, optionally in combination with any of the embodiments provided below, at least two, three, four, five or six of $X_1$ to $X_6$ are the same or different and represent H, C, D or E.

In one embodiment of the first aspect of the invention, optionally in combination with any of the embodiments provided above or below, $X^1$ is an amino acid selected from E, H and C; $X_2$ is an amino acid selected from Y, H and C; $X_3$ is an amino acid selected from N, H and C; $X_4$ is an amino acid selected from N, H and C; $X_5$ is an amino acid selected from Y, H, L, A, V and C; and $X_6$ is an amino acid selected from K, H and C; provided that at least two of $X_1$ to $X_6$ are the same or different and represent H or C; in another embodiment at least three, four, five or six of $X_1$ to $X_6$ are the same or different and represent H or C.

In one embodiment of the first aspect of the invention, optionally in combination with any of the embodiments provided below, $X_1$ is an amino acid selected from E, H and C; $X_2$ is an amino acid selected from Y, H and C; $X_3$ is an amino acid selected from N, H and C; $X_4$ is an amino acid selected from N, H and C; $X_5$ is an amino acid selected from Y, H, L, A, V and C; and $X_6$ is an amino acid selected from K, H and C; provided that:
- at least two of $X_1$ to $X_6$ are the same or different and represent H or C;
- when $X_2$ is H or C, then $X_3$ is N;
- when $X_3$ is H or C, then $X_2$ is Y; and
- when $X_6$ is H or C, then $X_5$ is L, A or V.

In another embodiment of the first aspect of the invention, optionally in combination with any of the embodiments provided above or below, $X_6$ is K.

In another embodiment of the first aspect of the invention, optionally in combination with any of the embodiments provided above or below, when $X_1$ is E, then at least two of $X_2$, $X_3$, $X_4$, $X_5$ and $X_6$ are the same or different and represent H, C, D or E. In another embodiment at least three, four or five of $X_2$, $X_3$, $X_4$, $X_5$ and $X_6$ are the same or different and represent H, C, D or E; in another embodiment at least two, three, four or five of $X_2$, $X_3$, $X_4$, $X_5$ and $X_6$ are the same or different and represent H or C.

In another embodiment of the first aspect of the invention, the amino acid sequence is selected from the group consisting of: $AX_1AWX_2NLGNAYYK$ (SEQ ID NO: 2); $AX_1AWYX_3LGNAYYK$ (SEQ ID NO: 3); $AEAWX_2NLGX_4AYYK$ (SEQ ID NO: 4); $AEAWYX_3LGX_4AYYK$ (SEQ ID NO: 5); $AEAWYNLGX_4AYX_5K$ (SEQ ID NO: 6); $AX_1AWX_2NLGX_4AYYK$ (SEQ ID NO: 7); $AX_1AWYX_3LGX_4AYYK$ (SEQ ID NO: 8); $AEAWX_2NLGX_4AYX_5K$ (SEQ ID NO: 9); $AEAWYX_3LGX_4AYX_5K$ (SEQ ID NO: 10); $AX_1AWX_2NLGX_4AYX_5K$ (SEQ ID NO: 11); $AX_1AWYX_3LGX_4AYX_5K$ (SEQ ID NO: 12); and $AX_1AWYX_3LGX_4AYX_5X_6$ (SEQ ID NO: 13). Particularly, the amino acid sequence is selected from the group consisting of $AX_1AWYX_3LGNAYYK$ (SEQ ID NO: 3), $AEAWX_2NLGX_4AYYK$ (SEQ ID NO: 4); $AX_1AWYX_3LGX_4AYYK$ (SEQ ID NO: 8); and $AX_1AWYX_3LGX_4AYX_5X_6$ (SEQ ID NO: 13).

In another embodiment of the first aspect of the invention, the amino acid sequence is selected from the group consisting of: $AX_1AWX_2NLGNAYYK$ (SEQ ID NO: 2); $AX_1AWYX_3LGNAYYK$ (SEQ ID NO: 3); $AEAWX_2NLGX_4AYYK$ (SEQ ID NO: 4); $AEAWYX_3LGX_4AYYK$ (SEQ ID NO: 5); $AEAWYNLGX_4AYX_5K$ (SEQ ID NO: 6); $AX_1AWX_2NLGX_4AYYK$ (SEQ ID NO: 7); $AX_1AWYX_3LGX_4AYYK$ (SEQ ID NO: 8); $AEAWX_2NLGX_4AYX_5K$ (SEQ ID NO: 9); $AEAWYX_3LGX_4AYX_5K$ (SEQ ID NO: 10); $AX_1AWX_2NLGX_4AYX_5K$ (SEQ ID NO: 11); $AX_1AWYX_3LGX_4AYX_5K$ (SEQ ID NO: 12); $AX_1AWYX_3LGX_4AYX_5X_6$ (SEQ ID NO: 13), $AX_1AWX_2NLGX_4AYYX_6$ (SEQ ID NO: 110); $AEAWX_2NLGX_4AYYX_6$ (SEQ ID NO: 111); $AEAWYX_3LGX_4AYYX_6$ (SEQ ID NO: 112); $AEAWYNLGX_4AYYX_6$ (SEQ ID NO: 113), $AX_1AWX_2X_3LGX_4AYYK$ (SEQ ID NO: 114), $AX_1AWX_2NLGX_4AYX_5X_6$ (SEQ ID NO: 167), and $AX_1AWYNLGX_4AYYK$ (SEQ ID NO: 168).

In another embodiment of the first aspect of the invention, optionally in combination with any of the embodiments provided above or below, $X_1$ to $X_6$ are the same and represent C or H.

In another embodiment of the first aspect of the invention, the amino acid sequence is selected from the group consisting of ACAWYCLGNAYYK (SEQ ID NO: 14), AEAWHNLGHAYYK (SEQ ID NO: 15); AEAWCNLGCAYYK (SEQ ID NO: 16); ACAWYCLGCAYYK (SEQ ID NO: 17); and ACAWYCLGCAYLC (SEQ ID NO: 18).

In another embodiment of the first aspect of the invention, the amino acid sequence is selected from the group consisting of ACAWYCLGNAYYK (SEQ ID NO: 14), AEAWHNLGHAYYK (SEQ ID NO: 15); AEAWCNLGCAYYK (SEQ ID NO: 16); ACAWYCLGCAYYK (SEQ ID NO: 17); and ACAWYCLGCAYLC (SEQ ID NO: 18); AHAWHHLGHAYYK (SEQ ID NO: 115); AHAWHNLGHAYLH (SEQ ID NO: 117; and AHAWHNLGHAYYK (SEQ ID NO: 145).

In another embodiment of the first aspect of the invention, the amino acid sequence is selected from the group consisting of ACAWYCLGNAYYK (SEQ ID NO: 14), AEAWHNLGHAYYK (SEQ ID NO: 15); AEAWCNLGCAYYK (SEQ ID NO: 16); ACAWYCLGCAYYK (SEQ ID NO: 17); and ACAWYCLGCAYLC (SEQ ID NO: 18); AHAWHHLGHAYYK (SEQ ID NO:115); AHAWHNLGHAYLH (SEQ ID NO: 117, AHAWHNLGHAYYK (SEQ ID NO: 145), ACAWYHLG-NAYYK (SEQ ID NO: 169), and ACAWYNLGHAYYK (SEQ ID NO: 170).

In a second aspect, the present invention provides a peptide of formula (I) or a salt thereof.

In one embodiment of the second aspect of the invention, optionally in combination with any of the embodiments provided above or below, the amino acid sequence has an alpha helix secondary motif ("F") which is of sequence SEQ ID NO: 20, SEQ ID NO: 21 or SEQ ID NO: 22.

In another embodiment of the second aspect of the invention, optionally in combination with any of the embodiments provided above or below, m is 1. In another embodiment of the second aspect of the invention, optionally in combination with any of the embodiments provided above or below n and m are 1.

In another embodiment of the second aspect of the invention, optionally in combination with any of the embodiments provided above or below, the linker "B" is an amino acid sequence QGD.

In another embodiment of the second aspect of the invention, optionally in combination with any of the embodiments provided above or below, the sequence "G" can be any sequence of four amino acids provided that its second amino acid is a proline. In a preferred embodiment "G" is SEQ ID NO: 23, SEQ ID NO: 24 or SEQ ID NO: 25. In a more preferred embodiment is SEQ ID NO: 23.

In another embodiment of the second aspect of the invention, optionally in combination with any of the embodiments provided above or below, the sequence bound to the C-terminal end of Z ("BFG" in formula (I)) is SEQ ID NO 26: QGDYDEAIEYYQKALELDPRS.

In another embodiment of the second aspect of the invention, optionally in combination with any of the embodiments provided above or below, the peptide is selected from the group consisting of:

```
                                           (SEQ ID NO: 27)
AEAWHNLGHAYYKQGDYDEAIEYYQKALELDPRS, (SEQ ID NO: 29)
AEAWCNLGCAYYKQGDYDEAIEYYQKALELDPRS, (SEQ ID NO: 31)
ACAWYCLGNAYYKQGDYDEAIEYYQKALELDPRS, (SEQ ID NO: 33)
ACAWYCLGCAYYKQGDYDEAIEYYQKALELDPRS
and, (SEQ ID NO: 35)
ACAWYCLGCAYLCQGDYDEAIEYYQKALELDPRS.
```

In another embodiment of the second aspect of the invention, optionally in combination with any of the embodiments provided above or below, the peptide is selected from the group consisting of:

```
                                           (SEQ ID NO: 27)
AEAWHNLGHAYYKQGDYDEAIEYYQKALELDPRS, (SEQ ID NO: 29)
AEAWCNLGCAYYKQGDYDEAIEYYQKALELDPRS, (SEQ ID NO: 31)
ACAWYCLGNAYYKQGDYDEAIEYYQKALELDPRS, (SEQ ID NO: 33)
ACAWYCLGCAYYKQGDYDEAIEYYQKALELDPRS, (SEQ ID NO: 35)
ACAWYCLGCAYLCQGDYDEAIEYYQKALELDPRS, (SEQ ID NO: 119)
AHAWHHLGHAYYKQGDYDEAIEYYQKALELDPRS, (SEQ ID NO: 121)
AHAWHNLGHAYLHQGDYDEAIEYYQKALELDPRS,
and (SEQ ID NO: 147)
AHAWHNLGHAYYKQGDYDEAIEYYQKALELDPRS.
```

In another embodiment of the second aspect of the invention, optionally in combination with any of the embodiments provided above or below, the peptide is selected from

```
                                           (SEQ ID NO: 27)
AEAWHNLGHAYYKQGDYDEAIEYYQKALELDPRS, (SEQ ID NO: 29)
AEAWCNLGCAYYKQGDYDEAIEYYQKALELDPRS, (SEQ ID NO: 31)
ACAWYCLGNAYYKQGDYDEAIEYYQKALELDPRS, (SEQ ID NO: 33)
ACAWYCLGCAYYKQGDYDEAIEYYQKALELDPRS, (SEQ ID NO: 35)
ACAWYCLGCAYLCQGDYDEAIEYYQKALELDPRS, (SEQ ID NO: 97)
ACAWYHLGNAYYKQGDYDEAIEYYQKALELDPRS, (SEQ ID NO: 99)
ACAWYNLGHAYYKQGDYDEAIEYYQKALELDPRS, (SEQ ID NO: 119)
AHAWHHLGHAYYKQGDYDEAIEYYQKALELDPRS, (SEQ ID NO: 121)
AHAWHNLGHAYLHQGDYDEAIEYYQKALELDPRS,
and (SEQ ID NO: 147)
AHAWHNLGHAYYKQGDYDEAIEYYQKALELDPRS.
```

In a third aspect the present invention provides a protein of formula (II).

In one embodiment of the third aspect of the invention, optionally in combination with any of the embodiments provided above or below, W is of sequence SEQ ID NO: 37.

In another embodiment of the third aspect of the invention, optionally in combination with any of the embodiments provided above or below, Z is a peptide as defined in the second aspect of the invention.

In another embodiment of the third aspect of the invention, optionally in combination with any of the embodiments provided above or below, n and q are the same or different and they are different from 0.

In another embodiment of the third aspect of the invention, optionally in combination with any of the embodiments provided above or below, p is 1, 2, 3, 4, 5 or 6.

In another embodiment of the third aspect of the invention, optionally in combination with any of the embodiments provided above or below, the protein is of general formula (II):

$$WZ_pW \qquad (II)$$

wherein W, Z and p are as defined above.

In another embodiment of the third aspect of the invention, the protein is selected from the group consisting of: SEQ ID NO: 43, SEQ ID NO: 45, SEQ ID NO: 47, SEQ ID NO: 49, SEQ ID NO: 51, SEQ ID NO: 53, SEQ ID NO:55, SEQ ID NO: 57, SEQ ID NO: 59, SEQ ID NO: 61, SEQ ID NO: 63, SEQ ID NO: 65, SEQ ID NO: 67, SEQ ID NO: 101, SEQ ID NO: 103, SEQ ID NO: 105, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141 SEQ ID NO: 155, SEQ ID NO: 157 and SEQ ID NO: 159.

In another embodiment of the third aspect of the invention, optionally in combination with any of the embodiments provided above or below, the protein is bound to an element selected from the group consisting of: a peptide, a nanoparticle, a nucleic acid, an inorganic molecule, an organic molecule, a lipid, a monosaccharide, an oligosaccharide, an enzyme, an antibody, an antigen, a tag peptide, an imaging agent such as a MRI contrast agent, a PET contrast agent, a coordinating metal contrast agent, and any combination thereof.

The peptide that can be bound to the proteins of the third aspect of the invention allows the directionalization of said protein, for example to cellular nucleus, cellular membrane; or is a translocation peptide.

The tag peptide that can be bound to the proteins of the third aspect of the invention, can be for example the peptide MEEVF (SEQ ID NO: 109), a His-tag peptide or any tag peptide known by the expert. It can also be a tag peptide that allows the binding of the NC to an organelle of interest inside a cell.

As illustration, the NCs of the invention, due to their fluorescent properties, can be used as labelling agents of nucleic acids, allowing the detection of the presence or absence of a specific epigenetics modification or alternatively a genetic mutation, such as point mutations (SNPs, polymorphisms), deletions or insertions.

The term "antibody" is used herein in the sense of its capacity to bind specifically to an antigen and thus, it refers to a molecule having such capacity. Included within said term are: an intact antibody that binds specifically to the target antigen; and an antibody fragment that binds specifically to the target antigen.

As used herein, the term "intact antibody" refers to an immunoglobulin molecule capable of specific binding to its cognate target, including a target, such as a carbohydrate, polynucleotide, lipid, polypeptide, etc., through at least one binding recognition site (e.g., antigen binding site), including a site located in the variable region of the immunoglobulin molecule. An antibody includes an antibody of any class, namely IgA, IgD, IgE, IgG (or sub-classes thereof), and IgM. In a preferred embodiment, the antibody is an IgG.

As used herein, the term "antibody fragment" refers to functional fragments of antibodies, such as Fab, Fab', F(ab')2, Fv, single chain (scFv), heavy chain or fragment thereof, light chain or fragment thereof, a domain antibody (DAb) (i.e., the variable domain of an antibody heavy chain (VH domain) or the variable domain of the antibody light chain (VL domain)) or dimers thereof, VH or dimers thereof, VL or dimers thereof, nanobodies (camelid VH), and functional variants thereof, fusion proteins comprising an antibody, or any other modified configuration of the immunoglobulin molecule that comprises an antigen recognition site of a desired specificity. An antibody fragment may refer to an antigen-binding fragment. In a preferred embodiment, the antibody fragment is a VH or domain antibody or DAb. In another preferred embodiment, the antibody fragment is a scFv. In another preferred embodiment, the antibody fragment is a nanobody.

Techniques for the preparation and use of the various antibodies are well known in the art. For example, fully human monoclonal antibodies lacking any non-human sequences can be prepared from human immunoglobulin transgenic mice or from phage display libraries.

In a particular aspect of the present invention the antibody is an antibody which specifically binds to an antigen exposed on the cell surface.

The term "imaging agent" refers to a chemical compound that is designed to allow the localization of the target cell. Non-limitative examples of imaging agents suitable for the purposes of this invention include radionuclides, fluorophores, magnetic resonance imaging (MRI) contrast agent, positron emission tomography (PET) contrast agents, coordinating metals giving signals as contrast agent, or any combination thereof.

The term "magnetic contrast agent" or "MRI agent", as used herein, refers to a group of contrast media used to improve the visibility of internal body structures in magnetic resonance imaging (MRI). Examples of MRI agents include, without limitation, gadolinium and other lanthanides-based compounds, superparamagnetic iron oxide (SPIO) and ultra-small superparamagnetic iron oxide (USPIO), iron platinum-based compounds and manganese based compounds.

Illustrative non-limitative examples of gadolinium contrast agents are: extracellular fluid agents such as gadoterate (Dotarem®, Clariscan™, gadodiamide (Omniscan), gadobenate (MultiHance®), gadopentetate (Magnevist®), gadoteridol (ProHance®), gadoversetamide (OptiMARK™), gadobutrol (Gadovist® or Gadavist®), gadopentetic acid dimeglumine (Magnetol™); blood pool agents such as albumin-binding gadolinium complexes, for example gadofosveset (Ablavar®, formerly Vasovist®) and gadocoletic acid; or polymeric gadolinium complexes, such as gadomelitol (Vistarem®), gadomer 17 (GadoSpin™ D); and hepatobiliary (liver) agents, such as gadoxetic acid.

Illustrative non-limitative examples of radionuclides include gamma-emitting isotopes, for example, $^{99m}$Tc, $^{123}$I, and $^{m}$In, which can be used in radio scintigraphy using gamma cameras or single-photon emission computed tomography, as well as positron emitters, for example, $^{18}$F, $^{64}$Cu, $^{68}$Ga, $^{86}$Y, $^{124}$I, $^{213}$Bi and $^{211}$At, that can be used in PET or beta emitters, such as $^{131}$I, $^{90}$Y, $^{99m}$Tc, $^{177}$Lu, and $^{67}$Cu".

Illustrative non-limitative examples of PET contrast agents are radionuclide, isotopes with short half-lives, based on radioactive fluorine (F-18, for example fluorine-18 fluorodeoxyglucose, FDG), oxygen (oxygen-15), carbon (for example C-11), nitrogen (nitrogen-13), or gallium (gallium-68), zirconium (zirconium-89), or rubidium (rubidium-82).

The term "fluorophore", as used herein, refers to a fluorescent chemical compound that can re-emit light upon light excitation. Fluorescent dyes include, without limitation, Cy3, Cy2, Cy5 and FITC.

The nature of the binding of the protein of the invention to any of the molecules listed above can be covalent, based on electrostatic interactions or hydrophobic forces, or by adsorption. The skilled person in the art is able of binding the protein of the invention to a particular ligand using routine protocols and the selection of the more appropriate protocol will be based on the particular nature of the protein of the invention but also on the nature of the ligand to be bound. Furthermore, the binding can be performed between any of the amino acids forming the protein and the ligand, provided that at least two of $X_1$ to $X_6$ are free and are as defined above.

In another embodiment of the third aspect of the invention, the protein covalently binds to any of the elements listed above. Thus, the protein covalently binds via its N-terminal end and/or its C-terminal end to the element.

In another embodiment of the third aspect of the invention, optionally in combination with any of the embodiments provided above or below, the protein is bound to a cellular localization signal or a recognition domain.

In another embodiment of the third aspect of the invention, optionally in combination with any of the embodiments provided above or below, the cellular localization signal is a nuclear localization signal, an endoplasmic reticulum localization signal or a mitochondrial localization signal. In another embodiment of the third aspect of the invention, optionally in combination with any of the embodiments provided above or below, the cellular localization signal is SEQ ID NO: 71, SEQ ID NO: 72, SEQ ID NO: 73, SEQ ID NO: 74, SEQ ID NO: 75, SEQ ID NO: 76; SEQ ID NO: 77 or SEQ ID NO: 78.

Alternatively, in another embodiment of the third aspect of the invention, optionally in combination with any of the embodiments provided above or below, the recognition domain is a Hsp90 binding domain, a Hsp70 binding domain, a dss1 protein binding domain, a tag sequence, a TPR domain, an ankyrin domain, a Src homology 3 domain, a PDZ domain, a DNA binding protein (for example homeodomains, leucine zipper proteins, alpha repressor-like proteins) or a peptidoglycan recognition protein. In another embodiment of the third aspect of the invention, optionally in combination with any of the embodiments provided above or below, the recognition domain is selected from the group consisting of: SEQ ID NO: 82, SEQ ID NO: 83, SEQ ID NO: 84, SEQ ID NO: 85, SEQ ID NO: 86, SEQ ID NO: 87 and SEQ ID NO: 90.

In another embodiment of the third aspect of the invention, the protein is selected from the group consisting of SEQ ID NO: 79, SEQ ID NO: 91, SEQ ID NO: 93 and SEQ ID NO: 95.

In another embodiment of the third aspect of the invention, optionally in combination with any of the embodiments provided above or below, the protein comprises in the N-terminal end the sequence GAMGS (SEQ ID NO: 69). In another embodiment of the third aspect of the invention, the peptide in the N-terminal end is of sequence GAMGS (SEQ ID NO: 69). In another embodiment of the third aspect of the invention, optionally in combination with any of the embodiments provided above or below, the protein comprises in the C-terminal end a sequence with an alpha helix secondary motif. In another embodiment of the third aspect of the invention, optionally in combination with any of the embodiments provided above or below, the peptide in the C-terminal end comprises the sequence AEAKQNLGNAKQKQG (SEQ ID NO: 70). In another embodiment of the third aspect of the invention, optionally in combination with any of the embodiments provided above or below, the protein comprises in its N-terminal end the sequence GAMGS (SEQ ID NO: 69) and in its C-terminal end the sequence AEAKQNLGNAKQKQG (SEQ ID NO: 70).

The amino acid sequence according to the first aspect of the invention, the peptide of the second aspect of the invention and the protein of the third aspect of the invention can be prepared by routine methods such as solid synthesis phase, wherein successive steps of (a) deprotecting the amino acid to be bound, and (b) protected-amino acid coupling cycles are performed. The protecting group can be a N-protecting group, C-protecting group or a side-chain protecting group. There are commercially available protecting groups belonging to all three categories.

Alternatively, the amino acid sequence according to the first aspect of the invention, the peptide of the second aspect of the invention and the protein of the third aspect of the invention can be prepared by molecular cloning and expression in an appropriate host organism.

In addition to the above, the N(t) and/or C(t) of amino acid sequence of the first aspect of the invention, the peptide of the second aspect of the invention or the protein of the third aspect of the invention the end amino group and/or the end carboxy group can be derivatized. The end amino group can be derivatized by acylation, whereas the carboxy group can be derivatized by amidation. The skilled person in the art, using the general knowledge, is able of selecting the appropriate reagents and conditions to achieve such derivatizations.

In a fourth aspect the present invention provides a nucleic acid sequence coding for the amino acid sequence according to the first aspect of the invention or the peptide according to the second aspect of the invention or the protein according to the third aspect of the invention.

According to the present invention, the terms "nucleic acid" and "polynucleotide" are used interchangeably and refer to DNA, RNA or species containing one or more nucleotide analogues. Preferred nucleic acids or polynucleotides according to the present invention are DNA, most preferred double-stranded (ds) DNA.

In one embodiment of the fourth aspect of the invention, the nucleic acid sequence comprises a sequence selected from the group consisting of: SEQ ID NO: 28, SEQ ID NO: 30, SEQ ID NO: 32, SEQ ID NO: 34, SEQ ID NO: 36, SEQ ID NO: 44, SEQ ID NO: 46, SEQ ID NO: 48, SEQ ID NO: 50, SEQ ID NO: 52, SEQ ID NO: 54, SEQ ID NO:56, SEQ ID NO: 58, SEQ ID NO: 60, SEQ ID NO: 62, SEQ ID NO: 64, SEQ ID NO: 66, and SEQ ID NO: 68. In another embodiment of the fourth aspect of the invention, the nucleic acid sequence comprises a sequence selected from the group consisting of: SEQ ID NO: 98, SEQ ID NO: 100, SEQ ID NO: 102, SEQ ID NO: 104, SEQ ID NO: 106, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 148, SEQ ID NO: 156, SEQ ID NO: 158, and SEQ ID NO: 160. It is known by the skilled in the art that the genetic code is degenerated and therefore the nucleic acid sequence can differ from those listed herein. Therefore, the present invention also refers to those degenerated DNA sequences.

In a fifth aspect the present invention provides an expression cassette.

The term "expression cassette" is defined as a nucleic acid sequence composed of one or more genes coding for the desired amino acid peptide or protein, and the sequences controlling their expression such as promoter, open reading frame and terminator. Additional sequence elements such as secretion signals, marker genes or purification tags may also be comprised within the expression cassette.

In a sixth aspect the present invention provides a nucleic acid vector.

The term "vector" according to the present aspect of the invention is a nucleic acid suitable for the integration of foreign genetic elements (in particular, one or more genes of interest) into host cells and which are suited for replication and/or expression of the gene of interest. Appropriate vectors of the present invention are plasmids, viral vectors, cosmids, and artificial chromosomes. Of these, the most commonly used vectors are plasmids. In a preferred embodiment the vector is the pProEx-HTA vector (Invitrogen).

In a seventh aspect, the present invention provides a host cell.

The host cells may be prokaryotic or eukaryotic cells. Prokaryotic hosts according to the present invention include bacteria, in particular *E. coli* such as commercially available strains like C41, TOP10, DH5 α, HB101, BL21, etc., suitable for the propagation of the above vectors. Eukaryotic host cells can be yeast cells such as *Saccharomyces* or *Pichia* strains or mammalian cells such as CHO cells or insect cells such as Sf9 or plant cells.

The person skilled in the art is readily able to select appropriate vector construct/host cell pairs for appropriate propagation and/or transfer of the nucleic acid encoding the peptides or proteins of the present invention into a suitable host. Specific methods for introducing appropriate vector elements and vectors into appropriate host cells are equally known in the state of the art.

In an eighth aspect the present invention provides the use of the amino acid sequence according to the first aspect of the invention, the peptide according to the second aspect of the invention or the protein according to the third aspect of the invention as metal nanocluster scaffold. In a more particular embodiment, optionally in combination with any of the embodiments provided above or below, the metal atom or ion is selected from the group consisting of: copper, gold, silver, nickel, zinc, titanium, chromium, iron, cobalt, palladium, cadmium, ruthenium, rhodium, iridium, platinum and any combination thereof. In a yet more particular embodiment, optionally in combination with any of the embodiments provided above or below, the metal is copper, gold, silver or any combination thereof.

Peptides or proteins capable of forming alpha helix are particularly preferred as scaffold-forming nanoclusters. In a ninth aspect, the present invention provides a nanocluster.

Metal nanoclusters are defined as metal particles having a size equal to or less than 2 nanometers (nm). In a particular embodiment the metal nanoclusters of the present invention have a diameter of about 0.5-1.5 nm, more particularly the diameter is about 0.7-1.1 nm.

The size of the metal nanocluster can be measured by any method known by the expert, for example directly by mass spectrometry, transmission electron microscopy (TEM), high-resolution transmission electron microscopy (HR-TEM); or indirectly by its fluorescent emission properties.

In one embodiment of the ninth aspect, optionally in combination with any of the embodiments provided above or below, the metal atom or ion is a transition metal atom or ion. In a more particular embodiment, optionally in combination with any of the embodiments provided above or below, the metal atom or ion is selected from the group consisting of: copper, gold, silver, nickel, zinc, titanium, chromium, iron, cobalt, palladium, cadmium, ruthenium, rhodium, iridium, platinum and any combination thereof. In a yet more particular embodiment, optionally in combination with any of the embodiments provided above or below, the metal is copper, gold, silver or any combination thereof. In still another embodiment, optionally in combination with any of the embodiments provided above or below, the nanocluster comprises a mixture of gold and silver. In still another embodiment, optionally in combination with any of the embodiments provided above or below, wherein the gold:silver molar ratio is comprised from 5:1 to 15:1. In another embodiment, the gold:silver molar ratio is 9:1.

In another embodiment of the ninth aspect of the invention, optionally in combination with any of the embodiments provided above or below, the nanocluster: (a) is one wherein the metal is gold and comprises the peptide SEQ ID NO: 61; or, alternatively, (b) is one wherein the metal is silver and comprises the protein SEQ ID NO: 63; or, alternatively, (c) is one wherein the metal is copper and the protein SEQ ID NO: 59; or, alternatively, (d) is one wherein the metal is silver and the protein SEQ ID NO: 59; or, alternatively, (e) is one comprising a mixture of gold and silver and comprises the protein SEQ ID NO: 59; or, alternatively, (f) is one comprising a mixture of gold and silver at a molar ratio 9:1 and the protein SEQ ID NO: 59.

In another embodiment of the ninth aspect of the invention, optionally in combination with any of the embodiments provided above or below, the metal nanocluster is fluorescent.

The term "fluorescent metal nanocluster" means that the metal nanocluster of the present invention, after being excited at a given wavelength, emits light of a wavelength different from the excitation wavelength.

In some embodiments the fluorescent metal nanocluster fluoresces in a visible color upon excitation. In certain embodiments, the excitation light is ultraviolet light, visible light, or near infrared light. For example, the excitation light (provided, for example, by a laser) comprises a wavelength from 200 nm to 2000 nm. In another embodiment of the ninth aspect of the invention, optionally in combination with any of the embodiments provided above or below, the metal nanocluster is fluorescent with an emission wavelength maximum at 440-460 nm when excited at 360-380 nm. In another embodiment of the ninth aspect of the invention, optionally in combination with any of the embodiments provided above or below, the nanocluster is fluorescent with an emission wavelength maximum at 440-460 nm when excited at 360-380 nm and with an emission wavelength maximum at 580-640 nm when excited at 430-460 nm. The skilled person in the art, using the general knowledge, can achieve the different fluorescence colors, for example by using specific metal-reducing conditions.

The examples provided herein demonstrate the fluorescence of the metal NCs of the invention. Each graph refers to an independent experiment, the experimental data shown in each graph were simultaneously obtained and therefore they were comparable among them.

In another embodiment of the ninth aspect of the invention, optionally in combination with any of the embodiments provided above or below, the number of Cys residues of the protein of the third aspect of the invention is 16, 17, 18, 19 or 20. In a more particular embodiment, the number of Cys residues of the protein of the third aspect of the invention is 16, 17, 18, 19 or 20 and the metal is gold.

In another embodiment of the ninth aspect, optionally in combination with any of the embodiments provided above or below, the number of metal atoms in the NC is between 1 and 20, in a particular embodiment is between 3 and 8 atoms.

In another embodiment the metal NC of the ninth aspect, optionally in combination with any of the embodiments provided above or below, the metal is gold. In a more particular embodiment, the metal is gold and the number of metal atoms in the NC is 3, 4, 5, 6, 7 or 8.

In a tenth aspect the present invention refers to a combination of at least two metal nanoclusters of the ninth aspect of the invention. In a preferred embodiment the combination is of AuNCs and AgNCs; alternatively is of AuNCs and CuNCs; alternatively is of CuNCs and AgNCs; or alternatively is of AuNCs, AgNCs and CuNCs.

In an eleventh aspect, the invention refers to a process for the production of the metal nanocluster of the ninth aspect of the invention comprising the step of: a) mixing the protein of the third aspect of the invention with a metal containing compound, for the adsorption of the metal to the metal coordination residues present in the protein.

In an embodiment of the eleventh aspect the metal containing compound is a metallic salt. In a preferred embodiment the metallic salt is selected from the group consisting of: $HAuCl_4$, $AuCl$, $AuCl_3$, $KAuCl_4$, $AuI$, $AuBr_3$, $Au(OH)_3$, $HAuBr_4$, $AgNO_3$, $AgCl$, $Ag_2CO_3$, $Ag_2SO_4$, $AgClO_4$, $AgI$, $AgCN$, $AgNO_2$, $AgNO_3$, $AgF$, $AgPF_6$, $AgOCN$, $Ag_3PO_4$, $AgF_2$, $CuSO_4$, $CuI$, $CuCl$, $CuCl_2$, $CuBr$, $CuBr_2$, $CuCN$, $CuF$, $CuF_2$, $Cu(ClO_4)_2$, $Cu(NO_3)_2$, $Cu(CO_2CH_3)_2$, $Ni(OCOCH_3)_2$, $NiCl_2$, $NiSO_4$, $Ni(NO_3)_2$, $K_2Ni(CN)_4$, $Ni(ClO_4)_2$, $NiBr_2$, $NiI_2$, $Ni(OH)_2$, $NiCO_3$, $NiF_2$, $NiC_2O_4$, $ZnSO_4$, $ZnI$, $ZnCl$, $ZnCl_2$, $ZnBr$, $ZnBr_2$, $ZnCN$, $ZnF$, $ZnF_2$, $Zn(ClO_4)_2$, $Zn(NO_3)_2$, $Zn(CO_2CH_3)_2$, $ZnSO_4$, $(C_6H_5O_7)_2Zn_3$, $(CH_3CO_2)_2Zn$, $Ti[OCH(CH_3)_2]_4$, $Ti(OCH_2CH_2CH_2CH_3)_4$, $Ti[OCH_2CH(C_2H_5)(CH_2)_3CH_3]_4$, $CrCl_2$, $CrCl3$, $CrF2$, $CrF3$, $CrBr2$, $CrBr3$, $CrI2$, $CrI3$, $Cr(ClO_4)_3$, $K_3Cr(C_2O_4)_3$, $Cr_2(SO_4)_3$, $CrPO_4$, $FeCl_2$, $FeCl_3$, $Fe(NO3)_3$, $Fe(NO3)_2$, $Fe(ClO_4)_3$, $C_{12}H_{14}FeO_{12}$, $FeSO_4$, $C_6H_5FeO_7$, $Co(NO_3)_2$, $Co(SCN)_2$, $CoCl_2$, $CoF_2$, $CoF_3$, $CoI_2$, $CoBr_2$, $CoCO_3$, $Co_3(PO_4)_2$, $CoSO_4$, $Co(ClO_4)_2$, $Co(OH)_2$, $(CH_3CO_2)_2Co$, $(CF_3COO)_2Pd$, $C_{10}H_{18}O_4Pd$, $[(C_6H_5)_3P]_2PdCl_2$, $Cd(NO_3)_2$, $Cd(OCOCH_3)_2$, $C_{12}H_{20}CdN_2S_4$, $C_{12}H_{22}CdO_{14}$, $CdCl_2$, $CdSO_4$, $CdI_2$, $CdCO_3$, $Cd(ClO_4)_2$, $CdBr_2$, $Cd(OH)_2$, $RuCl_3$, $[Ru(NH_3)_6]Cl_2$, $[Ru(NH_3)_6]Cl_3$, $RuI_3$, $Ru(NO)Cl_3$, $[Ru(NH_3)_5Cl]Cl_2$, $H_{15}Cl_2N_5Ru$, $[(CF_3COO)_2Rh]_2$, $ClRh(P(C_6H_4SO_3.Na)_3)_3$, $Rh(NO_3)_3$, $IrCl_3$, $H_2Cl_6Ir$, $IrCl_4$, $Ir_4(CO)_{12}$, $IrBr_3$, $[Ir(NH_3)_5Cl]Cl_2$, $PtCl_2$, $PtCl_4$, $H_2PtCl_6$, $K_2PtCl_6$, $(NH_4)_2PtCl_6$, $Pd(NO_3)_2$, halides of Gd, Tb, Yb, Er, Cy, Nd, other lanthanides salts, and a combination thereof. In a preferred embodiment the metallic salt is $HAuCl_4$, $AgNO_3$ or $CuSO_4$ or any combination thereof.

In another embodiment of the eleventh aspect, optionally in combination with any of the embodiments provided above or below, the metal containing compound is the metallic salt $Cd(CH_3CO_2)_2$.

In another embodiment of the eleventh aspect the step a) is performed for at least 20 minutes, particularly for at least 30 minutes, more particularly from about 30 to 60 minutes.

In an embodiment of the eleventh aspect of the invention, in step a) the molar ratio between the metal and protein is from 2:1 to 120:1. In another embodiment, optionally in combination with any of the embodiments provided above or below, the molar ratio is from 5:1 to 70:1. In another embodiment, optionally in combination with any of the embodiments provided above or below, the molar ratio is 5:1, 20:1 or 50:1. In another embodiment, the molar ratio is 50:1.

In another embodiment of the eleventh aspect the process further comprises performing a reduction step b) which comprises adding a reducing agent.

The present inventors have found that due to the versatility of the protein of the invention, modulation of fluorescence NC properties can be achieved by adjusting the different parameters of the process. In connection with the above, it has been found that performing the process under a particular molar ratio between the reducing agent and the metal, it is achieved a NC with increase in fluorescence. In view of this, in a twelfth aspect of the present invention refers to the metal nanocluster obtainable by the product of the eleventh aspect of the invention.

In one embodiment of the eleventh aspect of the invention, optionally in combination with any of the embodiments provided above or below, step (b) is performed in an excess amount of reducing agent. In one embodiment, the molar ratio between reducing agent:metal is in the range from to 3:1 to 600:1. In a particular embodiment is in the range 5:1 to 500:1. In another embodiment, the molar ratio between reducing agent:metal is 10:1 to 200:1. In a more particular embodiment the molar ratio is 100:1.

The reduction agents used in the method of the present invention in order to achieve the metal NCs of the present invention can be any reducing agent known by the expert in the field. In a particular embodiment the reducing agent can be sodium ascorbate, tannic acid, hydrazine, sodium borohydride, sodium cyanoborohydride, dextrose, dimethylamine borane, 2,5 diaminobenzenesulfonic acid, 1,2-hexadecanediol, or a mixture thereof. In another embodiment, the reducing agent is sodium sulfide.

In another embodiment, step (b) is performed in a polar solvent, either protic or aprotic. In one embodiment, the solvent is water.

In another embodiment of the eleventh aspect of the invention, optionally in combination with any of the embodiments provided above or below, step (b) is performed at a pH range of 5.5-12.0. In a particular embodiment the pH is 7.0.

In another embodiment of the eleventh aspect of the invention, step (b) is performed at a temperature of about 30-55° C. In a particular embodiment, step (b) is performed at a temperature of about 37-55° C.; more particularly of about 50° C.

In another embodiment of the eleventh aspect of the invention, the step b) is performed for a period of time from about 20-90 hours, particularly from about 24-30, 48-50 or 70-75 hours; and more particularly, for about 72 hours.

In another embodiment of the eleventh aspect of the invention, the step b) is performed for a period of time from about 20-144 hours, particularly from about 96 to 120 hours, and more particularly, for about 120 hours.

In a preferred embodiment of the eleventh aspect of the invention, step a) is performed by mixing the metal and the protein at a molar ratio of about 5:1, 20:1 or 50:1; and step b) is performed at a temperature of about 30-55° C.; for a period of time of about 20-90 hours. In a more particular embodiment in step a) the molar ratio between the metal and protein is 50:1; and step b) is performed at a temperature of about 50° C., for a period of time of about 72 hours.

The protein-stabilized metallic nanocluster resulting from step (b) can be subjected to a separation technique to separate the nanocluster from other components of the solution (e.g., unreacted free metal cations, anions, salts or the proteins of the invention). Illustrative non-limitative examples of these techniques are filtration (e.g., using a membrane with a selected molecular cut-off), precipitation (e.g., using a water-soluble organic solvent such as ethanol) and fast protein liquid chromatography (FPLC) can be applied. The isolated nanoclusters can then be subsequently dried or lyophilized.

A thirteenth aspect of the present invention refers to the use of the metal nanocluster of the ninth aspect or twelfth aspect of the invention or the combination of metal nanoclusters of the tenth aspect of the as imaging agent, as drug-delivery carrier, as metabolic interfering agent, as catalyst, as an analyte, for phasing crystallographic data set, as cell labelling agent, as specific protein labeling agent, as biosensor, as a temperature sensor, as photosensitizer, or for the manufacture of an optoelectronic device.

In a particular embodiment of the thirteenth aspect, the use can be performed in cells of any origin. In a particular embodiment the cells are plant or animal cells. In a much more particular embodiment the cell is a human cell.

In an embodiment of the present invention, when the metal NC of the ninth aspect or the twelfth aspect is used, the detection of the fluorescence signal from the fluorescent metal nanocluster comprises detecting a change in the fluorescence signal detected in a sample as compared to a control sample. For example, the change in the fluorescence signal is a change in the wavelength of the fluorescence signal. In certain aspects, the change in the fluorescence signal is a change of at least 1, 2, 3, 4, 5, 6, 7, 8, 9, or 10 nm in the wavelength of the fluorescence signal.

In another preferred embodiment of the thirteenth aspect, the use is an in vitro or an in vivo use.

A particular use of the protein-stabilized metal nanocluster is the use for delivering a drug, preferably a therapeutically effective amount of a drug.

The term "therapeutically effective amount" or "effective amount" as used herein, means an amount of an active agent (drug) high enough to deliver the desired benefit, either the treatment or prevention of an illness, but low enough to avoid serious side effects within the scope of medical judgment. The particular dose of said drug according to this invention will be determined by the particular circumstances surrounding the case, including the compound administered, the route of administration and the particular condition being treated.

The term "drug" refers to a chemical substance used in the treatment, cure, or prevention of a disease or condition, e.g., cancer, etc. The chemical nature of the drug can vary broadly, e.g. it can be a small molecule, a peptide, and so on. In a particular embodiment the drug may be charged or neutral, fluorescent or not.

As sensors, the protein-stabilized metallic nanocluster can be used for example as temperature sensor, pH sensor and in colorimetric biosensing in diagnostics or for assessing the response to a treatment.

When the protein-stabilized metallic nanocluster is used for catalyzing a chemical reaction, the nanocluster can be located on a support. Combinations of catalyst metals may be used. Any suitable support particles may be used. Typical supports suitable for particles are carbon supports, but may also be made of silica or any other porous materials. Suitable carbon support materials include: Shaw C-55™ (Chevron Texaco Corp., Houston, Tex.), Vulcan® XC-72 carbon black (Cabot Corp., Waltham, Mass.), Black Pearls® 2000 Carbon (Cabot Corp., Waltham, Mass.), and the like.

The protein-stabilized metallic nanocluster can be used for phasing crystallographic data set similarly as multiwavelength anomalous diffraction (MAD) or Single-wavelength Anomalous Dispersion (SAD) phasing using heavy atoms.

The protein-stabilized metallic nanocluster can be used as photosensitizer for photodynamic therapy.

A photosensitizer is a molecule that produces a chemical change in another molecule in a photochemical process. Photodynamic therapy (PDT) is a form of phototherapy involving light and a photosensitizing substance, used in conjunction with molecular oxygen to elicit cell death. PDT can be used to provoke the death of mammalian cells, including human cells, for example cancer cells (it can be used for example in prostate, skin, head and neck, lung and bladder cancer), and has been used in the treatment of wet age-related macular degeneration, psoriasis and atherosclerosis. PDT can be used to treat conditions caused by bacteria, fungi and virus. PDT is useful in treating acne, and in anti-viral treatments, including herpes. Therefore, the protein-stabilized metallic nanocluster can be used in any of the above mentioned treatments as photosensitizer for photodynamic therapy.

The protein-stabilized metallic nanocluster can be used as an optoelectronic device. An optoelectronic device is an electronic device that operates on both light and electrical currents. This can include electrically driven light sources such as laser diodes and light-emitting diodes, components for converting light to an electrical current such as solar and photovoltaic cells and devices that can electronically control the propagation of light.

In particular embodiment of the fourteenth aspect of the invention the kit comprises one or more vials.

In another embodiment of the fourteenth aspect of the invention the kit comprises the metal containing compound above mentioned. In a more preferred embodiment the kit comprises the reduction agent above mentioned.

In another embodiment of the fourteenth aspect the kit comprises instructions (such as a leaflet) with the indication for use the amino acid sequence according to the first aspect of the invention or the peptide according to the second aspect of the invention or the protein according to the third aspect of the invention or the nucleic acid sequence according to fourth aspect of the invention or the expression cassette according to the fifth aspect of the invention or the nucleic acid vector of the sixth aspect of the invention or the host cell according to the seventh aspect of the invention for the production of the metal nanocluster of the ninth or twelfth aspect of the invention or the combination of metal nanoclusters according to the tenth aspect of the invention.

In another embodiment of the fourteenth aspect of the invention the kit comprises instructions (such as a leaflet) with the indication for use the metal nanocluster of the ninth or twelfth aspect of the invention or the combination of metal nanoclusters according to the tenth aspect of the invention in the uses of the thirteenth aspect of the invention.

In another embodiment of the fourteenth aspect of the invention the kit comprises elements that allow the use of the protein-stabilized metallic nanocluster of the invention in the above mentioned uses.

In a sixteenth aspect, the present invention provides a device.

The protein scaffold can be placed on a substrate. The organization of the scaffold in the substrate can determine the particular device being made. It can be placed in a predetermined pattern, such as an array. Arrays can be formed by plural, monodispersed (clusters of substantially the same size) protein-stabilized metal nanoclusters. The substrate can be treated to attach the protein stabilized-nanoclusters to the scaffold or to attach the proteins that will act as scaffold.

There are several methods for placing the scaffold onto substrates in predetermined patterns. For example, a first method comprises aligning scaffold molecules in an electrical field created between electrodes on the substrate. It therefore will be appreciated that the scaffold molecules used must have sufficient dipoles to allow them to align between the electrodes. This is one reason why polypeptides that form alpha helix are preferred. The alpha helix imparts a sufficient dipole to the polypeptide molecules to allow alignment of the molecules between the electrodes upon formation of an electrical field. A second method comprises polymerizing monomers, oligomers (10 amino acids or nucleotides or less) or small polynucleotides or polypeptides into longer molecules on the surface of a substrate. For example, scaffold molecules can be polymerized as a bridge between electrodes on a substrate.

The scaffold simply may be placed on the surface of the substrate, in contrast to more tightly adhering the protein to the substrate such as through electrostatic or covalent bonds. As used herein, the term "substrate" refers to any material, or combination of materials, that might be used to form devices, for example electronic devices. For example, the substrate might be selected from the group consisting of silicon, silicon nitride, ultra-flat glass, metals, and combinations thereof.

Simply placing the scaffold on the surface simplifies the process for making working devices. Placing the scaffold on the surface of the substrate can be accomplished by (1) forming solutions containing the molecular scaffold, (2) placing the solution containing the scaffold onto a substrate, such as by spin coating the solution onto a substrate, and (3) allowing the solvent to evaporate, thereby depositing the solid molecular scaffold onto the substrate surface. If simple deposition of the scaffold onto the substrate does not produce a sufficiently robust device, then the scaffold might be more tightly coupled to the substrate. One method for accomplishing this is to use compounds that act as adhesives or tethers between the substrate and the molecular scaffold. Which compounds to use as adhesives or tethers depends on the nature of the substrate and the metal nanocluster. For example, amino-silane reagents may be used to attach molecular scaffolds to the substrate. The silane functional group allows the tether to be coupled to a silicon, glass or gold substrate. This provides a tether having a terminal amino group that can be used to react with the scaffold to tether the scaffold to the substrate. The terminal amino group also can be used as an initiation site for the in situ polymerization of the protein using activated amino acids.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

EXAMPLES

Materials and Methods:
1. Preparation of Peptide Blocks:

For the design of the proteins of formula (II) provided in this section, the peptide block named as "CTRP1_W", "unit W", "W", "module W" or "W module" of sequence SEQ ID NO: 37 and encoded by the DNA sequence SEQ ID NO: 38 was used as the starter block. From this, punctual mutations were made in SEQ ID NO: 38 using QuickChange Site-Directed mutagenesis kit (Stratagene), following manufacturer's instructions. Table 1 summarizes each of the variants made:

TABLE 1 modules used in the invention:

| Module | Mutations | Protein SEQ ID NO: | DNA SEQ ID NO: |
| --- | --- | --- | --- |
| H | Y5H_N9H | 27 | 28 |
| C | Y5C_N9C | 29 | 30 |
| C1 | E2C_N6C | 31 | 32 |
| C2 | E2C_N6C_N9C | 33 | 34 |
| C3 | E2C_N6C_N9C_Y12L_K13C | 35 | 36 |
| X | E2C_N6H | 97 | 98 |
| X1 | E2C_N9H | 99 | 100 |
| H1 | E2H_Y5H_N6H_N9H | 119 | 120 |
| H2 | E2H_Y5H_N9H_Y12L_K13H | 121 | 122 |
| H3 | E2H_Y5H_N9H | 147 | 148 |
| R | Q14C_D31C | 149 | 150 |
| R1 | Q14C_E29C_D31C | 151 | 152 |
| R2 | Q14C_D18C_E29C_D31C | 153 | 154 |

For the preparation of these modules, SEQ ID NO: 23 was used as the "G" element described in formula (I). The modules were also performed using SEQ ID NO: 25 instead with similar results (data not shown). In an analogous way, SEQ ID NO: 24 is used as well.

2. Preparation of Proteins of Formula (II):

The nucleic acid coding the modules described in the previous section were ligated together (using BamHI and BgIII in the pProEx-HTA vector (Invitrogen)) in order to obtain the proteins listed below in table 2. Construct identities were verified by DNA sequencing (Stab vida). The synthetic genes for the desired protein in said vector, coding for N-terminal (His)6 tag and ampicillin resistance, were transformed into *E. Coli* C41 cells and cultured overnight at 37° C. on agar plates. One single colony was selected and incubated overnight in 50 mL of Luria-Bertani (LB) media containing 100 μg mL$^{-1}$ of ampicillin. 10 mL of overnight cultures were then dispensed into 1 L of LB media supplemented with 100 μg mL$^{-1}$ ampicillin. The cells were grown in an incubator-shaker (250 rpm) at 37° C. until the optical density (OD600) reached 0.6-0.8. Expression of CTPRs was induced with 1 mM isopropyl β-d-thiogalactoside (IPTG) followed by 5 h expression at 37° C. The cells were harvested by centrifugation at 5000 rpm for 20 min. The cell pellets were resuspended in lysis buffer consisting of 50 mM Tris, 300 mM sodium chloride. After 2 min sonication at 30% power using a microtip sonicator, lysed cells were centrifuged at 16 000 rpm for 30 min and the protein supernatant was purified using standard Co-NTA affinity purification protocol. The N-terminal hexahistidine tag was then cleaved from the CTPR proteins using TEV protease. As a final step, the aqueous solutions of CTPRs were dialyzed against 10 mM phosphate buffer three times at 4° C. using a dialysis membrane with molecular weight cut-off of 6-8 kDa. Protein concentration was measured by UV absorbance at 280 nm, using extinction coefficients at 280 nm calculated from amino acid composition.

In this way, the proteins of formula (II) listed in Table 2 were prepared:

TABLE 2

Proteins of formula (II)

| Proteins | Protein SEQ ID NO: | DNA SEQ ID NO: | MW(Da) |
|---|---|---|---|
| WWW | 39 | 40 | 14079.2 |
| HWW | 41 | 42 | 14076.2 |
| WHW | 43 | 44 | 14076.2 |
| WHHW | 45 | 46 | 18103.5 |
| WHHHW | 47 | 48 | 22130.9 |
| WCC1W | 49 | 50 | 18001.5 |
| WC1C1W | 51 | 52 | 18035.6 |
| WC1C1C1W | 57 | 58 | 22029.0 |
| WC2C2W | 53 | 54 | 18013.7 |
| WC2C2C2W | 59 | 60 | 21996.2 |
| WC3C3W | 55 | 56 | 17863.6 |
| WC3C3C3W | 61 | 62 | 21771.0 |
| WC3C3C3C3W | 63 | 64 | 25678.4 |
| WC3C3C3C3C3W | 65 | 66 | 29585.7 |
| WC3C3C3C3C3C3W | 67 | 68 | 33493.1 |
| WXW | 101 | 102 | 14053.2 |
| WX1W | 103 | 104 | 14053.2 |
| WC1W | 105 | 106 | 14042.3 |
| WWW_Cys | 107 | 108 | 14182.3 |
| WH1W | 123 | 124 | 14107.3 |
| WH1H1W | 125 | 126 | 18165.7 |
| WH1H1H1W | 127 | 128 | 22224.1 |
| WH1H1H1H1W | 129 | 130 | 26282.5 |
| WH1H1H1H1H1W | 131 | 132 | 30340.9 |
| WH2W | 133 | 134 | 14043.2 |
| WH2H2W | 135 | 136 | 18037.5 |
| WH2H2H2W | 137 | 138 | 22031.8 |
| WH2H2H2H2W | 139 | 140 | 26026.1 |
| WH2H2H2H2H2W | 141 | 142 | 30020.4 |
| WWWWWW | 143 | 144 | 26170.2 |
| WC2W | 155 | 156 | 14031.3 |
| WC3W | 157 | 158 | 13956.2 |
| WH3W | 159 | 160 | 14084.2 |
| WRW | 161 | 162 | 14042.3 |
| WR1W | 163 | 164 | 14016.3 |
| WR2W | 165 | 166 | 14004.3 |

Wherein peptides C, C1, C2, C3, H, H1, H2, H3, R, R1, R2, X and X1, are as defined in the previous section.

The synthesized CTPR proteins further comprised an extra sequence, GAMGS, (SEQ ID NO: 69) in the N-terminal end, due to the cloning technique and an extra sequence (AEAKQNLGNAKQKQG, SEQ ID NO: 70) in the C-terminal end, which had alpha helix secondary structure which was useful for increasing the solubility of the protein.

Before their use the proteins were purified three times, two by affinity chromatography and another one by Fast Protein Liquid Chromatography (FPLC) as follows:
1. Cobalt or nickel nitrilotriacetic acid (NTA) affinity purification protocol: the protein supernatant obtained after cell lysis by sonication was loaded into the affinity column (Co-NTA, Ni-NTA) using a pump at a flow rate of 5 ml/min. Then, the column was washed with 50-100 mL of 300 mM NaCl, 5 mM imidazole, Tris/HCl 50 mM pH 8.0. Finally, the protein was eluted using 25 mL of 300 mM NaCl, 300 mM imidazole, Tris/HCl 50 mM pH 8.0.
2. The N-terminal hexahistidine tag was then cleaved from the proteins using Tobacco Etch Virus (TEV) protease cleavage. The protein was incubated overnight with TEV protease at 1 unit/ml at 4° C. in digestion buffer (0.5 mM EDTA, 1 mM DTT, 10% glycerol, 50 mM Tris pH 8.0).
3. Co-NTA or Ni-NTA affinity purification protocol: the protein solution obtained after the N-terminal hexahistidine tag cleavage, was loaded into the affinity (Co-NTA, Ni-NTA) using a pump at a flow rate of 5 ml/min. The purified protein was collected in the flow-through fraction.
4. FPLC using high-resolution preparative size exclusion chromatography: the purified protein obtained after two affinity chromatographs was loaded in a FPLC system equipped with a gel filtration column (Superdex 75 or 200 depending on the size of the protein) using a syringe. The protein was eluted using a solution of 300 mM NaCl, Tris/HCl 50 mM pH 7.4 at a flow rate of 1 ml/min. The protein was collected in fractions of 2 mL.
5. The protein concentration was measured by UV absorbance at 280 nm, using extinction coefficients at 280 nm calculated from amino acid composition. The protein samples were stored frozen at −20° C.

3. Synthesis of Protein-Stabilized Nanoclusters:

a) Synthesis of Protein-Stabilized Copper Nanoclusters (Protein-CuNCs)

2000 µL of the protein to be tested at 10 µM were mixed with $CuSO_4$ (50 eq. respect to protein or 5 eq. respect to number of cysteines) first vortexing for 30 seconds and then leave for at least 30 minutes to allow the adsorption of copper ions to the protein. Then, the reduction of the copper ions to metallic copper was achieved by adding sodium ascorbate at 100 mM (10 or 100 eq. respect to CuSO4). The reaction mixture was vortexed for 30 seconds and then was incubated at 37° C. or 50° C. for 72 h. Finally, the samples were washed several times with PBS using Amicon ultrafiltration tubes with a 10-kDa membrane to eliminate unreacted salts and then purified by FPLC. The fluorescence spectra of protein stabilized copper nanoclusters were collected using a Fluorimeter Perkin Elmer.

b) Synthesis of Protein-Stabilized Gold Nanoclusters (Protein-Au NCs)

1000 µL of protein at 20 µM were mixed with $HAuCl_4$ (50 eq. respect to protein or 5 eq. respect to number of cysteines) first vortexing for 30 seconds and then leave for 30 minutes to allow the adsorption of gold ions to the cysteines of the protein. Then, the reduction of the gold ions to metallic gold was achieved by adding sodium ascorbate (10 or 100 eq. respect to $HAuCl_4$). The reaction mixture was vortexed for 30 seconds and then was incubated at 37° C. or 50° C. for 72 h. Finally, the samples were washed several times with PBS using Amicon ultrafiltration tubes with a 10-kDa membrane to eliminate unreacted salts and then purified by FPLC. The fluorescence spectra of protein stabilized gold nanoclusters were collected using a Fluorimeter Perkin Elmer.

c) Synthesis of Protein-Stabilized Silver Nanoclusters (Protein-Ag NCs)

500 µL of protein at 20 µM were mixed with $AgNO_3$ (50 eq. respect to protein or 5 eq. respect to number of cysteines) first vortexing for 30 seconds and then leave for 30 minutes to allow the adsorption of silver ions to the cysteines of the protein. Then, the reduction of the silver ions to metallic silver was achieved by adding sodium ascorbate (10 or 100 eq. respect to $AgNO_3$). The reaction mixture was vortexed for 30 seconds and then was incubated at 37° C. or 50° C. for 72 h. Finally, the samples were washed several times with PBS using Amicon ultrafiltration tubes with a 10-kDa membrane to eliminate unreacted salts and then purified by FPLC. The fluorescence spectra of protein stabilized silver nanoclusters were collected using a Fluorimeter Perkin Elmer.

4. Synthesis of Fluorescent Metal NCs with Metal Mixture:

The effect of the metal mixture in the synthesis and stabilization of metal (Au and Ag) NCs was evaluated using the same experimental conditions (reducing agent, ratio cysteine:metal:reducing agent and reaction time) as above under example 3 but in this case the 500 µL of the protein (WC2C2C2W) to be tested at 20 µM were mixed with $HAuCl_4$ and/or $AgNO_3$ (5 eq. respect to number of cysteines).

5. Synthesis of Protein-Stabilized Copper Nanoclusters with Different Emission Colors:

In addition, the possibility of generating Cu NCs with different emission colors was tested. To this aim, the synthesis and stabilization Cu NCs using the protein WHW as template was carried out following a protocol similar to the one described before for the synthesis and stabilization of Cu NCs, but changing different parameters as temperature (37 and 50° C.) and the reducing agent (sodium ascorbate, tannic acid and hydrazine).

In all cases 2000 µL of protein at 10 µM were mixed with CuSO4 (50 eq. respect to protein) for at least 30 minutes to allow the adsorption of copper ions to the protein's stabilizing sites. Then, the reduction of the copper ions to metallic copper was achieved by applying the following conditions (Table 3):

TABLE 3

|  | UV-emitting CuNCs | Blue-emitting CuNCs | Green-emitting CuNCs | Yellow-emitting CuNCs | Red-emitting CuNCs |
|---|---|---|---|---|---|
| Reduction agent | sodium ascorbate | sodium ascorbate | tannic acid | tannic acid | hydrazine |
| Volume and concentration of the reduction agent | 10 µL at 100 mM (10 eq.) | 100 µL at 100 mM (100 eq.) | 10 µL at 100 mM (10 eq.) | 100 µL at 100 mM (100 eq.) | 100 µL at 100 mM (100 eq.) |
| Reaction temperature | 37° C. | 37° C. | 37° C. | 50° C. | 50° C. |
| Reaction time | 24 h | 72 h | 72 h | 72 h | 72 h |

(The equivalents of the reduction agent was in respect to $CuCO_4$)

In all cases finally, the samples were washed several times with PBS using Amicon ultrafiltration tubes with a 10-kDa membrane to eliminate unreacted salts and kept at 4° C. for further experiments.

6. Protein of the Invention Fused to Nuclear Localization Signal NLS-WHW-CuNCs:

The ability of the protein-stabilized metal NCs of the present invention as cellular marker, an in particular as nuclear marker was tested.

Synthesis of NLS-WHW: The SV40 large T antigen nuclear localization signal (NLS) was used (SEQ ID NO: 71). Genes encoding the NLS-WHW proteins were constructed by polymerase chain reaction (PCR) with the pProEx-HTA vector which included the gene encoding the WHW protein and the primers that included the sequence of the NLS peptide (forward primer, SEQ ID NO: 88; reverse primer SEQ ID NO: 89). Construct identity was verified by DNA sequencing (Stab villa). SEQ ID NO: 79 refers to the NLS-WHW protein and the SEQ ID NO: 80 refers to the DNA encoding for said protein.

Synthesis of NLS-WHW-CuNCs: The synthesis and stabilization of Cu NCs with the NLS-WHW protein as template was carried out following the same protocol described before for the synthesis and stabilization of Cu NCs.

Finally, to investigate the effect of the presence of the NLS on the fluorescent properties of the CTPR protein stabilized CuNC, the fluorescence spectra of protein stabilized CuNCs were collected using a microplate reader.

Cell imaging: To assess cell imaging, MCF7 cells (purchased from American Type Culture Collection (Manassas, Va., USA)) were cultured on a 24-well plate at a density of $2.5×10^4$ cells per well in 500 µl of complete medium. After 24 h, the growth medium was removed and cells were then incubated 24 h at 37° C. in the presence of WHW-CuNCs and NLS-WHW-CuNCs (5 µM), After incubation, cells were washed three times with PBS to remove free unbound protein stabilized CuNCs and finally were observed under a fluorescence microscope.

7. Proteins of the Invention Fused to Recognition Domains (CC1CTPR390, CC1TPR2A and CC1TPR2A_T332R_D334K):

New CTPR proteins were created that combined the Cys clamp modules to produce fluorescent AuNCs and CTPR modules with different binding activity, wherein the structural and functional integrity of the CTPR proteins was preserved. A CC1 module (obtained by fusing modules C and C1 as indicated in table 1) was fused to three different Hsp90 recognition domains: CTPR390, TPR2A and TPR2A_T332R_D334K (by digestion with BamHI and BglII using the vector pProEx-HTA) generating SEQ ID NO: 91 which refers to the protein CC1-CTPR390 (codified by SEQ ID NO: 92), SEQ ID NO: 93 which refers to the protein CC1-TPR2A (codified by SEQ ID NO: 94) and SEQ ID NO: 95 which refers to the protein CC1-TPR2A_T332R_D334K (codified by SEQ ID NO: 96). The expression and purification of the proteins was performed as indicated before. The structure of protein was characterized as disclosed in example 6 above.

In addition, the ligand binding activity of the tested proteins was studied by using CC1-CTPR390, CC1-TPR2A, CC1-TPR2A_T332R_D334K proteins and its target peptide. The protein binding affinity to Hsp90 peptide (SEQ ID NO: 90) was determined by fluorescence anisotropy titrating with increasing amounts of protein into a 50 nM fluorescein-labeled Hsp90 peptide solution. Fluorescence intensities were recorded in a Perkin Elmer Fluorimeter equipped with excitation and emission polarizers. Excitation was accomplished with a 5 nm slit width at 492 nm and the emission recorded at 516 nm with slit width of 5 nm. Spectra were acquired in the region that reports the protein secondary structure elements, in particular the α-helical structure of the TPR proteins.

CC1-CTPR390-AuNCs were created using the same protocol as described previously (example 3b). The sensing properties of CC1-CTPR390-AuNCs were studied monitoring the AuNCs fluorescence. The fluorescence emission spectrum of a 20 μM protein concentration in PBS of a CC1-CTPR390-AuNCs solution was recorded. The change on the fluorescence emission spectra was determined upon titration with Hsp90 ligand peptide (from 5 to 600 μM). Fluorescence spectra were recorded in a spectrofluorometer (Perkin Elmer). Excitation was accomplished with a 5 nm slit-width at 370 nm and the emission recorded from 390 to 550 nm with slit widths of 5 nm. The fluorescence intensity was recorded at the maximum of emission (450 nm) and the average of three measurements for each point was reported.

8. Fluorescence Quantum Yield Determination:

The fluorescence quantum yield (ϕ) was calculated using anthracene in ethanol as reference (ϕRef=0.27, λexc=370 nm and λem=423 nm).

Fluorescence measurements were done using a Fluoromax 4 (Horiba Jobin-Yvon) and absorbance was recorded with a Cary 50 Conc (Varian) in quartz cuvettes.

9. Protein-NCs Structure Determination:

The protein secondary structure upon the generation of the nanoclusters was examined by circular dichroism (CD) using a Jasco J-815 spectrometer. CD spectra were acquired at 10 μM protein concentration in a 0.1 cm pathlength cuvette using a band-width of 1 nm at 1 nm increments and 10 second average time.

10. Transmission Electron Microscopy (TEM):

All the Cu/Rh grids coated with carbon were exposed to a glow discharge before sample deposition. The samples for TEM were prepared by depositing 10 μL of the test sample solution on the grid. After 3 min, the excess solution was removed from the grid using filter paper. To remove the deposited salt, the grid was washed with a drop of water and the excess water was dried using filter paper. Then a droplet of a 2% uranyl acetate solution was used to stain the grid for 1 min and the excess solution was removed using filter paper. Micrographs were recorded using Kodak SO-163 film, in a JEOL JEM1200EXII electron microscope with a tungsten filament operated at 100 kV and at 60 K magnifications.

11. Tests for Determining Possible Critical Parameters in the Stabilization of the NCs of the Invention Effect of ratio protein:metal, ratio metal:reducing agent and reaction time was investigated.

Using the protein WHW as template a similar protocol to the one provided above (example 3a) was developed to investigate the effect of protein:metal, ratio metal:reducing agent and reaction time in the synthesis and stabilization of Cu NCs. Three different ratios metal:protein (5:1, 20:1 and 50:1), two different ratios metal:reducing agent (1:10 and 1:100) and three different reaction times (24, 48 and 72 h) were tested. The ratio means molar equivalents. Results are provided in results section number 1 (named "Fluorescent metal nanoclusters comprising CTPR variant with coordinating residues based on Histidine clamps").

Figure 7A:
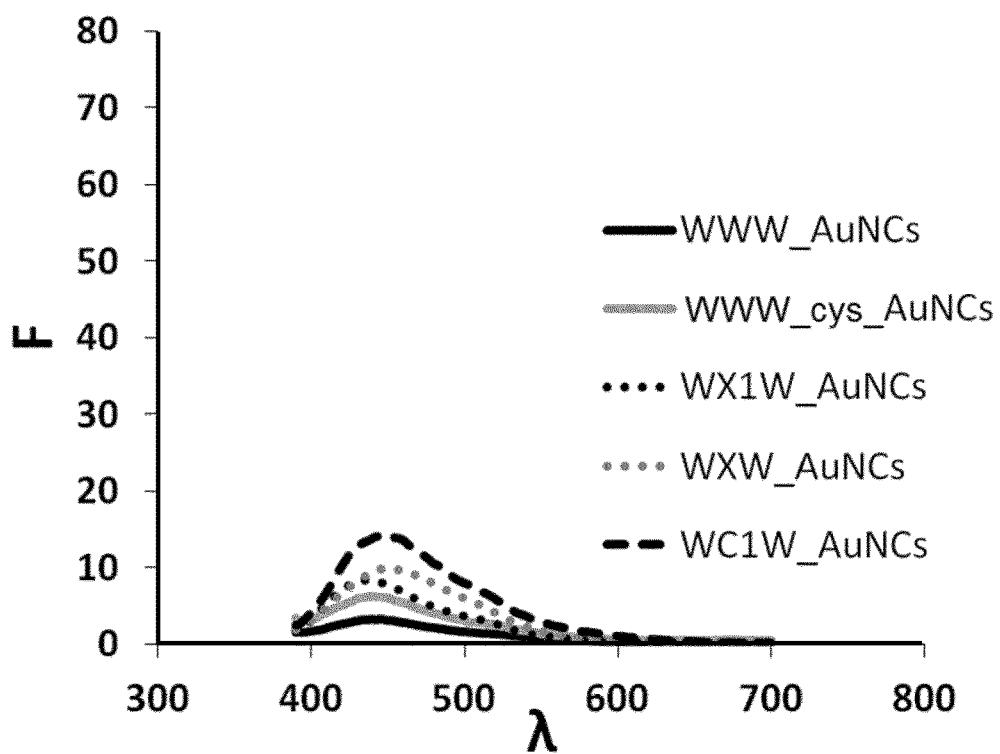
FIG. 7 represents the fluorescence emission spectra of different protein stabilized AuNCs, 7A, discloses the AuNCs formed by WWW, WWW_cys, WX1W, WXW and WC1W proteins; and 7B discloses the AuNCs formed by WHW, WC1C1W, WC2C2C2W, WC3C3C3W and WC3C3C3C3W proteins, (F: Fluorescent intensity (arbitrary units); λ: wavelength (nm)).
Figure 7B:
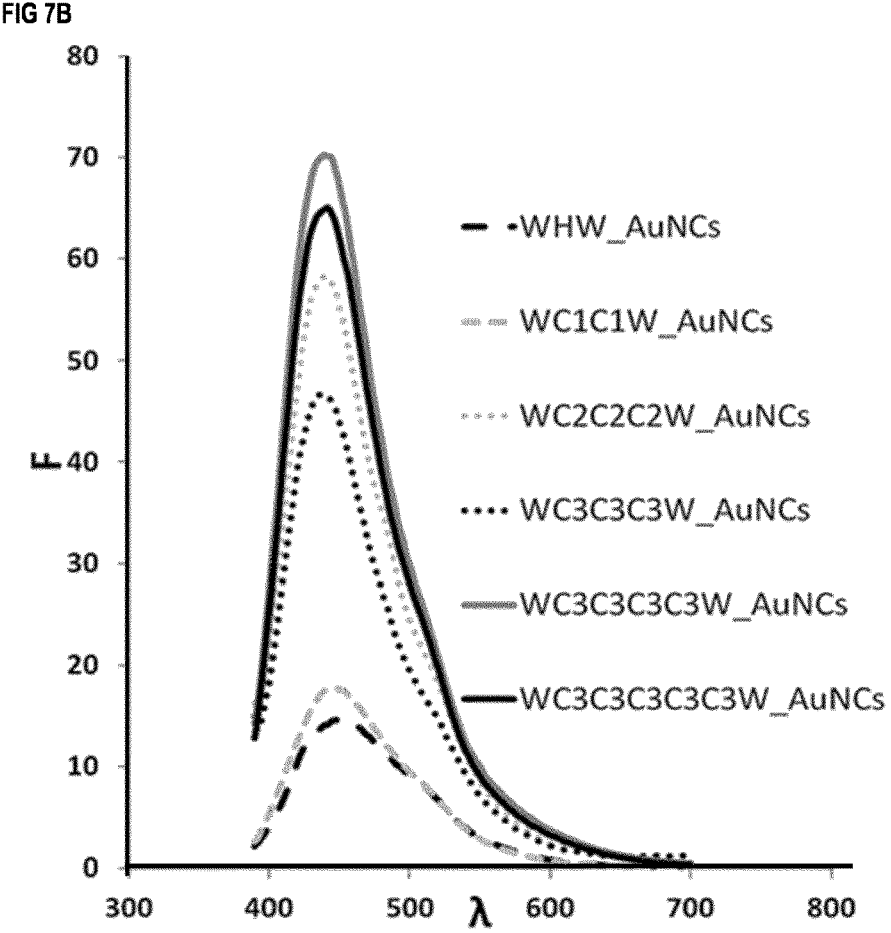

Using the proteins described in example 2 (WWW, WX1W, WXW, WC1W, WHW, WC1C1W, WC2C2C2W, WC3C3C3W, WC3C3C3C3W and WC3C3C3C3C3W) (FIGS. 7, 8 and 9) the following protocol was followed: 500 μL of protein at 20 μM were mixed with $CuSO_4$, $HAuCl_4$ or $AgNO_3$ (5 eq. respect to number of cysteines) first vortexing for 30 seconds and then leave for 30 minutes to allow the adsorption of metal ions to the cysteines of the protein. Then, the reduction of the copper/gold/silver ions to metallic copper/gold/silver was achieved by adding sodium ascorbate (10 eq. respect to $HAuCl_4$, $AgNO_3$ or $CuSO_4$). The reaction mixture was incubated at 37° C. or 50° C. for 72 h. The results are provided in the results section number 2 (named "Fluorescent metal nanoclusters comprising CTPR variant with coordinating residues based on Cysteine clamps").

Using the proteins described in example 2 (WC3C3C3C3W, WH1H1H1H1 and WH2H2H2H2W) (FIG. 10) the following protocol was used: 500 μL of protein solution at 20 μM were mixed with HAuCl4 (15 eq. respect to number of cysteines or histidines) and vortexed for 30 seconds. Then the reaction was incubated for 30 minutes to allow the adsorption of metal ions to the cysteines or histidines of the protein. Then, the reduction of the gold ions to metallic gold was achieved by adding sodium ascorbate (10 eq. respect to HAuCl4). The reaction mixture was incubated at 37° C. for 72 h. The results are provided in the results section number 4 (named "Fluorescent gold nanoclusters comprising CTPR variants containing several modules with coordinating residues based on Histidine clamps in comparison with Cysteine clamp").

Figure 11A:
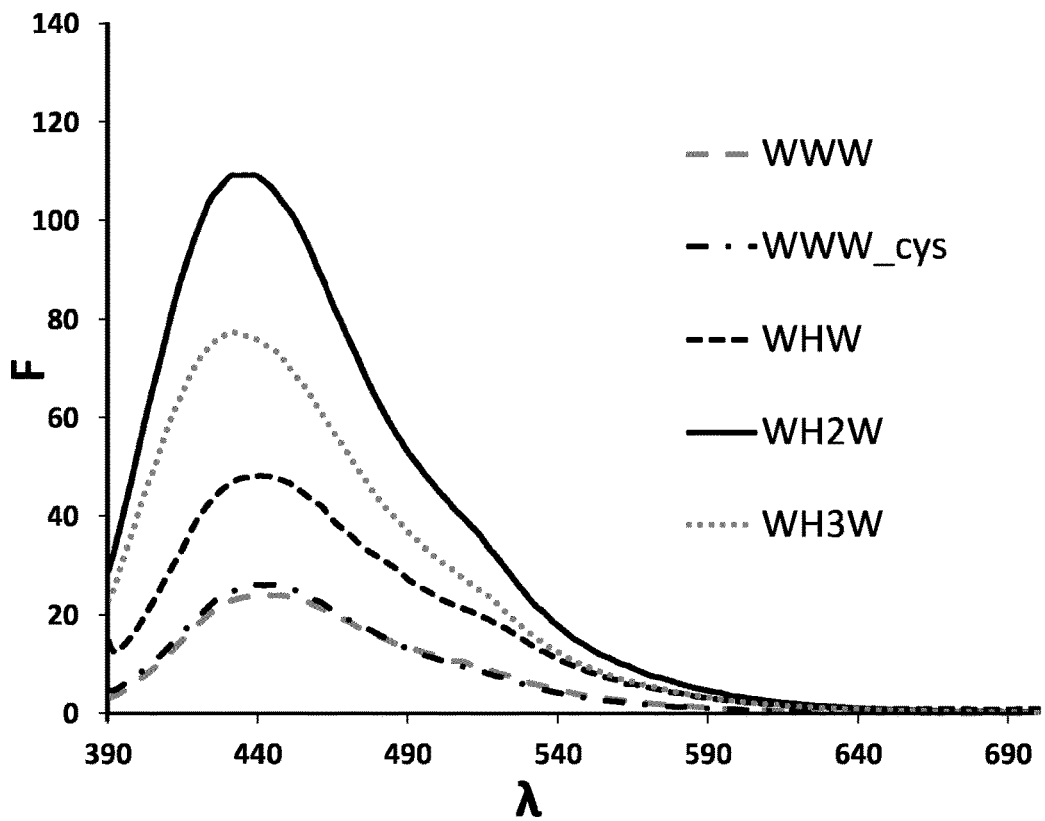
FIG. 11 represents the fluorescence emission spectra of different protein stabilized AuNCs, 11A, discloses the AuNCs formed by WWW, WWW_cys, WHW, WH2W and WH3W proteins; and 11B discloses the AuNCs formed by WC1W, WC2W, WC3W, WRW, WR1W and WR2W proteins. (F: Fluorescent intensity (arbitrary units); λ: wavelength (nm)).
Figure 11B:
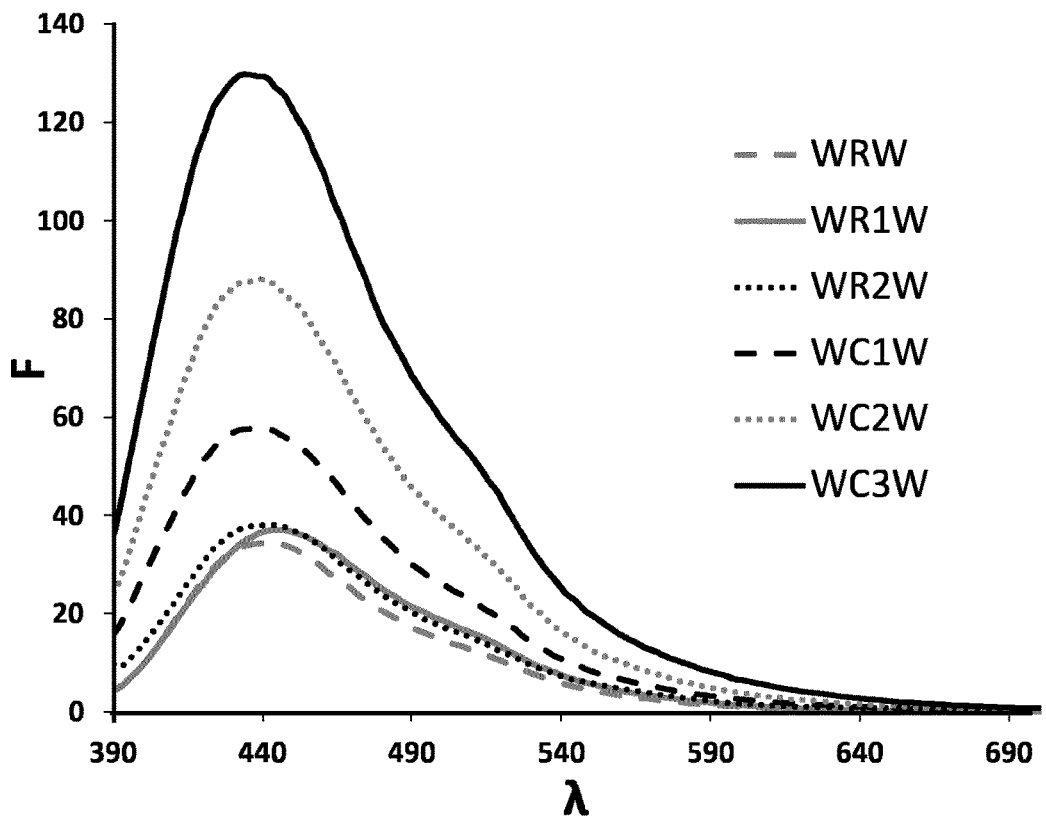
Figure 12A:
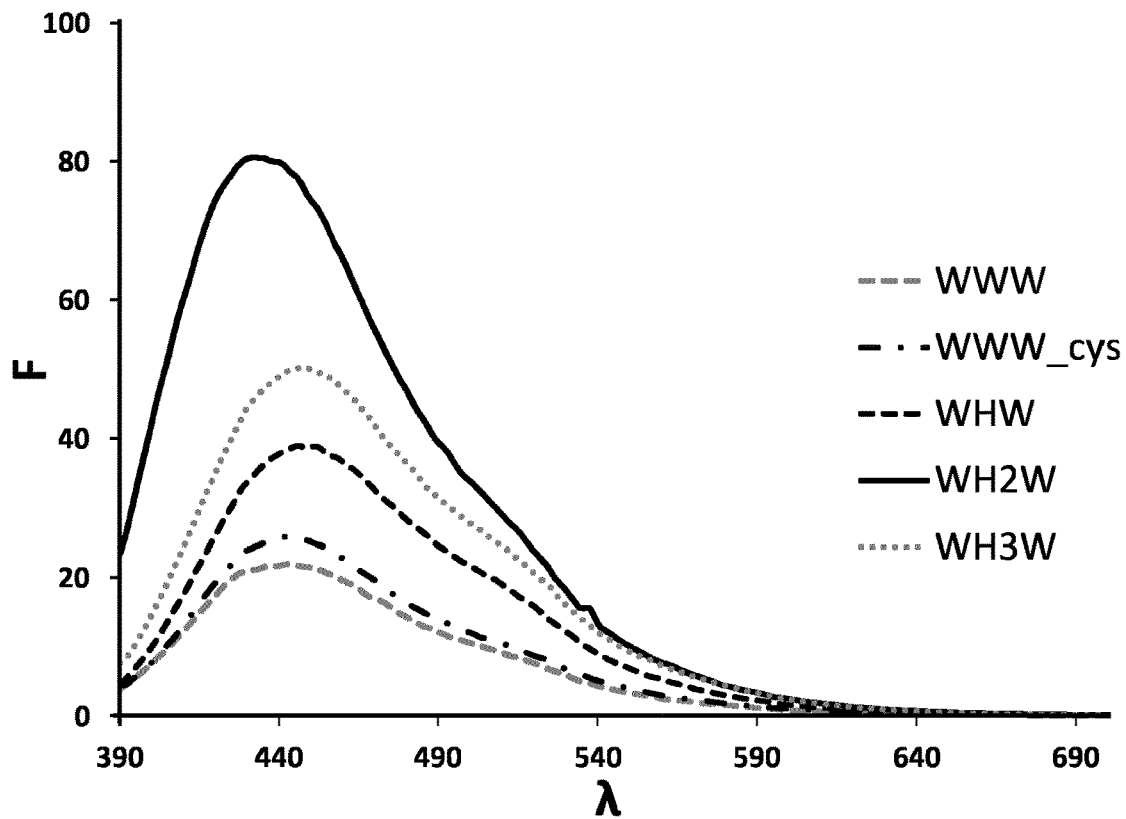
FIG. 12 shows the fluorescence emission spectra of different protein stabilized AgNCs. 12A, discloses the AgNCs formed by WWW, WWW_cys, WHW, WH2W and WH3W proteins; and 12B discloses the AgNCs formed by WC1W, WC2W, WC3W, WRW, WR1W and WR2W proteins. (F: Fluorescent intensity (arbitrary units); λ: wavelength (nm)).
Figure 12B:
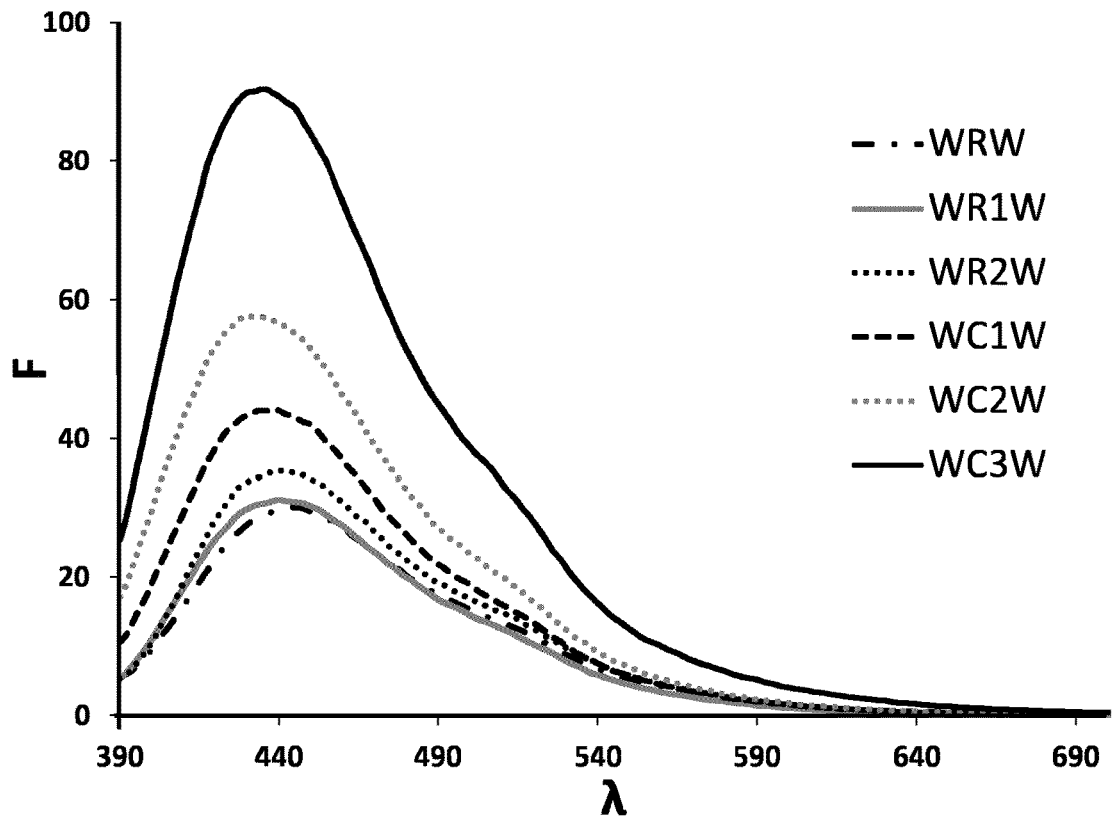
Figure 13A:
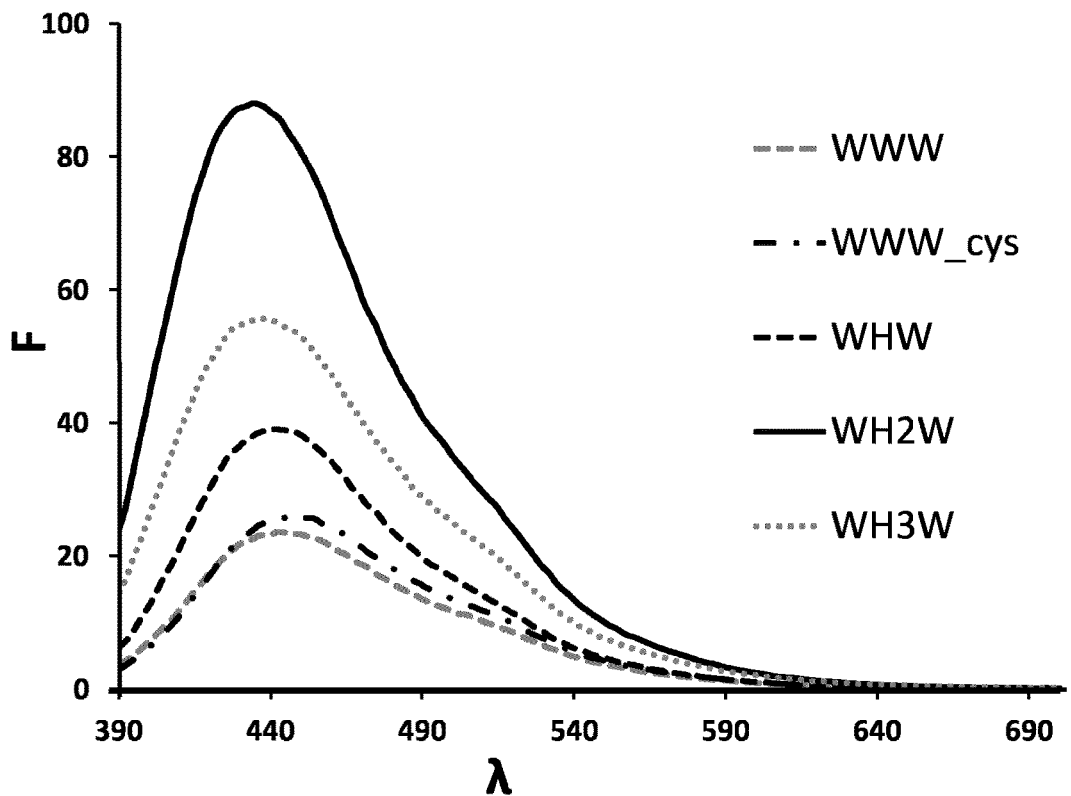
FIG. 13 describes the fluorescence emission spectra of different protein stabilized CuNCs. 13A, discloses the CuNCs formed by WWW, WWW_cys, WHW, WH2W and WH3W proteins; and 13B discloses the CuNCs formed by WC1W, WC2W, WC3W, WRW, WR1W and WR2W proteins. (F: Fluorescent intensity (arbitrary units); λ: wavelength (nm)).
Figure 13B:
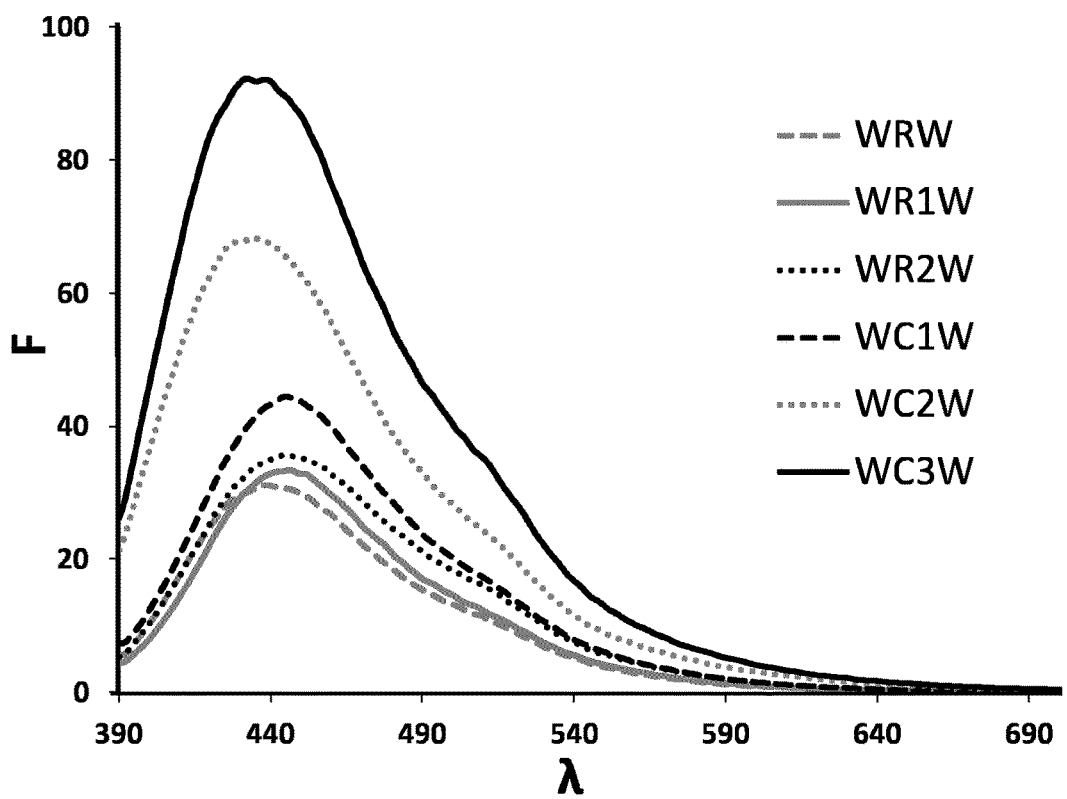

12. Comparison of the Efficiency in the Synthesis and Stabilization of Metal Nanoclusters Between the Design Proteins of the Invention and Possible CTPR-Based Random Mutants Containing Cysteine Residues The efficiency of the design proteins of the invention in comparison with possible CTPR-based random mutants containing cysteine residues in the synthesis and stabilization of metal nanoclusters was evaluated using the same experimental conditions (reducing agent, ratio protein:metal:reducing agent and reaction time). Results are provided in results section 5 ("Comparison of the efficiency in the synthesis and stabilization of metal nanoclusters between the design proteins of the invention and possible CTPR-based random mutants containing cysteine residues") (FIGS. 11, 12 and 13).

Using the proteins described in example 2 (WWW, WWW_cys, WC1W, WC2W, WC3W, WHW, WH2W, WH3W, WRW, WR1W and WR2W) the following protocol was followed:

1000 µL of protein at 20 µM were mixed with $CuSO_4$, $AgNO_3$ or $HAuCl_4$ (50 eq. respect to protein) first vortexing for 30 seconds and then leaved for 30 minutes to allow the adsorption of gold ions to the cysteines of the protein. Then, the reduction of the metal ions to metallic metal was achieved by adding sodium ascorbate (10 eq. respect to the metal). The reaction mixture was vortexed for 30 seconds and then was incubated at 37° C. for 72 h. Finally, the samples were washed several times with PBS using Amicon ultrafiltration tubes with a 10-kDa membrane to eliminate unreacted salts and then purified by FPLC. The fluorescence spectra of protein stabilized gold nanoclusters were collected using a Fluorimeter Perkin Elmer.

Figure 14:
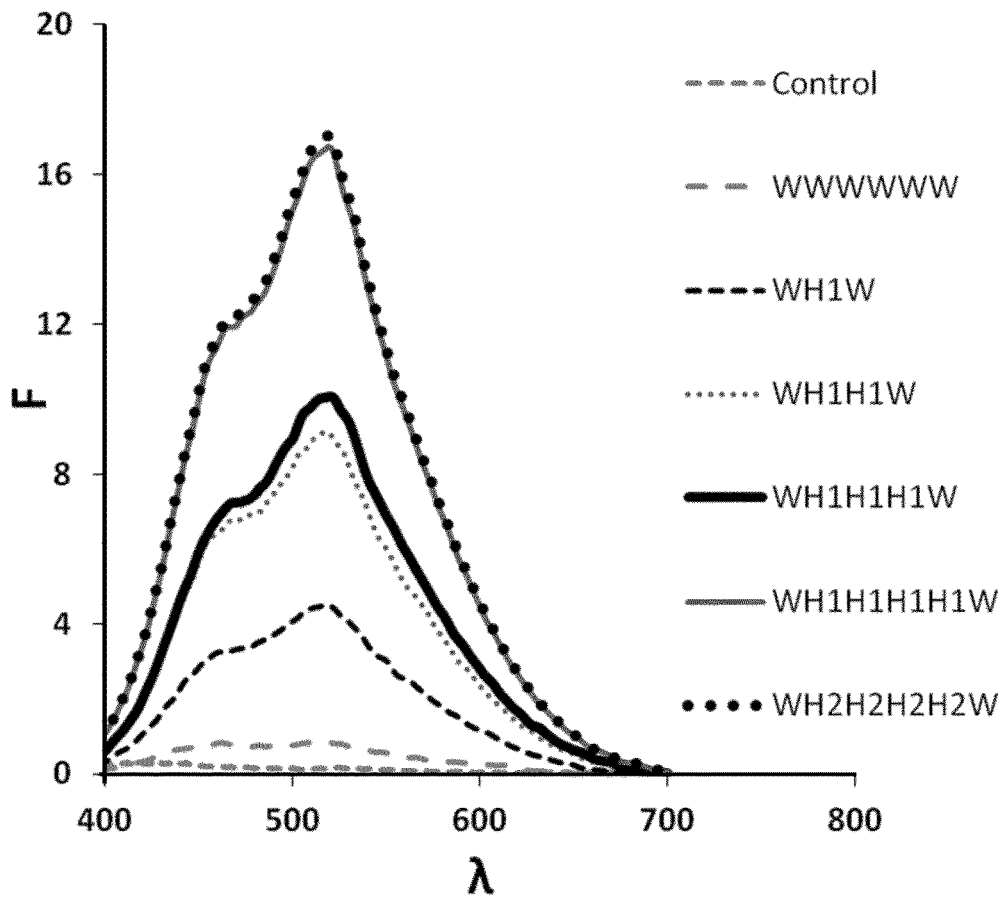
FIG. 14 shows the effect of the number and position of histidine residues in the fluorescence emission of protein-stabilized CdS NCs (WWWWWW, WH1W, WH1H1W, WH1H1H1W, WH1H1H1H1W and WH2H2H2H2W) (F: Fluorescent intensity (arbitrary units); λ: wavelength (nm); control, "control without protein").
Figure 15:
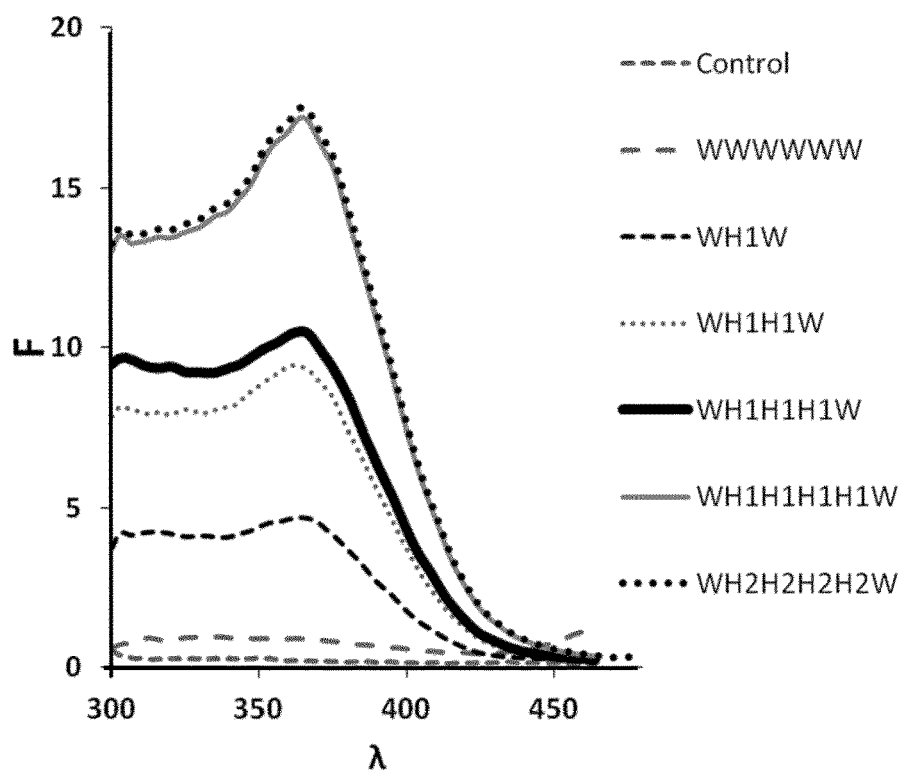
FIG. 15 shows the fluorescence excitation spectra of different protein stabilized CdS NCs (WWWWWW, WH1W, WH1H1W, WH1H1H1W, WH1H1H1H1W and WH2H2H2H2W). (F: Fluorescent intensity (arbitrary units); λ: wavelength (nm); control, "control without protein").

13. Synthesis of Protein-Stabilized CdS Nanoclusters:

2500 µL of protein at 5 µM were mixed with $Cd(CH_3CO_2)_2$ (0.4 mM) and vortexed for 30 seconds. Then the reaction was incubated for 60 minutes to allow the adsorption of Cd ions to the histidines of the protein. Then, the formation of CdS nanoclusters was achieved by adding sodium sulfide ($Na_2S$) (0.28 mM). The reaction mixture was vortexed for 30 seconds and then was incubated at 37° C. for 5 days. Finally, the samples were washed several times with PBS using Amicon ultrafiltration tubes with a 10-kDa membrane to eliminate unreacted salts and then purified by FPLC. The fluorescence spectra of protein stabilized CdS NCs were collected using a Fluorimeter Perkin Elmer. The results are provided in the results section number 6 ("Fluorescent CdS nanoclusters comprising CTPR variant with coordinating residues based on histidine clamps") (FIGS. 14 and 15).

14. Protein-NCs Stability Determination:

The stability of the WHW-CuNCs at 10 µM in PBS and human plasma was examined during one week at room temperature by fluorescent spectrophotometry using a microplate reader.

15. Preparation of Cell Culture for Viability and Internalization Studies:

MCF7 cell line was grown as monolayer in Dulbecco's Modified Eagle's Medium (DMEM) supplemented with fetal bovine serum (FBS) at a final concentration of 10%, 2 mM L-glutamine, 0.25 µg/mL fungizone and 100 units of penicillin and 100 µg/mL streptomycin. All the media, serum, L-glutamine, fungizone and antibiotics were purchased from GIBCO. The cell line was maintained at 37° C. in a humidified atmosphere consisting of 75% air and 5% $CO_2$ in an incubator. 500 µL of protein stabilized CuNCs dispersed in PBS were sonicated for redispersion purposes during 5 minutes. Then, protein stabilized CuNCs were diluted in medium containing 10% FBS at the desired concentration. The resulting sample was filtered through a 0.22 µm Millex-GP filter (Merck-Millipore Darmstadt, Germany) and sonicated again for 1 minute. Cells were incubated with protein stabilized CuNCs for 24 h. Then, cell media with protein stabilized CuNCs dispersed was removed and cells were washed with phosphate buffered saline (PBS) for complete removal of protein stabilized CuNCs from cell medium. Then fresh cell media was added to continue further viability and internalization studies.

16. In Vitro Cytotoxicity Assays:

Resazurin dye (Sigma-Aldrich) has been broadly used as a reliable indicator of cell viability in proliferation and cytotoxicity assays. To assess cell viability, MCF7 cells were cultured on a 24-well plate at a density of 2.5×104 cells per well in 500 µl of complete medium. After 24 h, the growth medium was removed and cells were then incubated 24 h at 37° C. in the presence of different concentrations of protein stabilized CuNCs (2, 5, 10 and 20 µM). After incubation, cells were washed three times with PBS, and then DMEM supplemented with 10% FBS was added to cell culture, and maintained at 37° C. and 5% $CO_2$ incubator. After 72 h, the medium was replaced with DMEM supplemented with 10% FBS, and 10% of Resazurin dye (1 mg/ml PBS). Cells were maintained at 37° C. and 5% $CO_2$ incubator for 3 hours and then, a Synergy H4 microplate reader was used to determine the amount of Resazurin reduced by measuring the absorbance of the reaction mixture ($\lambda exc=570$ nm, $\lambda em=600$ nm). 600 µl of 10% of resazurin dye was added to empty wells as a negative control. The viability of the cells was expressed as the percentage of absorption of treated cells in comparison with control cells (without nanoparticles). All experiments were carried out in triplicate.

17. Use of the Protein-Stabilized Metal NC as Temperature Sensor:

Blue-emitting WHW stabilized CuNCs synthetized as previously describe the point 5 (Synthesis of protein-stabilized copper nanoclusters with different emission colors) were used as temperature sensor as follows: The fluorescence emission intensity of protein stabilized copper nanoclusters at different temperatures were recorded at 430 nm when the sample was excited at 370 nm using a Fluorimeter Perkin Elmer.

18. Use of the Protein-Stabilized Metal NC as Live Imaging Tool:

The fluorescence intensities of 20 µM solution of WHW stabilized AgNCs synthetized, as previously describe the point 3 of the materials and methods, 20 µM solution of Green Fluorescent Protein (GFP) and 20 µM solution of 4',6-diamidino-2-phenylindole (DAPI) were recorded at different times under continuous mercury arc lamp illumination using a Leica DM3 fluorescence microscope. The fluorescence intensities were quantified using Image J software.

Results:

Fluorescent Metal Nanoclusters Comprising CTPR Variant with Coordinating Residues Based on Histidine Clamps:

The potential of designed repeat proteins as templates for the synthesis and stabilization of Cu NCs was explored (FIG. 1).

The capability of CTPR proteins, formed by 3 modules (so-called CTPR3), to act as templates for the synthesis and stabilization of Cu NCs and, the effect of the presence and position of a specific metal-binding site (Histidine (His) clamp) in the protein structure on the formation and stabilization of metal NCs was analyzed. In addition, the versatility of the CTPR protein to stabilize NCs of different nobel metal NCs (Au and Ag) and the possibility of generate Cu NCs with different emission colors was tested. Finally, the potential application of these metal NCs in the field of cellular imaging as non-specific cellular marker or specific cellular marker using an CTPR proteins which include in their structure a localization peptide, in this case SV40 large T antigen nuclear localization signal (NLS) was evaluated.

Three different CTPR3 proteins were designed, expressed and produced for the synthesis and stabilization of Cu NCs. First a His clamp was designed at the modular level by introducing two His residues at positions 5 and 9 within the CTPR repeat to generate a modified CTPR unit (H) (table 1). By combining H modules and wild type CTPR modules (W), three CTPR3 proteins were generated: CTPR3-WWW composed by three identical wild type CTPR modules; CTPR3-WHW composed by two wild type CTPR module (W) and one module that contains a metal-binding His clamp (H) localized at the central repeat; and CTPR3-HWW in which the H module was localized at the N-terminal repeat. The three designed CTPRs were tested for the generation of protein-stabilized Cu NCs. To investigate the effects of the protein sequence, ratio protein:metal:reducing agent and reaction time, similar protocols have been developed and applied for all the syntheses. The absorption and fluorescence spectrum of the samples were acquired showing in all the cases characteristic fluorescence corresponding to protein stabilized CuNCs (FIG. 1). First, we evaluated the effect of the protein sequence in the synthesis and stabilization of Cu NCs using the same experimental conditions (reducing agent, ratio protein:metal:reducing agent and reaction time) as we have described in the material and method section. As shown in FIG. 1, the Cu NCs with larger fluorescence emission intensity were obtained using the CTPR3-WHW protein. After evaluating the importance of the presence and position of the His clamp, the CTPR3-WHW protein as ideal scaffold for the synthesis and stabilization of Cu NCs was selected. Then, the role of ratio protein:metal:reducing agent and reaction time in the synthesis and stabilization of Cu NCs using the CTPR3-WHW protein in order to optimize the properties of the final Cu NCs was evaluated. The fluorescent properties of the stabilized Cu NCs increased over the time from 24 h to 72 h. The fluorescent properties of the stabilized Cu NCs were also improved increasing the ratio metal:protein from 5:1 to 50:1 and also increasing the ratio reducing agent:metal from 10:1 to 100:1 was observed. Finally the Cu NCs synthesized using 50:1 as ratio metal:protein, 100:1 as ratio reducing agent:metal and 72 h as reaction time was selected and fully characterized because it resulted in the larger fluorescence emission intensity.

Figure 2:
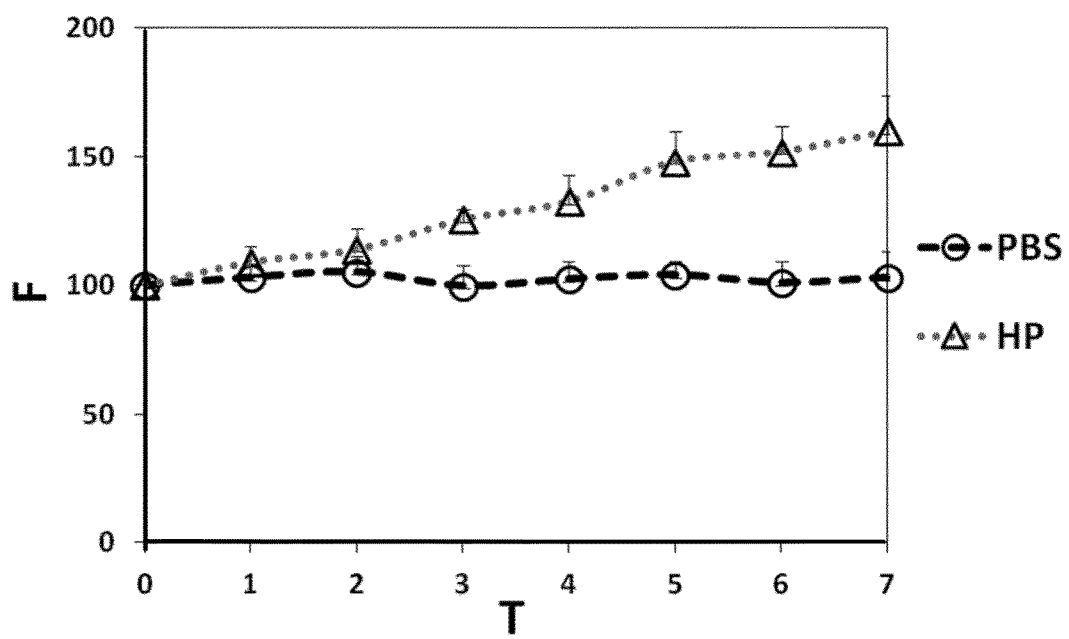
FIG. 2 WHW-CuNCs stability in Phosphate Saline Buffer (PBS) and in human plasma (HP). (F: Fluorescence intensity (%); T: Time (days)).

The UV-visible spectrum of the protein-stabilized Cu NCs (WHW-CuNCs) compared with the UV-visible spectrum of the protein alone (WHW), at the same concentration, showed in addition to the characteristic protein absorption at 280 nm the presence of a clear peak around 370 nm. The excitation spectrum showed a single peak with a maximum at 370 nm. The fluorescence emission spectrum of the product consisted of a single peak with a maximum at 450 nm, when excited at 370 nm. The fluorescence quantum yield ($\phi$) was determined to be 10% ($\lambda$ex: 370 nm) using anthracene as standard. In addition to the photophysical and structural characterization, the structural integrity of the CTPR protein template is very important for future applications of the protein-NCs hybrid structures. Circular dichroism (CD) measurements did not show any decrease in the α-helical secondary structure content of the protein in the WHW-CuNCs complex following NCs formation, therefore it can be ensured that WHW was stable under the NCs synthesis conditions and that the stabilized NCs did not perturb the structure of the protein scaffold. TEM measurements indicated the presence of small Cu NCs (The average size of individual Cu NCs was calculated as 0.9±0.2 nm). Further, the application of the WHW-CuNCs in field of bioimaging and biolabelling requires good photostability and biocompatibility. In order to check properly the photostability of WHW-CuNCs in physiological conditions, stability studies were performed in phosphate buffered saline (PBS) and human plasma (HP). As shown in FIG. 2, WHW-CuNCs had very good stability in PBS and HP during one week at room temperature, remaining their fluorescent properties nearly constant in the case of PBS and increasing their fluorescent properties in the case of HP.

An in vitro cytoxicity study of WHW-CuNCs was examined by Alamar blue cell viability assay. Viability assay was performed to evaluate the possible cytotoxicity of the WHW-CuNCs by incubation in MCF7 breast cancer cells. The concentrations of the WHW-CuNCs used were 2-20 µM. MCF7 breast cancer cells in DMEM were incubated with different concentrations of WHW-CuNCs in standard cell culture conditions. Following 72 h of incubation, the cells viability was determined by Alamar blue cell viability assay. The results indicated that the WHW-CuNCs had not cytotoxic effect even at a high concentration.

Figure 3:
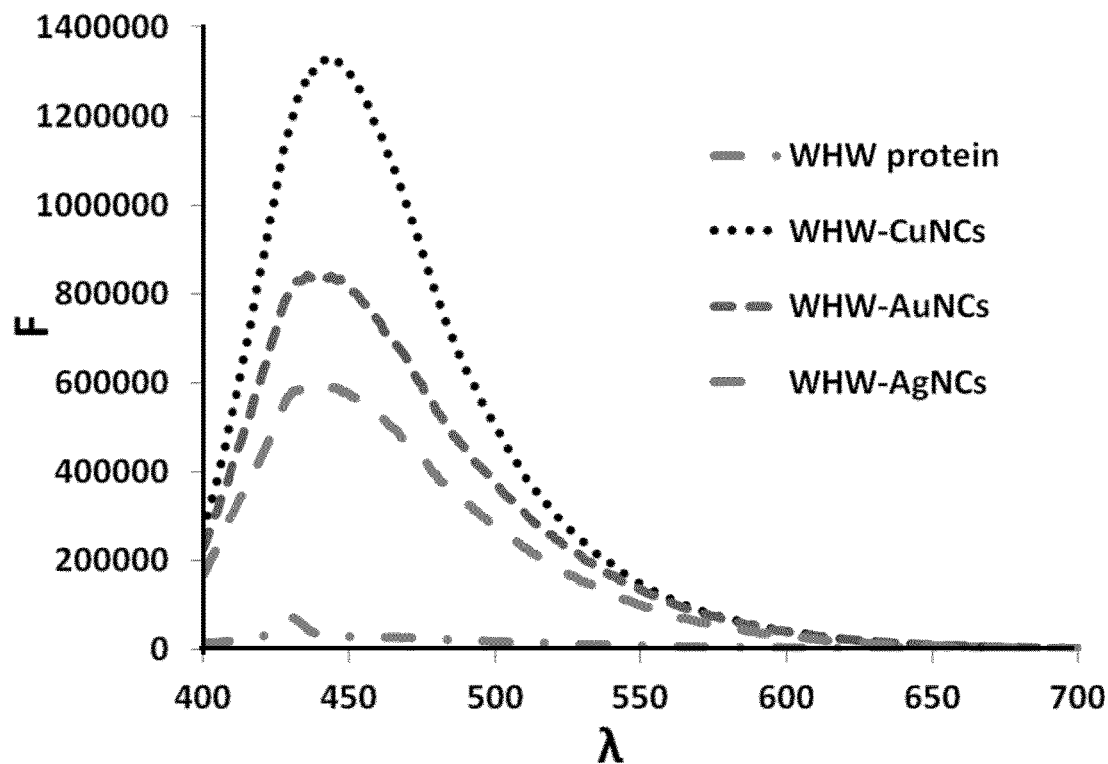
FIG. 3 shows the effect of the presence of a particular metal (Cu, Au and Ag) in the fluorescent spectra of WHW-stabilized NCs.

In addition, the versatility of the CTPR protein to stabilize NCs of different nobel metal NCs (Au and Ag) was tested obtaining similar results to those obtained when using Cu as metal, but less fluorescence intensity (FIG. 3). Also, the possibility of generating Cu NCs with different emission colors changing some synthesis protocol parameters was evaluated, as indicated in the materials and methods section. Cu NCs with different color emission, from UV to red, were obtained wherein the excitation wave lengths were: 320, 370, 440, 485, and 530 nm and the emission wave lengths were 405, 450, 520, 565, and 605 nm, respectively (data not shown). Therefore the NCs stabilized with the proteins of general formula (II) showed a surprising versatility in terms of fluorescence color emission.

The results obtained for the CTPR proteins, formed by WHHW (CTPR4) and by WHHHW (CTPR5) were the same as described herein for the WHW protein for the CuNCs (data not shown).

Finally, the potential application of the protein stabilized CuNCs in the field of cell labeling as non-specific cellular marker or specific cellular marker using as template WHW proteins and WHW which included in their structure a nuclear localization sequence (NLS) (NLS-WHW) was evaluated. The NLS-WHW protein was constructed from WHW protein by molecular biology techniques following the procedure described before. First, it was confirmed that the presence of the nuclear localization sequence in the structure of the WHW protein did not affect the synthesis and stabilization of the Cu NCs and also that the NLS-WHW stabilized Cu NCs (NLS-WHW-CuNCs) had similar fluorescent properties to WHW-CuNCs. The proof of concept evaluation of the protein stabilized Cu NCs for cell labeling was pursued by incubating MCF7 cells with WHW-CuNCs and NLS-WHW-CuNCs for 1 h in Dulbecco's Modified Eagle's Medium (DMEM) at 37° C. After removal of the medium, the cells were washed thoroughly with PBS to remove free unbound WHW-CuNCs and NLS-WHW-CuNCs and finally cells were imaged by fluorescence microscopy. In comparison, cells treated with WHW-CuNCs exhibited a homogeneous fluorescent signal inside all cell and cells treated with NLS-WHW-CuNCs exhibited a localized fluorescent signal inside cell nucleus and nucleus membrane. These results clearly demonstrated the utility of the protein stabilized CuNCs in live cell labeling as non-specific cellular biomarker (as exemplified by WHW-CuNCs) or specific nuclear biomarker (as exemplified by NLS-WHW-CuNCs). Taking in to account that TPR protein cannot be internalized by cells it can be assumed that the internalization of TPR-CuNCs is provided by the presence of the CuNCs in the structure of the TPR proteins.

Figure 4:
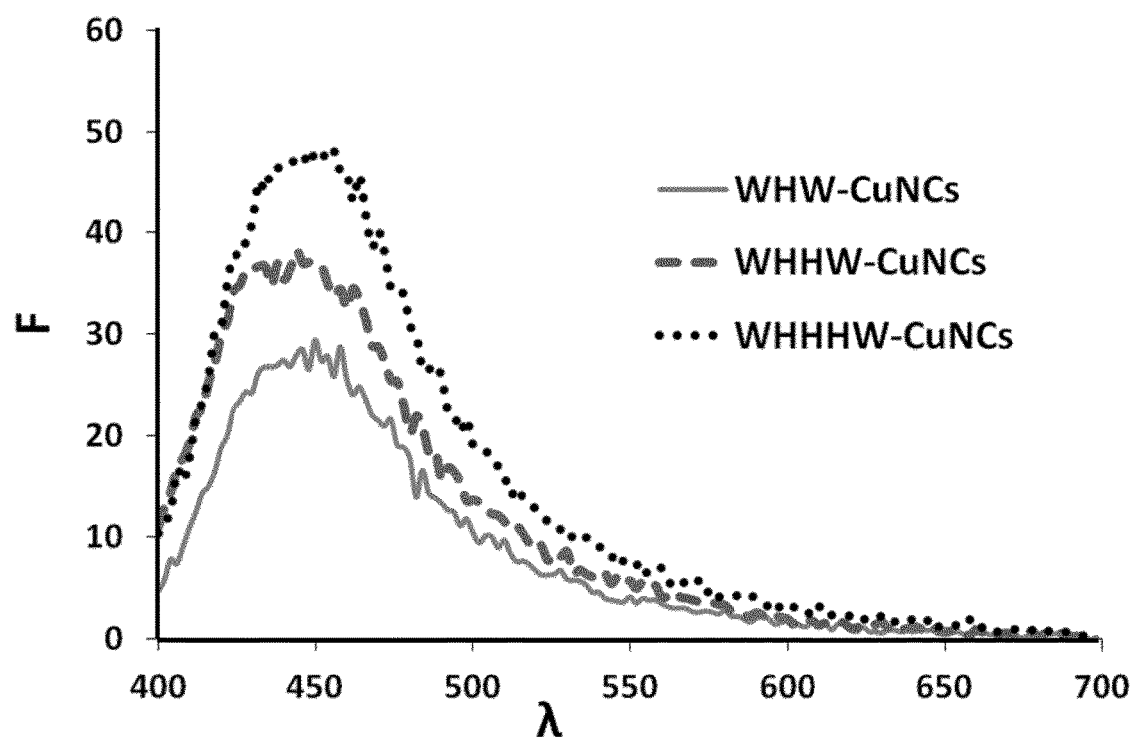
FIG. 4 shows the effect in the fluorescence spectra of the number of H modules in cooper NCs (F: Fluorescence intensity (arbitrary units); λ: wavelength (nm)).

Moreover, it was studied the effect of the presence of different number of a specific metal-binding site (Histidine (His) clamp) in the protein structure on the formation and stabilization of metal NCs. The fluorescent properties of nanoclusters formed by WHW, WHHW, and WHHHW proteins were tested. As can be observed in FIG. 4 there was an improvement on the fluorescent properties of the stabilized CuNCs when the number of a specific metal-binding site (Histidine (His) clamp) in the protein structure was increased from 1 to 3.

In conclusion, it has been demonstrated that designed repeat proteins can be used as versatile templates for the synthesis and stabilization of noble metal NCs. It has been described the use of different modules as cassettes to construct different CTPR proteins. In this example it is shown the design of CTPR protein that can contain in its structure a localization peptide as targeting agent but the same procedure could be used for many goals. The protein-stabilized Cu NCs showed high photo-luminescence quantum yield, high photostability and good biocompatibility. They could be used for labelling cells, nucleus or any other cellular compartment. The combination of the photoluminescence properties, stability in physiological conditions and their low cytotoxicity make the metal NCs of the present invention an ideal choice for biological and biomedical applications in vitro as well as in vivo.

Fluorescent Metal Nanoclusters Comprising CTPR Variant with Coordinating Residues Based on Cysteine Clamps:

The capability of CTPR proteins, formed by different numbers of CTPR modules, to act as templates for the synthesis and stabilization of metal NCs and, the effect of the presence and position of specific metal-binding sites composed by different numbers of cysteine residues in the protein structure on the formation and stabilization of metal NCs was explored.

Ten different CTPRs proteins were designed, expressed and produced for the synthesis and stabilization of metal NCs (Cu, Ag and Au) by combining C, C1, C2 and C3 modules with wild type CTPR modules (W): WCC1W, WC1C1W, WC1C1C1W, WC2C2W, WC2C2C2W, WC3C3W, WC3C3C3W, WC3C3C3C3W, WC3C3C3C3C3W and WC3C3C3C3C3C3W, as indicated in table 2 and in materials and methods section. The designed CTPRs were tested for the generation of protein-stabilized metal NCs. First, the effect of the protein sequence in the synthesis and stabilization of metal NCs using the same experimental conditions as it has been described in the materials and methods was evaluated. The fluorescence spectra of the samples were acquired showing in all the cases characteristic fluorescence corresponding to protein stabilized metal NCs.

Also the protein WWW_Cys was created as indicated by Couleaud P et al. 2015 as a comparative for the importance of the location of the cysteine residue.

Figure 5:
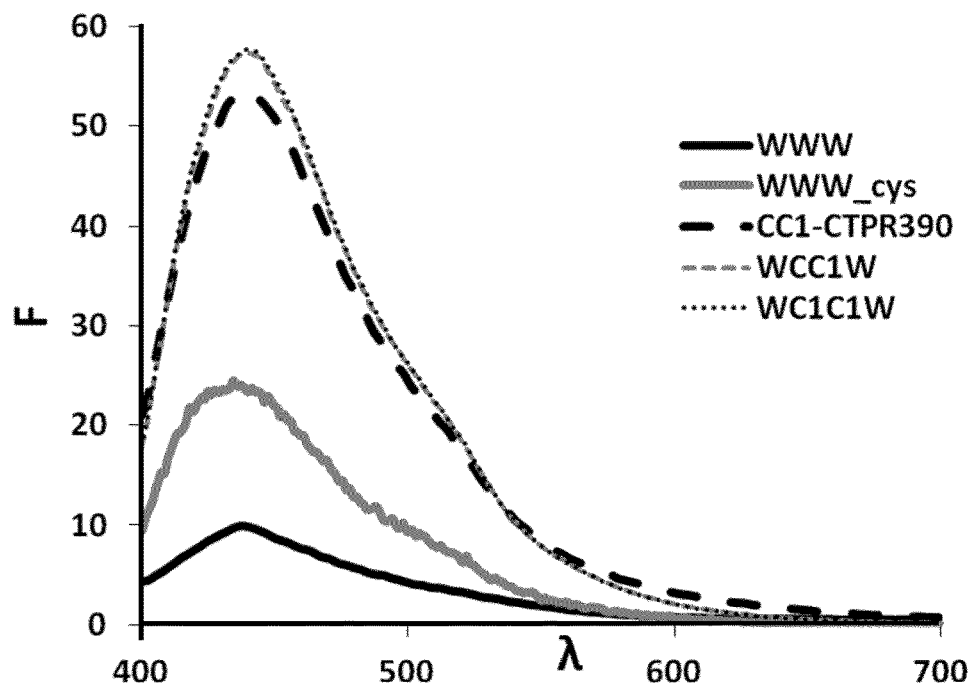
FIG. 5 represents a comparative of the fluorescence spectra of different protein-stabilized AuNCs and shows the effect of the cysteine clamp. (F: Fluorescence intensity (arbitrary units); λ: wavelength (nm)).

As observed in FIG. 5, the presence of cysteine residues in the protein structure favors the synthesis and stabilization of AuNCs. The WWW protein with no cysteines did not result in a significant production of nanoclusters. The presence of a single cysteine residue in the protein sequence in the C-terminal end (WWW_Cys) (SEQ ID NO: 107), showed a weak fluorescence emission related to the formation of nanoclusters (see also FIGS. 7-9). Remarkably, the introduction of the designed cysteine clamps inside the protein increased the fluorescence intensity more than 5 times. In addition, it was observed that the combination of cysteine modules CC1 and C1C1 gave rise to AuNCs with the same fluorescent properties. Finally, it was observed that the position of the modules with the cysteine clamps in the protein structure is not so important for the synthesis and stabilization of AuNCs as in the case of the histidine clamp for the synthesis and stabilization of CuNCs, since WCC1W-AuNCs and CC1-CTPR390-AuNCs showed similar fluorescent properties.

Figure 6A:
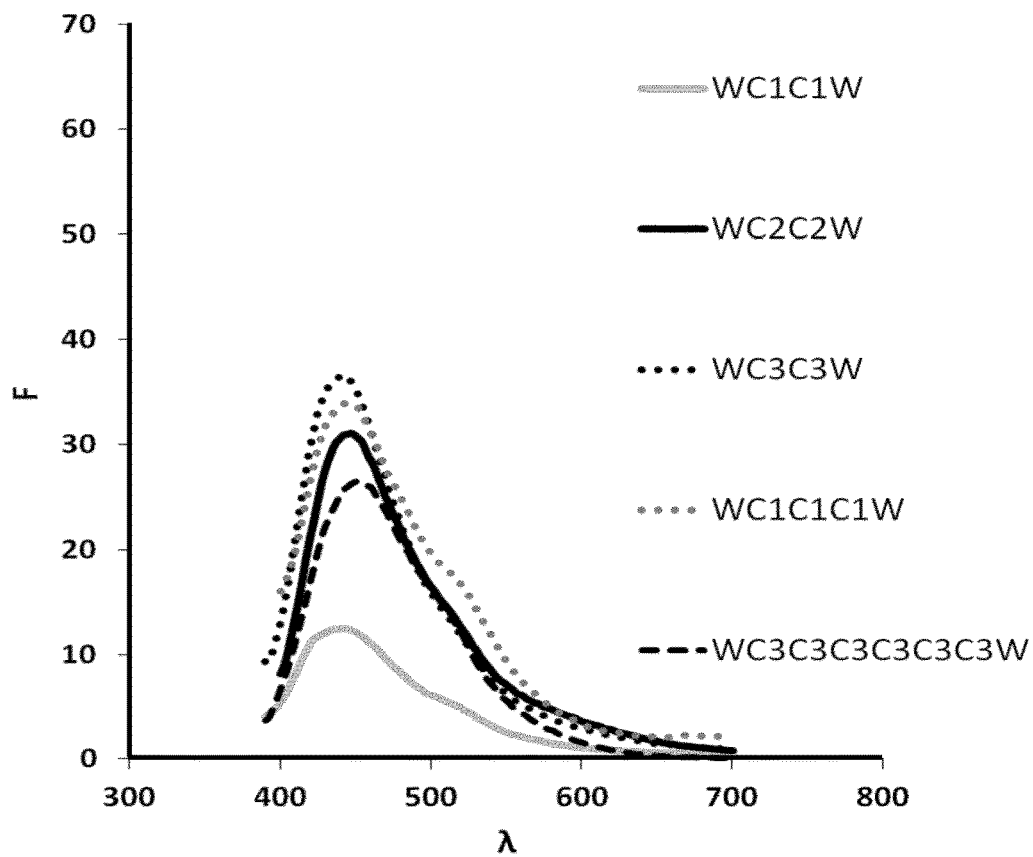
FIG. 6 shows the effect of the amount of cysteine residues in the fluorescence of protein-stabilized AuNCs. 6A discloses the AuNCs formed by WC1C1W, WC2C2W, WC3C3W, WC1C1C1W and WC3C3C3C3C3W proteins; whereas 6B discloses the AuNCs formed by WC2C2C2W, WC3C3C3W, WC3C3C3C3W and WC3C3C3C3C3W proteins. (F: Fluorescence intensity (arbitrary units); λ: wavelength (nm)).
Figure 6B:
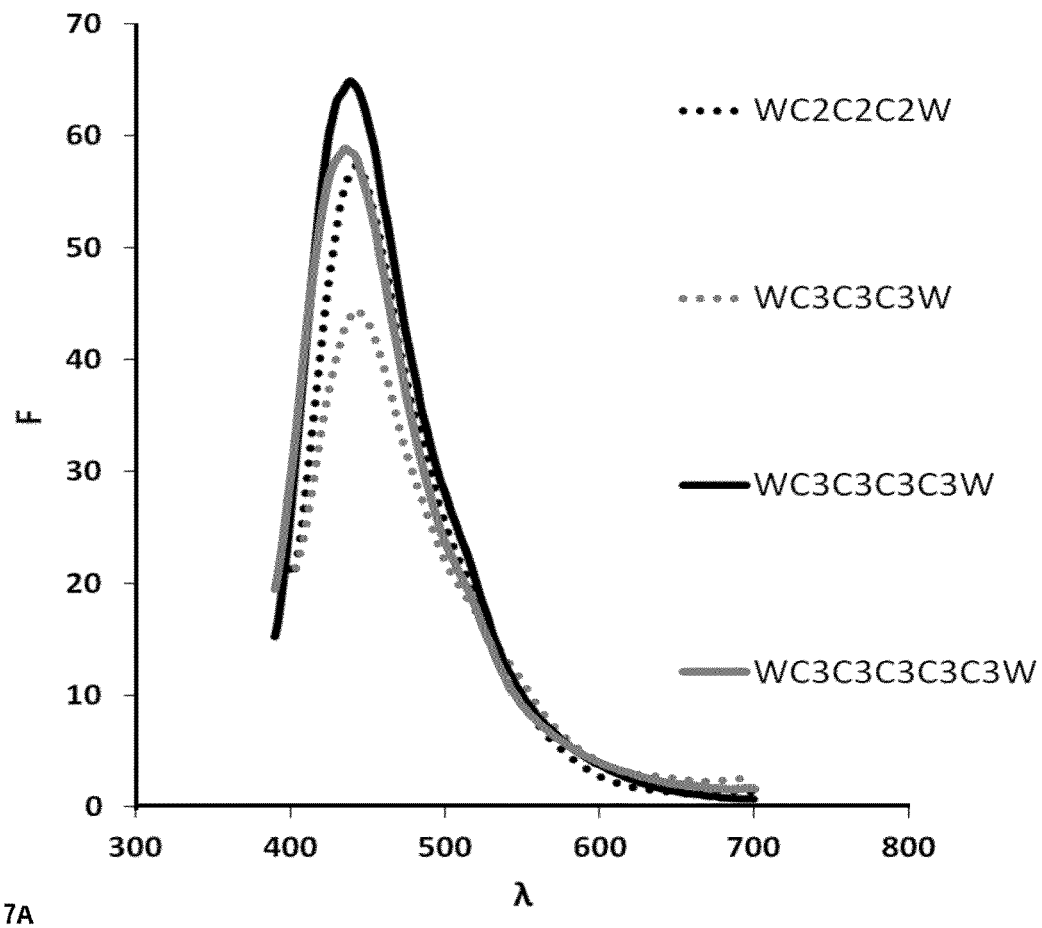

As shown in FIG. 6, AuNCs with larger fluorescence emission intensity were obtained using the different CTPR proteins. After evaluating the importance of the presence and position of the Cys residues, it was observed an improvement on the fluorescence properties of the stabilized AuNCs by increasing the number of Cys residues up to 16-20 and a decrease of the fluorescence properties of the stabilized AuNCs when the number of Cys residues increased above 20. The excitation spectrum showed in all cases a single peak with a maximum at 370-380 nm. The fluorescence emission spectra of the products consisted of a single peak with a maximum at 440-450 nm, when excited at 370-380 nm (FIG. 6).

Figure 8A:
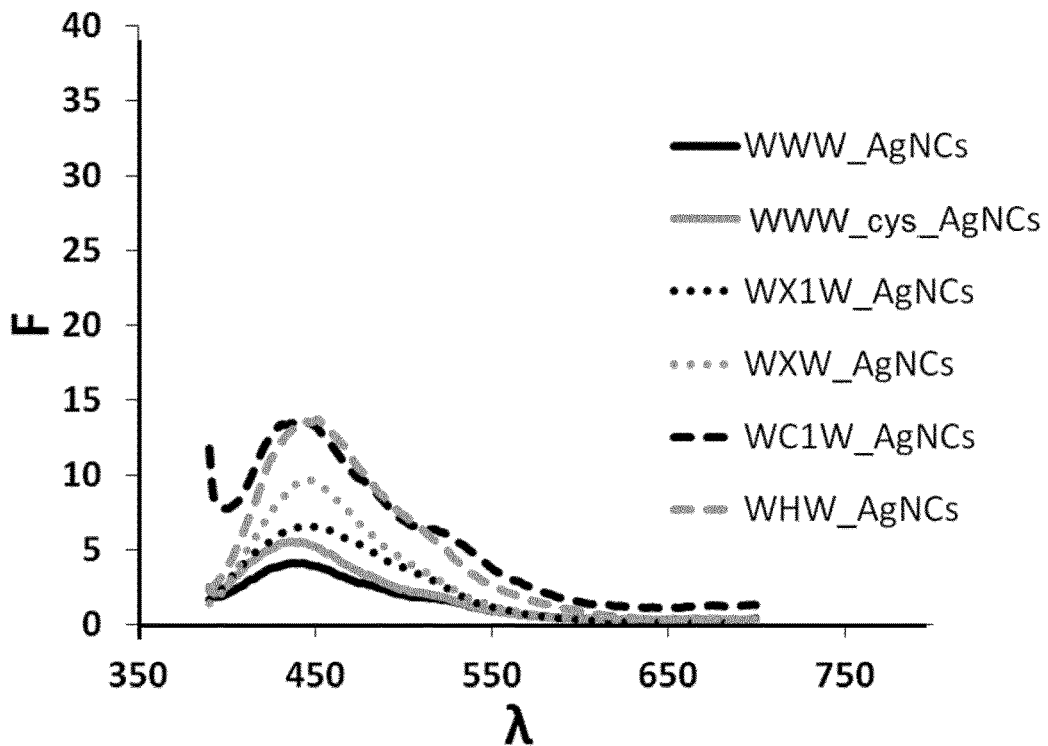
FIG. 8 shows the fluorescence emission spectra of different protein stabilized AgNCs. 8A, discloses the AgNCs formed by WWW, WWW_cys, WX1W, WXW, WC1W and WHW proteins. 8B discloses the AgNCs formed by WC1C1W, WC2C2C2W, WC3C3C3W, WC3C3C3C3W and WC3C3C3C3C3W proteins. (F: Fluorescence intensity (arbitrary units); λ: wavelength (nm)).
Figure 8B:
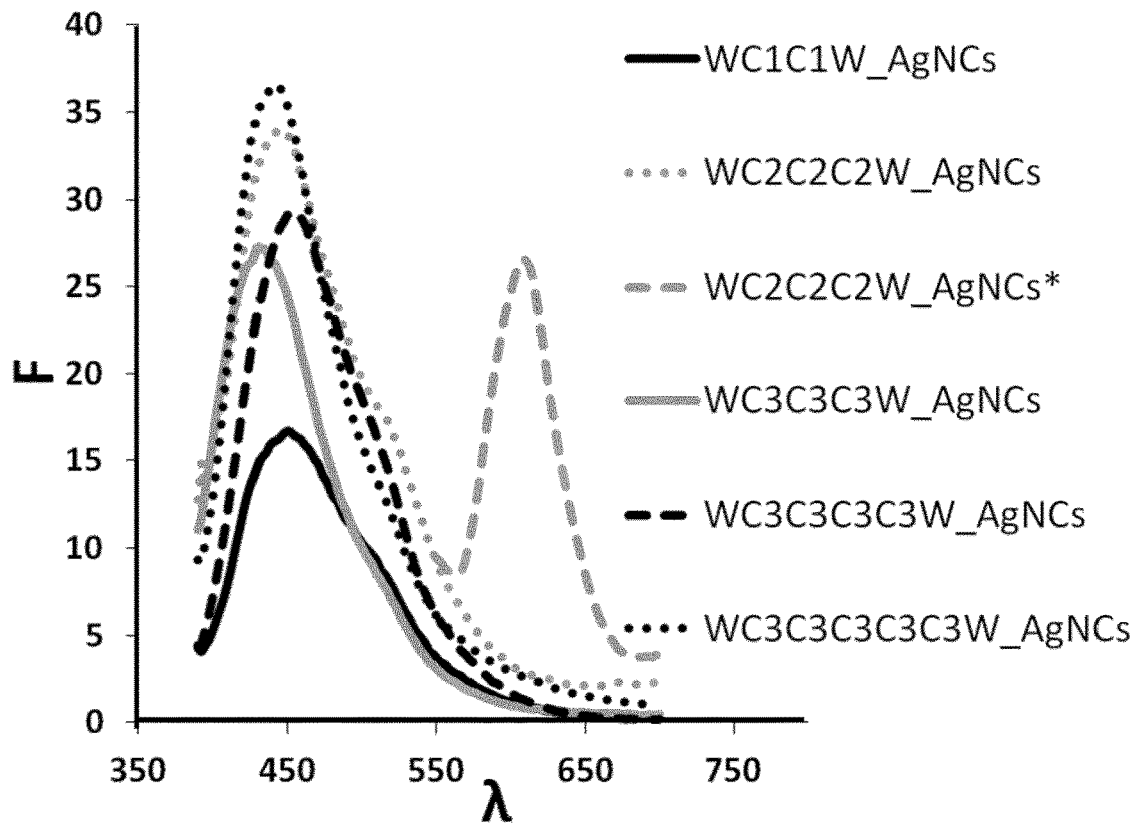
Figure 9A:
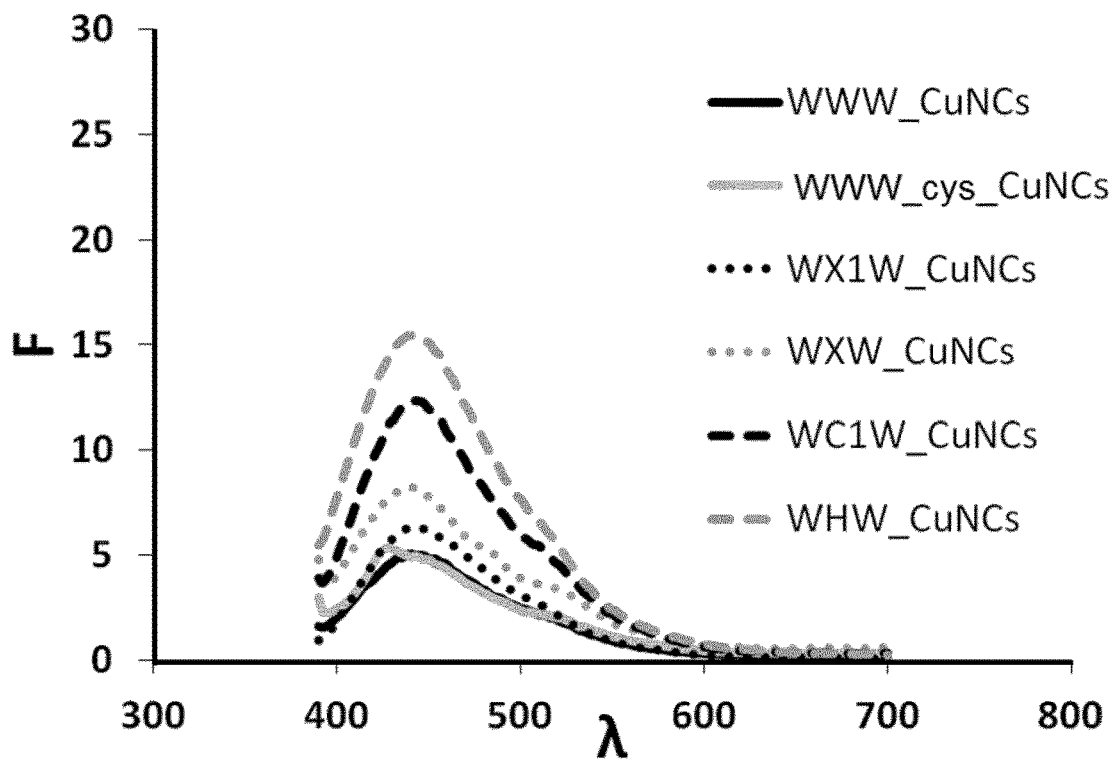
FIG. 9 describes the fluorescence emission spectra of different protein stabilized CuNCs. 9A, discloses the CuNCs formed by WWW, WWW_cys, WX1W, WXW, WC1W and WHW proteins. 9B discloses the CuNCs formed by WC1C1W, WC2C2C2W, WC3C3C3W, WC3C3C3C3W and WC3C3C3C3C3W proteins, (F: Fluorescence intensity (arbitrary units); λ: wavelength (nm)).
Figure 9B:
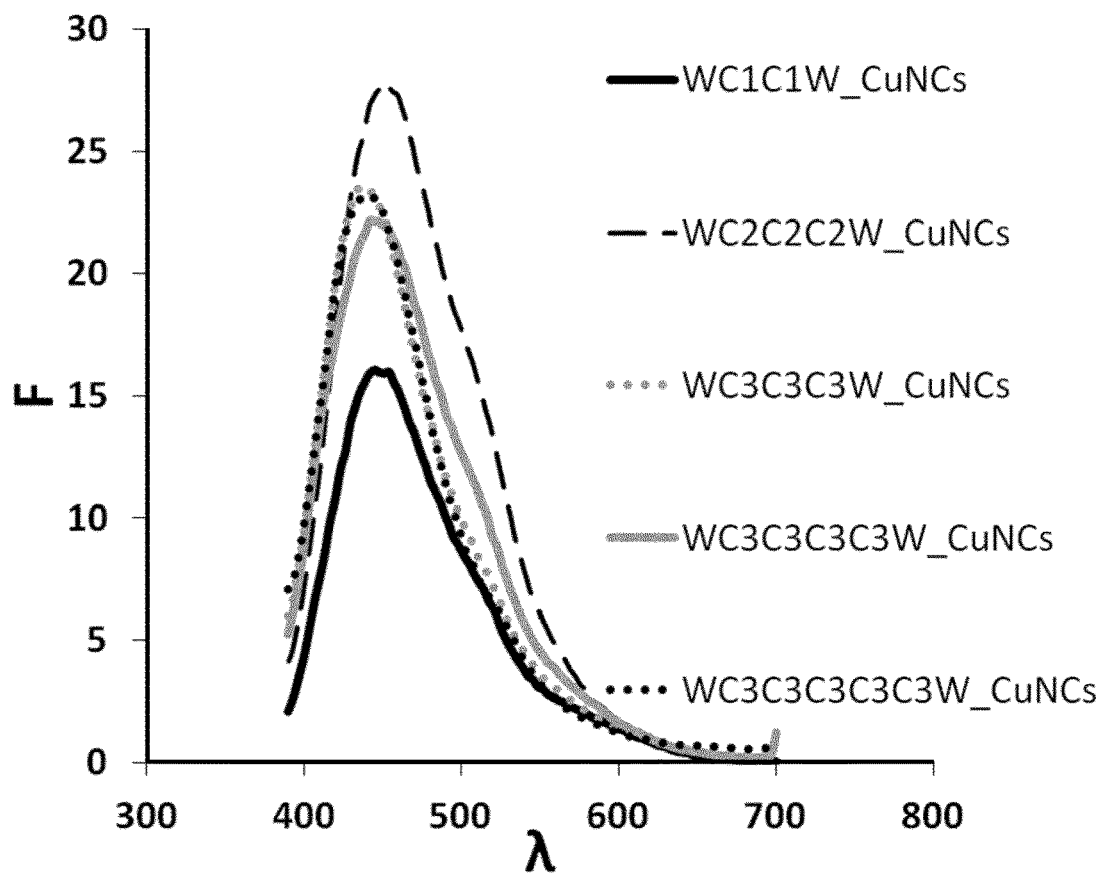

AuNCs, AgNCs and CuNCs with larger fluorescence emission intensity were obtained using the different CTPR proteins (obtained using the same experimental conditions explained in materials and methods) (WWW, WX1W, WXW, WC1W, WHW, WC1C1W, WC2C2C2W, WC3C3C3W, WC3C3C3C3W and WC3C3C3C3C3W). The fluorescence spectra of the samples were acquired showing in all the cases characteristic fluorescence corresponding to protein stabilized metal NCs. After evaluating the importance of the presence and position of the Cys and/or His residues, a remarkable improvement in the fluorescent properties of the stabilized metal NCs was detected increasing the number of Cys residues up to 16-20 (see FIGS. 7, 8 and 9). The fluorescence emission spectrum of the main product consisted of a single peak with a maximum at 440-460 nm (blue emission), when excited at 370 nm. In the case of Ag nanoclusters stabilized on WC2C2C2W scaffold a red emission with a maximum at 620 nm was obtained when the sample was excited at 455 nm (WC2C2C2W_AgNCs*) whereas a single peak with maximum at 440-460 nm was obtained when the sample was excited at 370 nm (WC2C2C2W_AgNCs) (FIG. 8).

Effect of the Ratio of the Metal on the Formation and Stabilization of the NCs:

Here it was explored the effect of the presence and position of specific metal-binding sites composed by different numbers of cysteine residues in the protein structure on the formation and stabilization of different metal (Au, Ag and Cu) NCs. Also it was explored the effect of the ratio of Au and Ag on the formation and stabilization of different mixed metal (Au, Ag and Cu) NCs using the same protein as template, in this case the WC2C2C2W.

For designed CTPRs, WC2C2C2W, WC3C3C3W, WC3C3C3C3W and WC3C3C3C3C3W the fluorescence spectra of the samples were acquired showing in all the cases characteristic fluorescence corresponding to protein stabilized metal NCs.

Comparison between 37° C. and 50° C. as reaction temperature in the formation of the metal NCs was performed.

AuNCs, AgNCs and CuNCs with larger fluorescence emission intensity were obtained using the different CTPR proteins of the present invention as explained above. After evaluating the importance of the presence and position of the Cys residues, a general improvement in the fluorescent properties of the stabilized metal NCs was observed increasing the number of Cys residues up to 20, using 50° C. as reaction temperature. The fluorescence emission spectrum for most of the reactions consisted in a single peak with a maximum at 440-460 nm (blue emission), when excited at 360-380 nm. In deep, the AuNCs with the best fluorescence emission intensity was obtained with WC3C3C3C3C3W (20 Cys residues) at 50° C. In the case of Ag, the AgNCs with largest fluorescence emission intensity were obtained with WC3C3C3C3W (16 Cys residues) at 50° C. Finally, In the case of Cu, the CuNCs with the largest fluorescence emission were obtained with WC3C3C3C3C3W (20 Cys residues) at 50° C. Interestingly, in the case of AgNCs stabilized by WC2C2C2W (9 Cys residues) a dual emission was observed, blue emission with an excitation of 360-380 nm and red emission with an excitation of 430-460 nm.

Also the effect of the ratio of Au and Ag on the synthesis, stabilization and fluorescent properties of different mixed Au—Ag NCs using the same protein as template, in this case the WC2C2C2W, was explored.

The AuNCs, AgNCs and mixed AuAgNCs with larger fluorescence emission intensity were obtained using the WC2C2C2W CTPR protein. After evaluating the importance of the Au/Ag ratio, we observed: an improvement of the fluorescent properties of the stabilized Au NCs when adding Ag in a molar ratio of 9:1 (Au:Ag), no effect on the fluorescent properties of the stabilized Au NCs when adding Ag in ratios of 4:1 and 3:1 (Au:Ag) and a decrease of the fluorescent properties of the stabilized Au NCs when adding Ag in a ratio of 2:1 (Au:Ag).

Fluorescent Gold Nanoclusters Comprising CTPR Variants Containing Several Modules with Coordinating Residues Based on Histidine Clamps in Comparison with Cysteine Clamp:

The effect of the nature and position of specific metal-binding sites, composed by the same number of cysteine or histidine residues in the CTPR protein structure, on the formation and stabilization of gold NCs was explored.

Three different CTPRs proteins with 6 CTPR modules were designed, expressed and produced for the synthesis and stabilization of gold NCs. The following proteins were generated by combining C3, H1 and H2 modules with wild type CTPR modules (W): WC3C3C3C3W, WH1H1H1H1W and WH2H2H2H2W, as indicated in table 2 and in materials and methods section.

The designed CTPRs were tested for the generation of protein-stabilized gold NCs. The effect of the protein sequence in the synthesis and stabilization of gold NCs using the same experimental conditions described in the materials and methods was evaluated. The fluorescence spectra of the samples were acquired showing in all the cases characteristic fluorescence corresponding to protein stabilized gold NCs.

Figure 10:
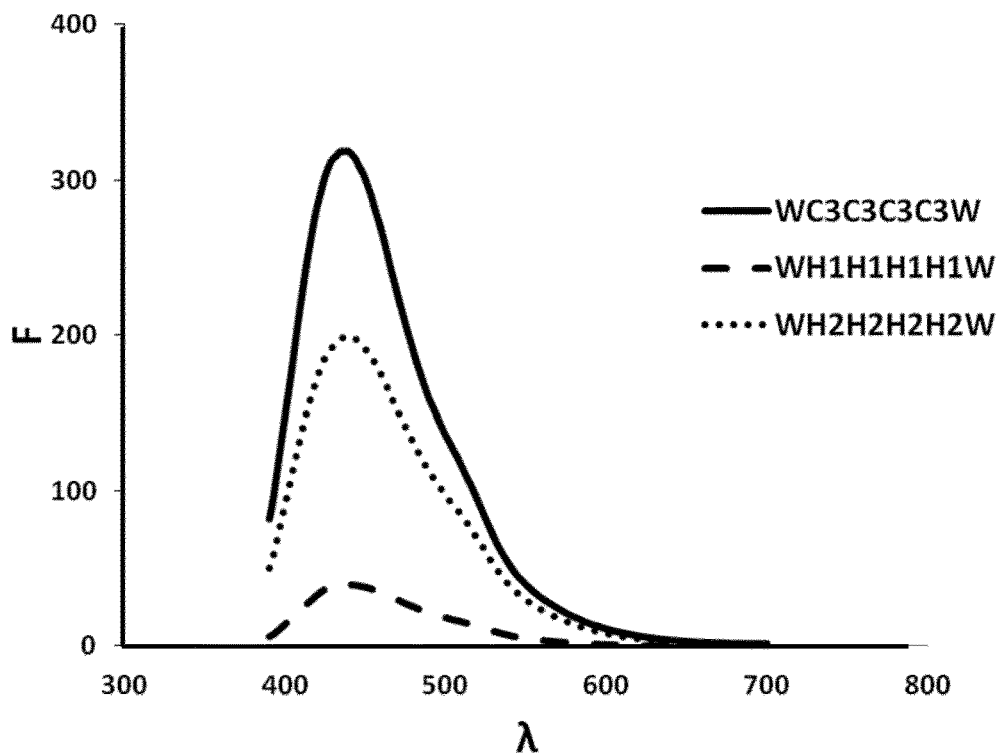
FIG. 10 represents a comparative of the fluorescence emission spectra of different protein-stabilized AuNCs and shows the effect of the cysteine (WC3C3C3C3W) or histidine clamps (WH1H1H1H1W and WH2H2H2H2W). (F: Fluorescence intensity (arbitrary units); λ: wavelength (nm)).

As shown in FIG. 10, AuNCs with large fluorescence emission intensity were obtained using the different CTPR proteins. It was observed an improvement on the fluorescence properties of the stabilized AuNCs by the protein with Cys clamp (WC3C3C3C3W) in comparison with the stabilized AuNCs by proteins with His clamps (WH1H1H1H1W and WH2H2H2H2W). Also it was observed that in the case of stabilized AuNCs by proteins with His clamps (WH1H1H1H1W and WH2H2H2H2W), the His clamp base on H2 module increased the fluorescent properties of the stabilized AuNCs in comparison with the H1 module both with 4 histidine residues. The fluorescence emission spectra of the products consisted in all the cases of a single peak with a maximum at 440-450 nm, when excited at 370-380 nm (FIG. 10).

Comparison of the Efficiency in the Synthesis and Stabilization of Metal Nanoclusters Between the Design Proteins of the Invention and Possible CTPR-Based Random Mutants Containing Cysteine Residues The efficiency of the design proteins of the invention in comparison with other possible CTPR-based random mutants containing cysteine residues in the synthesis and stabilization of metal nanoclusters was evaluated using the same experimental conditions (reducing agent, ratio protein: metal:reducing agent, and reaction time).

Different CTPRs proteins were tested for the synthesis and stabilization of metal nanoclusters (WWW, WWW_cys, WC1W, WC2W, WC3W, WHW, WH2W, WH3W, WRW, WR1W and WR2W). The effect of the protein sequence in the synthesis and stabilization of metal nanoclusters using the same experimental conditions described in the materials and methods was evaluated. The fluorescence spectra of the samples were acquired showing in all cases the characteristic fluorescence corresponding to protein stabilized metal NCs (FIGS. 11, 12 and 13). After evaluating the importance of the presence and position of the Cys and/or His residues, a remarkable improvement in the fluorescent properties of the stabilized metal NCs was detected using the design proteins of the invention in comparison with CTPR-based random mutants containing cysteine residues (WRW, WR1W and WR2W).

As shown in FIGS. 11, 12 and 13, metal NCs with large fluorescence emission intensity were obtained using the different CTPR proteins. It was observed an improvement on the fluorescence properties of the stabilized metal NCs by the protein with design His clamps (WHW, WH2W and WH3W) and Cys clamps (WC1W, WC2W and WC3W) in comparison with the stabilized metal NCs by CTPR protein base random mutants containing cysteine residues with (WRW, WR1W and WR2W), showing that the position of the histidine and cysteine residues in the repeated modules is critical for the synthesis and stabilization of metal NCs with strong fluorescence. In addition, it was observed the metal NCs stabilized by the designed cys clamps (WC1W, WC2W and WC3W) showed increased fluorescence compared to the metal NCs stabilized by the His clamps (WHW, WH2W and WH3W). A general improvement in the fluorescent properties of the stabilized metal NCs was observed increasing the number of Cys residues up to 4 (from WC1W with 2 cysteines to WC3W with 4 cysteines). The fluorescence emission spectra of the products consisted in all cases of a single peak with a maximum at 440-450 nm, when excited at 370-380 nm.

Fluorescent CdS Nanoclusters Comprising CTPR Variant with Coordinating Residues Based on Histidine Clamps:

The capability of CTPR proteins, formed by different number of CTPR modules, to act as templates for the synthesis and stabilization of CdS nanoclusters was explored. In addition, the effect of the presence and position of specific metal-binding sites composed by different numbers of histidine residues in the protein structure on the formation and stabilization of CdS NCs was evaluated.

Six different CTPRs proteins were designed, expressed and produced for the synthesis and stabilization of CdS nanoclusters) by combining H1 and H2 modules with wild type CTPR modules (W): WWWWWW, WH1W, WH1H1W, WH1H1H1W, WH1H1H1H1W and WH2H2H2H2W, as indicated in table 2 and in materials and methods section. The designed CTPRs were tested for the generation of protein-stabilized CdS nanoclusters. The effect of the protein sequence in the synthesis and stabilization of CdS nanoclusters using the same experimental conditions described in the materials and methods was evaluated.

As observed in FIG. 14, the presence of histidine residues in the protein structure favors the synthesis and stabilization of CdS nanoclusters. The WWWWWW protein with no histidines did not result in a significant production of CdS nanoclusters. Remarkably, the introduction of the designed histidine clamps in the protein increased the fluorescence intensity of the protein stabilized CdS nanoclusters. A remarkable improvement in the fluorescent properties of the stabilized CdS nanoclusters was detected increasing the number of His residues up to 16. Finally, it was observed that the different position of the histidine residues in the modules H1 or H2 is not relevant for the synthesis and stabilization of CdS nanoclusters. WH1H1H1H1W-CdS NCs and WH2H2H2H2W-CdS NCs showed similar fluorescent properties.

The fluorescence emission spectrum of the main product consisted of a peak with a maximum at 515-520 nm, when excited at 365 nm FIG. 14 The excitation spectrum showed in all cases a single peak with a maximum at 360-365 nm (FIG. 15).

Metal NCs Stabilized by the Proteins of the Invention as Sensors of Ligands:

The properties of the CTPRs can be easily modulated, such as the binding recognition site; hence TPR proteins with the same structure but with different binding activity were created by introducing few variations in the primary sequence. These CTPR modules with different binding activity can be combined with the Cys clamp modules to produce fluorescent AuNCs in order to design tailored sensors, biomarkers or different tools for biomedical applications. The potential of CTPR-stabilized AuNCs as molecular probes by combining the fluorescence of AuNCs and the binding capability of the protein was investigated. As a proof-of-concept, three CTPR scaffolds that binds the C-terminal peptide of Hsp90 (CTPR390, TPR2A and TPR2A_T332R_D334K), chaperone essential for the folding of many oncogenic proteins and thus involved in tumor progression, were combined with CC1_4Cys clamp used for the generation of AuNCs. Hereby it was demonstrated that the CC1-CTPR390-AuNCs, CC1-TPR2A-AuNCs, and CC1TPR2A_T332R_D334K-AuNCs complexes were fluorescent and able to specifically recognize their ligand molecule.

First, the CC1-CTPR390 CC1-TPR2A, and CC1-TPR2A_T332R_D334K proteins were designed, expressed, produced and characterized as previously described in the materials and methods section. Then these novel proteins were characterized by checking their folding, stability (thermal unfolding) and ligand binding affinity (FIG. 16).

Figure 16:
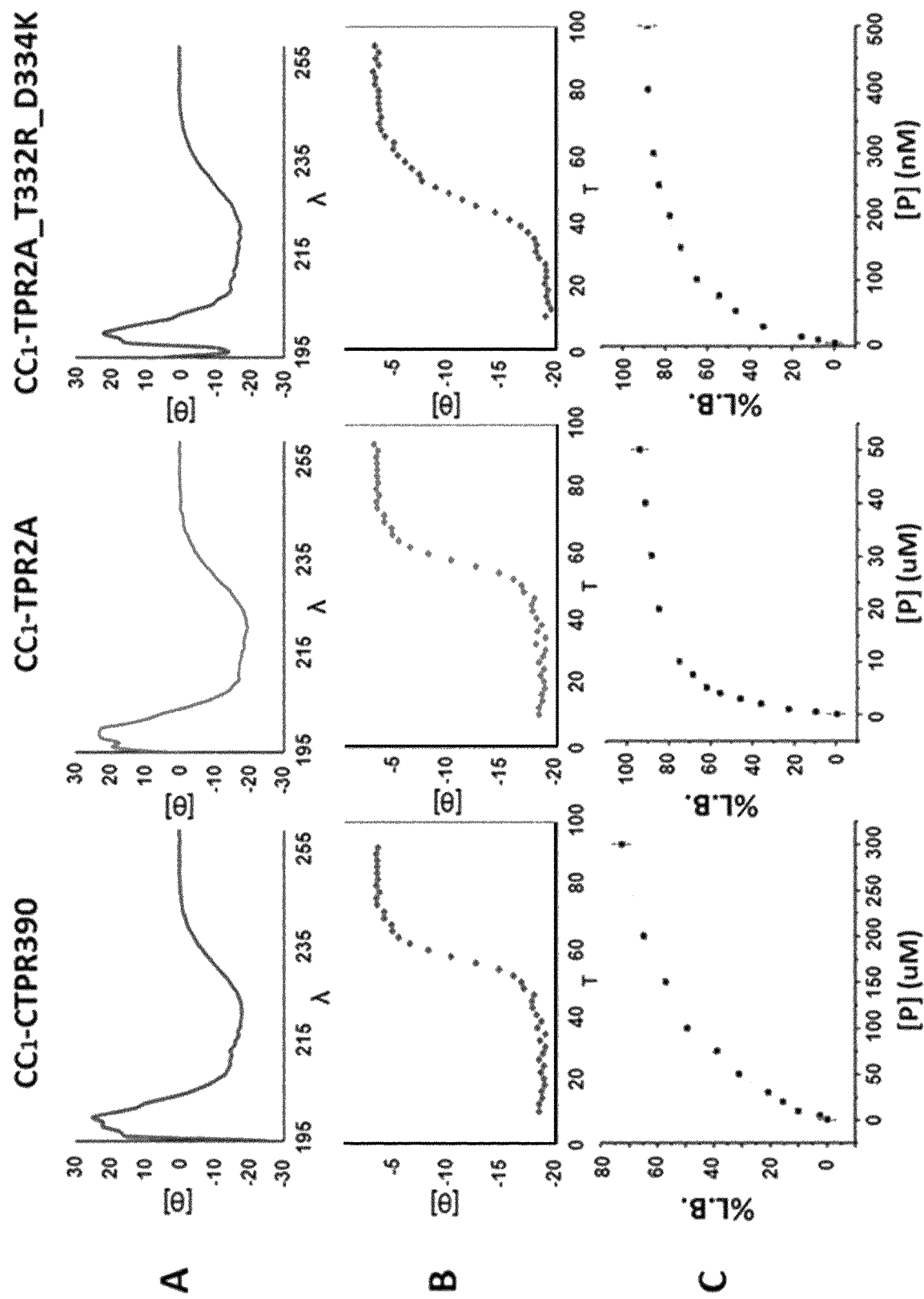
FIG. 16 shows the circular dichroism spectra (A), the thermal unfolding (B) and the ligand binding activity to Hsp90 (C) of CC1-CTPR390, CC1-TPR2A and CC1-TPR2A_T332R_D334K. ([θ]: CD signal (mdeg); λ: wavelength (nm); T: temperature (° C.); % L.B.: percentage of ligand bound; [P]: protein concentration).

As it can be seen in the FIG. 16, the new designed proteins, CC1-CTPR390, CC1-TPR2A, and CC1-TPR2A_T332R_D334K, were well folded, presented a melting temperature (Tm) of 58, 56 and 52° C. and a Kd value of 110 µM, 5 µM and 55 nM (similar to original CTPR390, TPR2A and TPR2A_T332R_D334K).

Then these three designed CTPRs were tested for the generation of protein-stabilized gold NCs using sodium ascorbate as reducing agent and using the same experimental conditions as described in the materials and methods section (reducing agent, ratio cysteine:metal:reducing agent and reaction time). The fluorescence excitation spectra of the three different protein-stabilized gold NCs showed a maximum at 370 nm and the emission spectra a maximum at 450 nm when excited at 370 nm. Since the structural and functional properties of CTPR repeats were of interest, it was tested whether the protein secondary structure and ligand binding activity were maintained after the CTPR-AuNCs synthesis.

The CD analysis of the sample after the CTPR-AuNCs formation using mild reducing agents revealed that the protein structure was retained (FIG. 16). Thus, the optimized AuNCs synthesis protocol using sodium ascorbate resulted in protein stabilized AuNCs with good fluorescent properties and the structural integrity of the protein scaffold.

Finally, fluorescence anisotropy was used to monitor the interaction between the CC1-CTPR390-AuNCs, CC1-TPR2A-AuNCs and CC1-TPR2A_T332R_D334K-AuNCs complexes and a fluorescein-labeled Hsp90 peptide to determine the corresponding Kd value. The results showed that the capability of the protein to recognize the Hsp90 peptide was not affected by the nanocluster formation. The Kd values obtained for the interaction were about 110 µM, 5 µM and 55 nM, comparable to the values obtained when using the same assay for the proteins (FIG. 16). This data confirmed that the formation of gold nanoclusters did not alter the binding domain, which is key to use this new methodology to develop tools for bioimaging and sensing.

The fluorescence of the AuNCs in the CC1-CTPR390-AuNCs complex was used as a sensor to detect the presence of Hsp90 peptide. An increase of the AuNCs fluorescence when Hsp90 peptide was added to a solution containing CC1-CTPR390-AuNCs was observed. The ligand peptide induced a dose-dependent increase in the fluorescence of the AuNCs due to the interaction with its cognate peptide (Hsp90). A linear response of the fluorescence intensity change was observed in the concentration range of 5µ-600 µM.

Use of Metal Fluorescent NCs of the Invention as Temperature Sensors:

Blue-emitting WHW stabilized CuNCs synthetized as previously describe the point 5 of the materials and methods (Synthesis of protein-stabilized copper nanoclusters with different emission colors) were used as temperature sensor.

Figure 17:
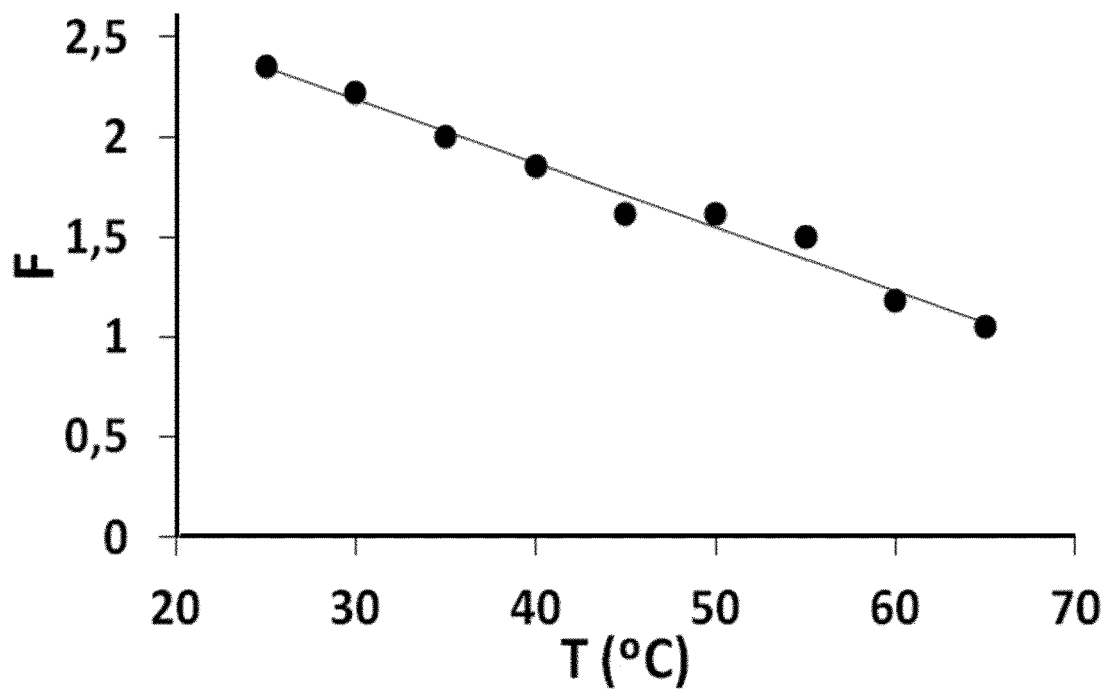
FIG. 17 shows the fluorescence intensity (F) of Cu nanoclusters stabilized by WHW protein as a function of the temperature T (° C.).

The intensity of the fluorescence emission of the protein-stabilized copper nanoclusters had a linear dependence with the temperature in a range from 25 to 65° C. as observed in the FIG. 17.

Use of Metal Fluorescent NCs of the Invention as Imaging Agent.

Figure 18:
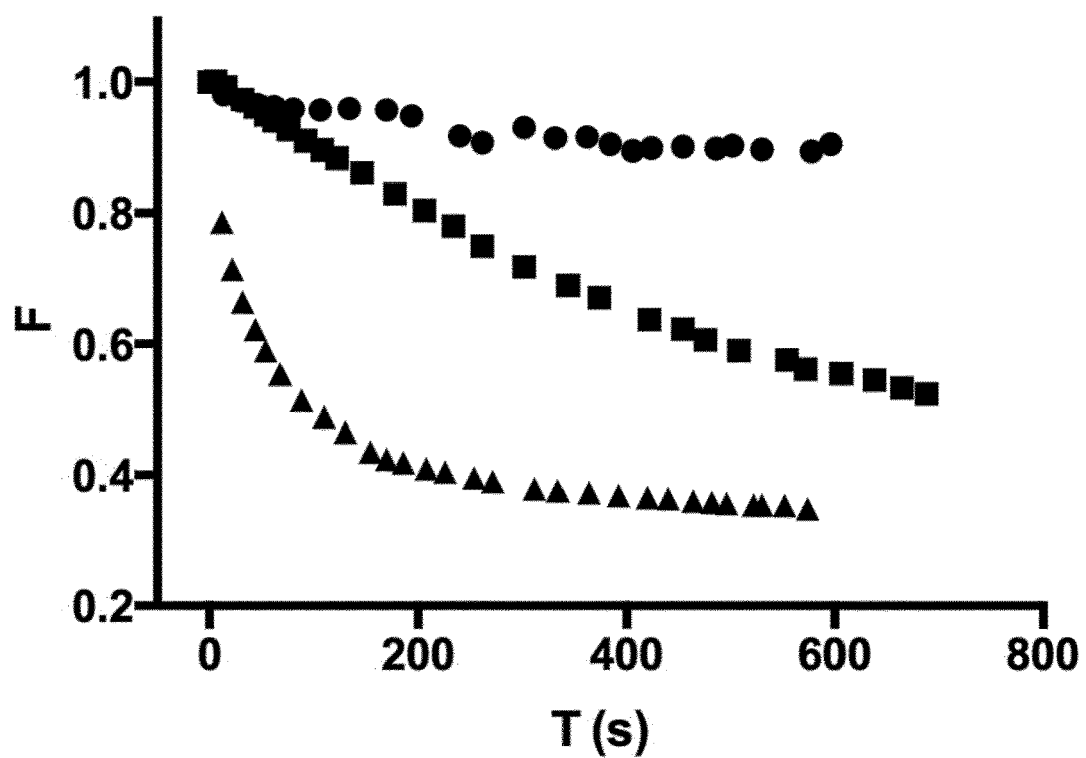
FIG. 18 represents the photobleaching curves over time of the fluorescence intensity of AgNCs (solid circles) in comparison with the GFP (solid squares) and DAPI (solid triangles).

Conventional fluorophores for imaging applications include organic dyes and engineered fluorescent proteins, which have limited photostability that can be a disadvantage for long-term experiments in live cells. The present invention demonstrates that the metal fluorescent NC of the invention shows better photostability than a commonly used fluorescent protein, Green Fluorescent Protein (GFP) and the dye 4',6-diamidino-2-phenylindole (DAPI). In FIG. 18 it can be observed the photobleaching curve under a fluorescence microscope illumination wherein the increased photostability of WHW stabilized AgNCs over the GFP and DAPI is demonstrated. Therefore it is shown that the metal fluorescent NC of the invention is a suitable tool as imaging agent, for in vitro an in vivo applications.

CITATION LIST

Couleaud P et al. 2015 Biomacromolecules 16:3836-3844.

D'Andrea L et al. 2003 Trends Biochem. Sci., 2003, 28, 655-662.

Huang H et al. 2014 The Royal Society of Chemistry DOI: 10.1039/c4an01757a

Li J et al. 2014 Trend in Analytical Chemistry 58:90-98.

Qu X et al. 2015 Journal of Nanomaterials Article ID 784097

Shang L et al. 2011 Nano Today 6:401-418

Xie J et al. 2009 J Am Chem Soc 131:888-889

For reasons of completeness, various aspects of the invention are set out in the following numbered clauses:

Clause 1. An amino acid sequence consisting of sequence SEQ ID NO: 1 or a salt thereof:

$$AX_1AWX_2X_3LGX_4AYX_5X_6 \quad \text{(SEQ ID NO: 1)}$$

wherein
X$_1$ is an amino acid selected from E, H, C, and D;
X$_2$ is an amino acid selected from Y, H, C, D and E;
X$_3$ is an amino acid selected from N, H, C, D and E;
X$_4$ is an amino acid selected from N, H, C, D and E;
X$_5$ is an amino acid selected from Y, H, L, A, V, C, D and E;
X$_6$ is an amino acid selected from K, H, C, D and E;
provided that:
at least two of X$_1$, X$_2$, X$_3$, X$_4$, X$_5$ and X$_6$ are the same or different and represent H, C, D or E;
when X$_2$ is H, C, D or E, then X$_3$ is N; and,
when X$_3$ is H, C, D or E, then X$_2$ is Y.

Clause 2. The amino acid sequence of clause 1 which is selected from the group consisting of:

$$AX_1AWX_2NLGNAYYK; \quad \text{(SEQ ID NO: 2)}$$

$$AX_1AWYX_3LGNAYYK; \quad \text{(SEQ ID NO: 3)}$$

$$AEAWX_2NLGX_4AYYK; \quad \text{(SEQ ID NO: 4)}$$

$$AEAWYX_3LGX_4AYYK; \quad \text{(SEQ ID NO: 5)}$$

$$AEAWYNLGX_4AYX_5K; \quad \text{(SEQ ID NO: 6)}$$

$$AX_1AWX_2NLGX_4AYYK; \quad \text{(SEQ ID NO: 7)}$$

$$AX_1AWYX_3LGX_4AYYK; \quad \text{(SEQ ID NO: 8)}$$

$$AEAWX_2NLGX_4AYX_5K; \quad \text{(SEQ ID NO: 9)}$$

$$AEAWYX_3LGX_4AYX_5K; \quad \text{(SEQ ID NO: 10)}$$

$$AX_1AWX_2NLGX_4AYX_5K; \quad \text{(SEQ ID NO: 11)}$$

$$AX_1AWYX_3LGX_4AYX_5K; \quad \text{(SEQ ID NO: 12)}$$
and $$AX_1AWYX_3LGX_4AYX_5X_6. \quad \text{(SEQ ID NO: 13)}$$

Clause 3. A peptide of formula (I) or a salt thereof:

$$Z—(B)n\text{-}F\text{-}(G)m \quad \text{(I)}$$

wherein n and m is 0 or 1,
Z represents the amino acid sequence of any one of clauses 1 to 2, provided that when X$_1$ is C, then X$_4$ is C, D, E or N,
B represents a linker,
F is amino acid sequence having an alpha helix secondary motif, and
G is a sequence selected from the group consisting of: SEQ ID NO: 23, SEQ ID NO: 24 and SEQ ID NO: 25.

Clause 4. The peptide according to clause 3, which is selected from the group consisting of:

$$AEAWHNLGHAYYKQGDYDEAIEYYQKALELDPRS, \quad \text{(SEQ ID NO: 27)}$$

$$AEAWCNLGCAYYKQGDYDEAIEYYQKALELDPRS, \quad \text{(SEQ ID NO: 29)}$$

$$ACAWYCLGNAYYKQGDYDEAIEYYQKALELDPRS, \quad \text{(SEQ ID NO: 31)}$$

$$ACAWYCLGCAYYKQGDYDEAIEYYQKALELDPRS, \quad \text{(SEQ ID NO: 33)}$$
and $$ACAWYCLGCAYLCQGDYDEAIEYYQKALELDPRS. \quad \text{(SEQ ID NO: 35)}$$

Clause 5. A protein of general formula (II) or a salt thereof:

$$W_nZ_pW_q \quad \text{(II)}$$

wherein
n and q represent integers with a value of from 0 to 10, and p represents an integer with a value from 1 to 10, provided that n+p+q is equal or higher than 2;
W is a peptide comprising the sequence SEQ ID NO: 37 AEAWYNLGNAYYKQGDYDEAIEYYQKALELDPRS, and
Z is an amino acid sequence of any one of clauses 1 to 2 or an amino acid sequence that comprises the peptide of any one of clauses 3 to 4.

Clause 6. The protein of clause 5 which is selected from the group consisting of: SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, and SEQ ID NO: 67.

Clause 7. The protein of any one of clauses 5 or 6 which is bound to an element selected from the group consisting of: a peptide, a nanoparticle, a nucleic acid, an inorganic molecule, an organic molecule, a lipid, a monosaccharide, an oligossacharide, an enzyme, an antibody, an antigen, a tag peptide, an MRI contrast agent, a PET contrast agent, a coordinating metal contrast agent, and any combination thereof.

Clause 8. A nucleic acid sequence coding for the amino acid sequence of any one of clause 1 or 2 or the peptide of any one of claim 3 or 4 or the protein of any one of claims 5 to 7.

Clause 9. Use of the amino acid sequence of any one of clause 1 or 2, the peptide of any one of clause 3 or 4, or the protein of any one of clause 5 to 7 as a metal nanocluster scaffold.

Clause 10. A metal nanocluster comprising the amino acid sequence of any one of clauses 1 or 2, the peptide of any one of clauses 3 or 4 or the protein of any one of clauses 5 to 7.

Clause 11. The metal nanocluster of clause 10, comprising copper, gold, silver, nickel, zinc, titanium, chromium, iron, cobalt, palladium, cadmium, ruthenium, rhodium, iridium, platinum or a combination thereof.

Clause 12. A process for the production of a metal nanocluster of any one of clauses 10 or 11 comprising the steps of:
a) mixing the protein of any one of clauses 5 to 7 with a metal containing compound; and
b) subjecting the mixture to a reduction reaction.

Clause 13. The process of clause 12, wherein the metal containing compound is a metallic salt and the reduction is performed by adding a reducing agent in a molar excess with respect to the molar concentration of the metallic salt.

Clause 14. Use of the metal nanocluster of any one of clauses 10 or 11 as imaging agent, as drug-delivery carrier, as metabolic interfering agent, as catalyst, as an analyte, for phasing crystallographic data set, as cell labelling agent, as specific protein labeling agent, as biosensor, as a temperature sensor, as photosensitizer, or for the manufacture of an optoelectronic device.

Clause 15. A kit comprising the amino acid sequence of clauses 1 or 2, the peptide of clauses 3 or 4, the protein of any one of clauses 5 to 7, the nucleic acid sequence of clause 8, or the metal nanocluster of clauses 10 or 11.

The invention claimed is:

1. A peptide consisting of an amino acid sequence set forth in SEQ ID NO: 1 or a salt thereof:

$AX_1AWX_2X_3LGX_4AYX_5X_6$ (SEQ ID NO: 1)

wherein
$X_1$ is an amino acid selected from E, H, C, and D;
$X_2$ is an amino acid selected from Y, H, C, D and E;
$X_3$ is an amino acid selected from N, H, C, D and E;
$X_4$ is an amino acid selected from N, H, C, D and E;
$X_5$ is an amino acid selected from Y, H, L, A, V, C, D and E;
$X_6$ is an amino acid selected from K, H, C, D and E;
provided that at least two of $X_1, X_2, X_3, X_4, X_5$ and $X_6$ are the same or different and represent H, C, D or E.

2. The peptide according to claim 1, provided that:
(a) when $X_2$ is H, C, D or E, then $X_3$ is N; and,
(b) when $X_3$ is H, C, D or E, then $X_2$ is Y.

3. The peptide according to claim 1, provided that when $X_1$ is E, then at least two of $X_2, X_3, X_4, X_5$ and $X_6$ are the same or different and represent H, C, D or E.

4. The peptide according to claim 1, which is selected from the group consisting of:

$AX_1AWX_2NLGNAYYK;$ (SEQ ID NO: 2)

$AX_1AWYX_3LGNAYYK;$ (SEQ ID NO: 3)

$AEAWX_2NLGX_4AYYK;$ (SEQ ID NO: 4)

$AEAWYX_3LGX_4AYYK;$ (SEQ ID NO: 5)

$AEAWYNLGX_4AYX_5K;$ (SEQ ID NO: 6)

$AX_1AWX_2NLGX_4AYYK;$ (SEQ ID NO: 7)

$AX_1AWYX_3LGX_4AYYK;$ (SEQ ID NO: 8)

$AEAWX_2NLGX_4AYX_5K;$ (SEQ ID NO: 9)

$AEAWYX_3LGX_4AYX_5K;$ (SEQ ID NO: 10)

$AX_1AWX_2NLGX_4AYX_5K;$ (SEQ ID NO: 11)

$AX_1AWYX_3LGX_4AYX_5K;$ (SEQ ID NO: 12)

$AX_1AWYX_3LGX_4AYX_5X_6;$ (SEQ ID NO: 13)

$AX_1AWX_2NLGX_4AYYX_6;$ (SEQ ID NO: 110)

$AEAWX_2NLGX_4AYYX_6;$ (SEQ ID NO: 111)

$AEAWYX_3LGX_4AYYX_6;$ (SEQ ID NO: 112)

$AEAWYNLGX_4AYYX_6;$ (SEQ ID NO: 113)

$AX_1AWX_2X_3LGX_4AYYK;$ (SEQ ID NO: 114)

$AX_1AWX_2NLGX_4AYX_5X_6;$ (SEQ ID NO: 167)

and $AX_1AWYNLGX_4AYYK.$ (SEQ ID NO: 168)

5. The peptide according to claim 1, provided that when $X_6$ is H, C, D or E, then $X_5$ is not Y.

6. The peptide according to claim 1, wherein at least two of $X_1, X_2, X_3, X_4, X_5$ and $X_6$ are the same or different and represent H or C.

7. The peptide according to claim 6, which is selected from the group consisting of: SEQ ID NO: 14, SEQ ID NO: 15, SEQ ID NO: 16, SEQ ID NO: 17, SEQ ID NO: 18, SEQ ID NO: 115, SEQ ID NO: 117, SEQ ID NO: 145, SEQ ID NO: 169, and SEQ ID NO: 170.

8. A peptide of formula (I) or a salt thereof:

$Z—(B)n\text{-F-}(G)m$ (I)

wherein n and m is 0 or 1,
Z represents the peptide according to claim 1, provided that when $X^1$ is C, then $X_4$ is C, D, E or N,
B represents a linker,
F is amino acid sequence having an alpha helix secondary motif, and
G is a sequence selected from the group consisting of: SEQ ID NO: 23, SEQ ID NO: 24 and SEQ ID NO: 25.

9. The peptide according to claim 8, which is selected from the group consisting of:

AEAWHNLGHAYYKQGDYDEAIEYYQKALELDPRS, (SEQ ID NO: 27)

AEAWCNLGCAYYKQGDYDEAIEYYQKALELDPRS, (SEQ ID NO: 29)

ACAWYCLGNAYYKQGDYDEAIEYYQKALELDPRS, (SEQ ID NO: 31)

ACAWYCLGCAYYKQGDYDEAIEYYQKALELDPRS, (SEQ ID NO: 33)

ACAWYCLGCAYLCQGDYDEAIEYYQKALELDPRS, (SEQ ID NO: 35)

ACAWYHLGNAYYKQGDYDEAIEYYQKALELDPRS, (SEQ ID NO: 97)

ACAWYNLGHAYYKQGDYDEAIEYYQKALELDPRS, (SEQ ID NO: 99)

-continued

AHAWHHLGHAYYKQGDYDEAIEYYQKALELDPRS, (SEQ ID NO: 119)

AHAWHNLGHAYLHQGDYDEAIEYYQKALELDPRS, (SEQ ID NO: 121)
and

AHAWHNLGHAYYKQGDYDEAIEYYQKALELDPRS. (SEQ ID NO: 147)

10. A protein of general formula (II) or a salt thereof:

$$W_n Z_p W_q \quad (II)$$

wherein n and q represent integers with a value of from 0 to 10, wherein n and q are the same or different and they are different from 0; and p represents an integer with a value from 1 to 10, provided that n+p+q is equal or higher than 2;

W is a peptide comprising the sequence AEAWYNLGNAYYKQGDYDEAIEYYQKALELDPRS (SEQ ID NO: 37), and Z is an amino acid sequence that comprises the peptide according to claim 9; or alternatively, a protein of sequence SEQ ID NO: 91, SEQ ID NO: 93 or SEQ ID NO: 95.

11. The protein according to claim 10, which is selected from the group consisting of: SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 101, SEQ ID NO: 103, SEQ ID NO: 105, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141 SEQ ID NO: 155, SEQ ID NO: 157 and SEQ ID NO: 159.

12. The protein according to claim 10, which is bound to an element selected from the group consisting of: a peptide, a nanoparticle, a nucleic acid, an inorganic molecule, an organic molecule, a lipid, a monosaccharide, an oligossacharide, an enzyme, an antibody, an antigen, a tag peptide, an MM contrast agent, a PET contrast agent, a coordinating metal contrast agent, and any combination thereof.

13. A metal nanocluster comprising the peptide as defined in claim 8 or the protein as defined in claim 10.

14. A process for the production of a metal nanocluster according to claim 13, comprising the steps of:
(a) mixing the protein as defined in claim 10 with a metal containing compound; and
(b) subjecting the mixture to a reduction reaction.

15. The process according to claim 14, wherein the metal containing compound is a metallic salt and the reduction is performed by adding a reducing agent in a molar excess with respect to the molar concentration of the metallic salt.

16. The protein according to claim 10, which is of general formula:

$$WZ_p W$$

wherein W, Z and p are as defined in claim 10.

17. The protein according to claim 16, which is bound to an element selected from the group consisting of: a peptide, a nanoparticle, a nucleic acid, an inorganic molecule, an organic molecule, a lipid, a monosaccharide, an oligosaccharide, an enzyme, an antibody, an antigen, a tag peptide, an MRI contrast agent, a PET contrast agent, a coordinating metal contrast agent, and any combination thereof.

18. A metal nanocluster comprising the protein according to claim 16.

19. The process of claim 14, wherein the process further comprises expressing the protein from an expression cassette prior to step (a).

* * * * *